(12) United States Patent
Boehlert

(10) Patent No.: US 7,682,473 B2
(45) Date of Patent: Mar. 23, 2010

(54) TI, AL AND NB ALLOYS

(75) Inventor: Carl J. Boehlert, Okemos, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 421 days.

(21) Appl. No.: 11/583,666

(22) Filed: Oct. 18, 2006

(65) Prior Publication Data
US 2007/0084530 A1    Apr. 19, 2007

Related U.S. Application Data

(60) Provisional application No. 60/728,130, filed on Oct. 19, 2005.

(51) Int. Cl.
*C22F 1/18* (2006.01)
*A61F 2/02* (2006.01)
*C22C 14/00* (2006.01)
*C22C 27/02* (2006.01)

(52) U.S. Cl. .................. 148/670; 623/11.11; 148/421; 420/417; 420/418; 420/425; 420/426

(58) Field of Classification Search ................ 148/417, 148/418, 421, 425, 426, 670; 623/11.11; 420/417, 418, 425, 426
See application file for complete search history.

(56) References Cited

U.S. PATENT DOCUMENTS

| 5,169,597 | A | * | 12/1992 | Davidson et al. ............ 428/613 |
| 5,310,464 | A |   | 5/1994  | Redepenning |
| 5,413,693 | A |   | 5/1995  | Redepenning |
| 2001/0039454 | A1 |   | 11/2001 | Ricci et al. |
| 2005/0011596 | A1 | * | 1/2005  | Tanaka et al. ............... 148/670 |
| 2005/0048193 | A1 |   | 3/2005  | Li et al. |

FOREIGN PATENT DOCUMENTS

GB    1325269 A  *  8/1973

OTHER PUBLICATIONS

Boehlert et al., Tensile and fatigue evaluation of Ti-15Al-33Nb (at%) and Ti-21Al-29Nb (at%) alloys for biomedical applications, Jun. 6, 2005, Materials Science and Engineering C, Elsevier, vol. 25, p. 263-275.*
Oliveira et al., Preparation and Characterization of Ti-Al-Nb Alloys For Orthopedic Implants, Brazilian Journal of Chemical Engineering, 1998, vol. 15, n. 4, pp. 326-333.*
M. Niinomi, Metal Mater. Trans. 33A, (2002) pp. 477-486.
M.F. Lopez, J.A. Jimenez, A. Gutierrez. Corrosion Study of Surface-Modified Vanadium-Free Titanium Alloyws. Electrochimica Acta 48 (2003) pp. 1395-1401.
M. Metikos-Hukovic, E. Tkalcec, A. Kwokal, J. Piijac, Surface and Coatings Technology, 165 (2003), pp. 40-50.
Z. Chai, T. Shafter, I. Watanabe, M.E. Nunn, T. Okabe, Biomaterials 24 (2003), pp. 213-218.
D. Iijima, T. Yoneyama, H. Doi, H. Hamanaka, N. Kurosaki. Wear Properties of Ti and Ti-gAl-7Nb Castings for Dental Prostheses. Biomaterials 24 (2003), pp. 1519-1524.
M.A. Khan, R.L. Williams*, D.R. Williams, Biomaterials 20 (1999), pp. 631-637.
M. Papkyriacou, H. Mayer, C. Pypen, H. Plenk Jr, and S. Stanzl-Tschegg. Effects of Surface Treatments on High Cycle Corrosion Fatigue of Metallic Implant Materials. International Journal of Fatigue 22 (2000) 873-886.
M.F. Semlitsch, H. Weber, R.M. Streicher, and R Schon, Biomaterials (1992) vol. 13, No. 11 pp. 781-788.
I. Watanabe, Y. Tanaka, E. Watanabe, and K. Hisatsune, Tensile Properties and Hardness of Cast Fe-Pt Magnetic Alloys. The Journal of Prosthetic Dentistry (2004) vol. 92 No. 3 pp. 278-282.
T. Akahori, M. Niinomi, K. Fukunaga, I. Inagaki, Metallurgical and Materials Transactions, 31A (2000) 1949-1958.
M. Niinomi, Fatigue Performance and Cyto-toxicity of Low Rigidity Titanium Alloy, Ti-29Nb-13Ta-4.6Zr. Biomaterials 24 (2003) 2673-2683.
Standard Test Methods for Determining Grain Size Designation E 112-88, American Society for Testing and Materials (ASTM), West Conshohocken, PA, 1988, pp. 282-307.
Boehlert, C.J. Understanding Microstructure-Property Relationships of Titanium Alloys, Alfred University, New York State College of Ceramics, School of Ceramic Engineering and Materials Science, New York State web site (2002).
Boehlert, C.J., The Effects of Forging and Rolling on Microstructure in O+BCC Ti-Al-Nb Alloys, pp. 118-129, 2000, Materials Science and Engineering, A279/1-2.
Boehlert, C.J., Microstructure, Creep, and Tensile behavior of a Ti-12Al-38Nb (at.%) Beta +Orthorhombic Alloy, pp. 82-98, 1999, Materials Science and Engineering, A267.
Boehlert, C.J., B.S. Majumdar, V. Seetharaman, and D.B. Miracle, Microstructural Evolution in Ti-Al-Nb O+ BCC Alloys, pp. 1999-2323, 1999, Metallurgical Transactions.
Boehlert, C.J., and D.B. Miracle, Part II. The Creep Behavior of Ti-Al-Nb O+BCC Orthorhombic Alloys, pp. 2349-2367 (1999); Metallurgical Transactions.

(Continued)

*Primary Examiner*—Roy King
*Assistant Examiner*—Caitlin Fogarty
(74) *Attorney, Agent, or Firm*—Ian C. McLeod

(57) ABSTRACT

A method for forming a finished implant prosthesis which comprises:
(a) providing an unforged alloy consisting essentially of Ti(x %)Al(y %)Nb wherein x is between about 45 to 54% by atoms, y is between about 15 to 25% by atoms and the balance is niobium;
(b) forging the alloy at an elevated temperature below a melting point of the alloy in a shape which is an implant preform; and
(c) machining the implant preform to provide a machined implant; and
(d) finishing the exposed surfaces of the implant so as to provide the exposed surfaces with a finish which provides biocompatibility, to thereby form the implant prosthesis.

16 Claims, 49 Drawing Sheets
(19 of 49 Drawing Sheet(s) Filed in Color)

OTHER PUBLICATIONS

Boehlertz C.J., Part III. The Tensile Behavior of Ti-Al-Nb O+BCC Orthorhombic Alloys, Metallurgical Transactions, pp. 1977-1988 (2001); Metallurgical Transactions.

W.H. Harris: Clin. Orthop. (1995), pp. 46-53.

A.D. Hanssen and J.A. Rand: J. Bone Jt. Surg. Am. 70 (1988), pp. 491-499.

S.M. Horowitz and M.A. Purdon: Calcif. Tissue Int. 57, (1995), pp. 301-305.

T.T. Glant and J.J. Jacobs: J. Orthop. Res. 12, (1994), pp. 720-731.

A.S. Shanbhag, J.J. Jacobs, J. Black, J.O. Galante, and T.T. Glant: J. Orthop. Res. 13 (1995), pp. 792-801.

T.A. Blaine, P.F. Pollice, R.N. Rosier, P.R. Reynolds, J.E. Puzas, and R.J. O'Keefe: J. Bone Joint Surg. Am. 79 (1997), pp. 1519-1528.

A.A. Ragab, R. Van DeMotter, S.A. Lavish, V.W. Goldberg, J.T. Ninomiya, C.R. Carlin and E.M. Greenfield; J. Orthop. Res. 17 (1999), pp. 803-809.

Y. Kadoya, P.A. Revell, N. Al-Saffar, A. Kobayashi, G. Scott and M.A. Freeman: J. Orthop. Res. 14 (1996), pp. 473-482.

C.S. Lader and A.M. Flanagan: Endocrinology 139 (1998), pp. 3157-3164.

N. Al Saffar and P.A. Revell: Br J. Rheumatol. 33 (1994), pp. 309-316.

T.A. Blaine, R.N. Rosier J.E. Puzas, R.J. Looney, P.R. Reynolds, S.D. Reynolds, and R.J. O'Keefe: J. Bone Joint Surg. Am. 78 (1996), pp. 1181-1192.

K. Kobayashi, N. Takahashi, E. Jimi, N. Udagawa, M. Takami, S. Kotake, N. Nakagawa, M. Kinosaki, K. Yamaguchi, N. Shima, H. Yasuda, T. Morinaga, K. Higashio, T.J. Martin, and T. Suda: J. Exp. Med. 191 (2000), pp. 275-285.

K.D. Merkel, J.M. Erdmann, K.P. McHugh, Y. Abu-Amer, F.P. Ross, and S.L. Teitelbaum: Am. J. Pathol. 154 (1999), pp. 203-210.

Y.H. Kim, J.S. Kim and S.H. Cho: J. Arthroplasty 14 (1999), pp. 538-548.

D. Fender, W.M. Harper and P.J. Gregg: J. Bone Jt. Surg. Br. 81 (1999), pp. 577-581.

J.J. Callaghan, E.E. Forest, J.P. Olejniczak, D.D. Goetz and R.C. Johnston: J. Bone Jt. Surg. Am. 80 (1998), pp. 704-414.

G.C. McKay, R. Macnair, C. MacDonald, and M.H. Grant: Biomaterials 17 (1996), pp. 1339-1344.

T. Akahori, M. Niinomi, K. Fukunaga: Metallurgical and Materials Transactions 31A (2000) 1937-1948.

M. Hagiwara and T. Kitaura, Mater Japan, (1998) 37:35-38.

E.M. Schwarz, E.B. Benz, A.P. Lu, J.J. Goater, A.V. Mollano, R.N. Rosier, J.E. Puzas, and R.J. O'Keefe: Journal of Orthopedic Research 18 (2000) 849-855.

L.M. Childs, J.J. Goater, R.J. O'Keefe, and E.M. Schwarz: Journal of Bone and Mineral Research 16:2 (2001) 338-358.

J.J. Goater, R.J. O'Keefe, R.N. Rosier, J.E. Puzas, and E.M. Schwarz, Journal of Orthopedic Research 20 (2002) 169-173.

K.A. Rider and L.M. Flick: Differentiation of Bone and Soft Tissues in Formalin-fixed, Paraffin-embedded Tissue Using Methylene Blue/Acid Fuchsin Stain, pp. 1-7. 2004.

T.K. Nandy, R.S. Mishra, and D. Banerjee, Creep behavior of an orthorhombic phase in a Ti-Al-Nb alloy, Scr. Metall. Mater. 28 (1993), pp. 569-574.

T.K. Nandy and D. Banerjee, The Mechanical Behavior of the Intermetallic Ti2AlNb, in: M.V. Nathal, R. Darolia, C.T. Liu P.L. Martin, D.B. Miracle, R. Wagner, and M. Yamaguchi (Eds.), Structural Intermetallics, The Minerals, Metals, and Materials Society, Warrendale, PA, 1997, pp. 777-786.

R.G. Rowe et al., Tensile and Creep Behavior of Ordered Orthorhombic Ti2AlNb-Based Alloys, in: L.A. Johnson et al., High Temperature Ordered Intermetallic Alloys IV, The Materials Research Society, Pittsburgh, PA, 1991, pp. 703-708.

C.J. Boehlert and J.F. Bingert, Microstructure, Tensile, and Creep Behavior of O+BCC Ti2AlNb Alloys Processed Using Induction-Float-Zone Melting, J. Mater. Process. Technol., 117 (2001), pp. 400-408.

"Standard Test Methods for Determining Average Grain Size," ASTM Designation E112-96e3. American Society for Testing and Materials, West Conshohocken, PA (1996).

C.J. Boehlert et al., Processing and Heat Treatment Effects on the Phase Evolution, Tensile, and Creep Behavior of an Orthorhombic Ti-25Al-25Nb Alloy, in: W.O. Soboyejo et al., Deformation and Fracture of Ordered Interetallic Materials III, The minerals, Metals, and Materials Society, Warrendale, PA, 1996, pp. 565-582.

V. Seetharaman and S.L. Semiatin, Plastic Flow and Microstructure Evolution During Hot Deformation of a Gamma Titanium Aluminide Alloy, Metall. Mater. Trans. A. 28 (1997), pp. 947-954.

P.G. Shewmon, Diffusion in Solids, McGraw-Hill, New York, NY, (1963).

R.W. Hertzberg, Deformation and Fracture Mechanics of Engineering Materials, Fourth Edition, John Wiley and Sons, New York, NY, 1996.

R.W. Evans and B. Wilshire, Creep of Metals and Alloys, The Institute of Metals, New York, NY, 1985.

T.K. Nandy, R.S. Mishra, A.K. Gogia, and D. Banerjee, The effect of Aluminum on the creep behavior of titanium aluminide alloys, Scr. Metall. Mater. 32 (1995), pp. 851-860.

L.A. Bendersky, W.J. Boettinger, and A. Roytburd, Coherent Precipitates in the BCC/Orthorhombic Two-Phase Field of the Ti-Al-Nb System, Acta Metall. Mater. 39 (1991).

C.J. Bowen and C.J. Boehlert, Microstructure, Creep, and Tensile Behavior of a Ti-15Al-33Nb (at.%) Beta+Orthorhombic Alloy, Philosophical Magazine, in print. 2006.

F. Popille and J. Douin, The dislocation microstructure in orthorhombic O Ti2AlNb deformed between RT and 800°C, Philosophical. Magazine 73, (1996), pp. 1401-1418.

R.G. Rowe, The Mechanical Properties of Ternary and Quaternary Ti2NbAl-Based Titanium Aluminide Alloys, in: F.H. Froes and I. Caplan (Eds.), Titanium '92 Science and Technology, The Minerals, Metals, and Materials Society, Warrendale, PA (1993), pp. 343-350.

R.G. Rowe and M. Larsen, The Effect of Microsstructure and Composition on the Creep Behavior of O Phase Titanium Aluminide Alloys, in: P.A. Blenkinsop, W.J. Evans, and H.M. Flowers (Eds.), Titanium 1995, The University Press, Cambridge, UK, 1996, p. 364-371.

* cited by examiner 75.00 µm = 100 steps   Phase 50.00 µm = 100 steps   Phase

TI, AL AND NB ALLOYS

CROSS-REFERENCE TO RELATED APPLICATION(S)

This application claims benefit to Provisional Application Ser. No. 60/728,130, filed Oct. 19, 2005 which is incorporated herein by reference in its entirety.

STATEMENT REGARDING FEDERALLY SPONSORED RESEARCH OR DEVELOPMENT

This invention was made under National Science Foundation Grant Nos. DMR-0134789 and 0533954. The U.S. government has certain rights to this invention.

BACKGROUND OF THE INVENTION (1) Field of the Invention

The present invention relates to specific Ti, Al and Nb alloys which are useful for various structures and particularly for biomedical applications, such as for implants in the human or lower mammalian body. In particular, the present invention relates to Ti-15 Al-33Nb and Ti-21 Al-29 Nb alloys for biomedical applications.

(2) Description of the Related Art

Erosive bone diseases, such as osteoporosis, periodontitis, rheumatoid arthritis, hypercalcemia of malignancy and aseptic loosening, are a growing medical problem which can lead to the need for replacement surgery with bone-replacement materials. Such materials must exhibit several characteristics in order to be successful including biocompatibility with near-bone hard and soft tissue, a modulus near that for bone to prevent stress shielding, and a tensile and compressive strength and fracture toughness equal to or greater than that of bone. In addition, the fatigue strength of the material should guarantee a safe operation of the implant during the expected period of use. Due to their excellent specific strength and electrochemical corrosion resistance, in addition to exceptional biocompatibility characteristics (i.e. benign biological responses) among metallic biomaterials, commercially pure titanium (cp-Ti) and $\alpha/\beta$ type Ti alloys are currently widely used as structural biomaterials for the replacement of hard tissues in devices such as artificial knee joints and dental implants. However, attempts to develop specific Ti—Al—Nb alloys as biocompatible systems have been lacking.

The recent trend in research and development of titanium alloys for biomedical applications is to develop low rigidity $\beta$-type titanium alloys composed of non-toxic and non-allergic elements with excellent mechanical properties, especially fatigue resistance, and workability (ASTM designation draft #3. Standard specification for wrought titanium-35 Niobium-7zirconium-5tantalum alloy for surgical implant applications (UNS R58350), Philadelphia, Pa., ASTM, 2000; ASTM designation draft #6, Standard specification for wrought titanium-3aluminum-2.5vanadium alloy seamless tubing for surgical implant applications *UNS R-56320), Philadelphia, Pa., ASTM, 2000; J. A. Davidson, F. S. Georgette, Proceedings of the implant manufacturing and material technology. Society of Manufacturing Engineers, Dearborn, 1987: EM87-122-1-EM87-122-26; and M. Niinomi, Metal Mater. Trans. 33A, (2002) pages 477-486)). New titanium alloys for biomedical applications are now being included in American Society for Testing and Materials (ASTM) standards. For example, $\beta$ Ti-15 Mo(wt. %) (ASTM designation F2066-01, Standard specification for wrought titanium-15 molybdenum alloy for surgical implant applications, Philadelphia, Pa., ASTM, pages 1605-1608), Ti-35Nb-7Zr-5Ta(wt. %) (ASTM designation draft #3, ibid), and Ti-3Al-2.5V(wt. %) (ASTM designation draft #6, ibid) have been registered or are in the process of being registered in ASTM standards. $\beta$-type titanium alloys have been developed in order to obtain low rigidity, which is considered effective for promoting bone healing and remodeling. Although the rigidity of $\alpha/\beta$ type titanium alloys is less than that of Co—Cr type alloys and stainless steels used for biomedical applications, it is still considerably greater than that of the cortical bone (J. A. Davidson et al. 1987, ibid).

Several investigations have included newer high titanium alloys based on the Ti—Al—Nb system, such as Ti-6Al-7Nb (wt. %) [Ti-10.5Al-3.6Nb(at. %)] where Nb replaces V (M. F. Lopez, J. A. Jimenez, A. Gutierrez, Electrochimica Acta 48 (2003) pages 1395-1401; M. Metikos-Hukovic, E. Tkalcec, A. Kwokal, J. Piljac, Surface and Coatings Technology, 165 (2003), pages 40-50; Z. Chai, T. Shafter, I. Watanabe, M. E. Nunn, T. Okabe, Biomaterials 24 (2003), pages 213-218; D. Iijima, T. Yoneyama, H. Doi, H. Hamanaka, N. Kurosaki, Biomaterials 24 (2003), pages 1519-1524; M. A. Khan, R. L. Williams*, D. R. Williams, Biomaterials 20 (1999), pages 631-637; M. Papakyriacou, H. Mayer, C. Pypen, H. Plenk Jr., and S. Stanzl-Tschegg, International Journal of Fatigue 22 (2000), pages 873-888; M. F. Semlitsch, H. Weber, R. M. Streicher, and R. Schon, Biomaterials (1992), Vol. 13, No. 11, pages 781-788; I. Watanabe, Y. Tanaka, E. Watanabe, and K. Hisatsune, The Journal of Prosthetic Dentistry (2004) Vol. 92 No. 3 pages 278-282; T. Akahori, M. Niinomi, K. Fukunaga, I. Inagaki, Metallurgical and Materials Transactions, 31A (2000), pages 1949-1958; M. Niinomi, Biomaterials 24 (2003), pages 2673-2683; and "Standard Test Methods for Determining Grain Size Designation E 112-88", American Society for Testing and Materials (ASTM), West Conshohocken, Pa., 1988, pages 228-253)). Substitution of Nb for V is attractive as depending on the concentration of Nb this does not result in degradation of several mechanical properties.

Other prior art is described in:
  Boehlert, C. J., Understanding Microstructure-Property Relationships of Titanium Alloys, Alfred University, New York State College of Ceramics, School of Ceramic Engineering and Materials Science, New York State web site (2002);
  Boehlert, C. J., The Effects of Forging and Rolling on Microstructure in O+BCC Ti—Al—Nb Alloys, pages 1-31, (2000) *Materials Science and Engineering*, A279/1-2;
  Boehlert, C. J., Microstructure, Creep, and Tensile behavior of a Ti-12Al-38Nb(at. %)Beta+Orthorhombic Alloy, pages 1-44, (1999); *Materials Science and Engineering*, A267
  Boehlert, C. J., B. S. Majumdar, V. Seetharaman, and D. B. Miracle, Microstructural Evolution in Ti—Al—Nb O+BCC Alloys, pages 1-41, (1999); *Metallurgical Transactions*
  Boehlert, C. J., and D. B. Miracle, Part II. The Creep Behavior of Ti—Al—Nb O+BCC Orthorhombic Alloys, pages 1-40, (1999); *Metallurgical Transactions* and
  Boehlert, C. J., Part III. The Tensile Behavior of Ti—Al—Nb O+BCC Orthorhombic Alloys, *Metallurgical Transactions*, pages 1-38 (2001); *Metallurgical Transactions*

Currently, more than 1.3 million joint replacement surgeries are performed each year worldwide (W. H. Harris: Clin. Orthop. (1995), pages 46-53), and this number is expected to increase considering the increasing age of the population.

When an implant fails, revision arthroplasty is required, which has a poorer clinical result and shorter duration of survival than the primary joint replacement (A. D. Hanssen and J. A. Rand: J. Bone Jt. Surg. Am. 70 (1988), pages 491-499). Implant failure frequently occurs as a result of osteolysis which is defined as a decrease in bone volume and is characterized by a two millimeter gap between prosthesis and bone as seen in radiographs from arthroplasty patients. Osteolysis can be explained by wear debris generated from the prosthesis which is phagocytosed by macrophages (at the bone-implant interface), which produce proinflamatory cytokines such as tumor necrosis factor α (TNFα), interleukin-1 (IL-1), and IL-6 (S. M. Horowitz and M. A. Purdon: Calcif. Tissue Int. 57, (1995), pages 301-305; T. T. Glant and J. J. Jacobs: J. Orthop. Res. 12, (1994), pages 720-731; J. Y. Want, B. H. Wicklund, R. B. Gustilo and D. T. Tsukayama: Biomaterials 17 (1996), pages 2233-2240; A. S. Shanbhag, J. J. Jacobs, J. Black, J. O. Galante, and T. T. Glant: J. Orthop. Res. 13 (1995), pages 792-801; T. A. Blaine, P. F. Pollice, R. N. Rosier, P. R. Reynolds, J. E. Puzas, and R. J. O'Keffe: J. Bone Joint Surg. Am. 79 (1997), pages 1519-1528; S. H. Lee, F. R. Brennan, J. J. Jacobs, R. M. Urban, D. R. Ragasa, and T. T. Glant: J. Orthop. Res. 15 (1997), pages 40-49; and A. A. Ragab, R. Van DeMotter, S. A. Lavish, V. W. Goldberg, J. T. Ninomiya, C. R. Carlin and E. M. Greenfield; J. Orthop. Res. 17 (1999), pages 803-809)). Release of these cytokines leads to an inflammatory response characterized by the activation and recruitment of osteoclasts, which resorb bone after differentiation and activation, to the bone/implant interface and the formation of a periprosthetic membrane (S. R. Goldring, A. L. Shiller, M. S. Roelke, C. M. Rourke, D. A. O'Neil, and W. H. Harris: J. Bone Joint Surg. Am. 65 (1983), pages 575-584; S. R. Goldring, J. Jasty, M. S. Roelke, C. M. Rourke, F. R. Bringhurst, and W. H. Harris: Arthritis. Rheum. 29 (1986), pages 836-842; and A. S. Shanbhag, J. J. Jacobs, J. Black, J. O. Galante, and T. T. Glant: J. Arthroplasty 10 (1995), pages 498-506)). Due to several factors discussed elsewhere (Y. Kadoya, P. A. Revell, N. al-Saffar, A. Kobayashi, G. Scott and M. A. Freeman: J. Orthop. Res. 14 (1996), pages 473-482; D. R. Bertolini, G. E. Nedwin, T. S. Bringman, D. D. Smith, and G. R. Mundy: Nature 319 (1986), pages 516-518; C. S. Lader and A. M. Flanagan: Endocrinology 139 (1998), pages 3157-3164; N. al Saffar and P. A. Revell: Br J. Rheumatol. 33 (1994), pages 309-316); T. A. Blaine, R. N. Rosier J. E. Puzas, R. J. Looney, P. R. Reynolds, S. D. Reynolds, and R. J. O'Keefe: J. Bone Joint Surg. Am. 78 (1996), pages 1181-1192; and K. Kobayashi, N. Takahashi, E. Jimi, N. Udagawa, M. Takami, S. Kotake, N. Nakagawa, M. Kinosaki, K. Yamaguchi, N. Shima, H. Yasuda, T. Morinnaga, K. Higashio, T. J. Martin, and T. Suda: J. Exp. Med. 191 (2000), pages 275-286)), TNFα is considered to be one of the critical cytokines involved in wear debris-induced osteolysis. Using an animal model of particle-induced osteolysis in which polymethylmethacrylate (PMMA) or CP Ti particles were implanted onto mouse calvaria (E. M. Schwarz and R. J. O'Keefe: Arthritis Rheum. 41 (1998), S345 and K. D. Merkel, J. M. Erdmann, K. P. McHugh, Y. Abu-Amer, F. P. Ross, and S. L. Teitelbaum: Am. J. Pathol. 154 (1999), pages 203-210)), TNFα signaling has been demonstrated to be critical to the development of the inflammatory osteolytic response to wear debris. Overall, up to 20% of patients with total joint replacement will demonstrate evidence of osteolysis within ten years where wear debris-induced osteolysis is the leading culprit, and this currently does not have a proven drug therapy (Y. H. Kim, J. S. Kim and S. H. Cho: J. Arthroplasty 14 (1999), pages 538-548; D. Fender, W. M. Harper and P. J. Gregg: J. Bone Jt. Surg. Br. 81 (1999), pages 577-581; and J. J. Callaghan, E. E. Forest, J. P. Olejniczak, D. D. Goetz and R. C. Johnston: J. Bone Jt. Surg. Am. 80 (1998), pages 704-414)). Thus prevention of osteolysis and prosthetic implant loosening is clearly desirable, and one means to address this issue is through evaluation and improvement of biomedical implant materials and their interaction with living cell and bone tissue.

Due to their exceptional biocompatibility characteristics, CP Ti and α/β type Ti alloys are currently widely used as structural biomaterials for the replacement of hard tissues in devices such as artificial hip joints and dental implants. In particular, Ti-6Al-4V(wt. %) is widely used because of its excellent biocompatibility and its combination of high specific strength, fracture toughness, fatigue and corrosion resistance, ductility, low density, elastic modulus, and conventional processability. However, V is potentially toxic in elemental form (G. C. McKay, R. Macnair, C. MacDonald, and M. H. Grant: Biomaterials 17 (1996), pages 1339-1344); therefore, other alloying elements are currently being examined. In fact, new Ti alloys, targeted for biomedical applications and void of V, are now being included in American Society for Testing and Materials standards (ASTM designation F2066-01: Standard specification for wrought titanium-15 molybdenum alloy for surgical implant applications, (ASTM, Philadelphia, Pa.: USA (2001), pages 1605-1608 and ASTM designation draft #3. Standard specification for wrought titanium-35nNiobium-7zirconium-5tantalum alloy for surgical implant applications (UNS R58350): (ASTM, Philadelphia, Pa., USA)). The recent trend in research and development of Ti alloys for biomedical applications is to develop low rigidity β-type alloys composed of non-toxic and non-allergic elements with attractive mechanical properties (M. Niinomi: Metall. Mater. Trans. 33A (2002), pages 477-486). In this regard, several authors have been evaluating alloys based on the Ti—Al—Nb system, such as Ti-6Al-7Nb (wt. %) [Ti-10.5Al-3.6Nb(at. %)] (M. F. Lopez, J. A. Jimenez, A. Gutierrez: Electrochimica Acta 48 (2003), pages 1395-1401; M. Metikos-Hukovic, E. Tkalcec, A. Kwokal, J. Piljac: Surface and Coatings Technology 165 (2003), pages 40-50; Z. Cai, T. Shafer, I. Wantanabe, M. E. Nunn, T. Okabe: Biomaterials 24 (2003), pages 213-218; D. Iijima, T. Yoneyama, H. Doi, H. Hamanaka, N. Kurosaki: Biomaterials 24 (2003), pages 1519-1524; M. A. Khan, R. L. Williams, D. F. Williams: Biomaterials 20 (1999), pages 631-637; M. Papakyriacou, H. Mayer, C. Pypen, H. Plank Jr., and S. Stanzl-Tschegg: International Journal of Fatigue 22 (2000), pages 873-888; M. R. Semlitsch, H. Weber, R. M. Streicher, and R. Schon:Biomaterials 13:11 (1992), pages 781-788; I. Watanabe, Y. Tanaka, E. Watanabe, and K. Hisatsune: The Journal of Prosthetic Dentistry 92:3 (2004), pages 278-282 and T. Akahori, M. Niinomi, K. Fukunaga, I. Inagaki: Metallurgical and Materials Transactions 31A (2000), pages 1949-1958)).

OBJECTS

It is therefore an object of the present invention to provide implants which are formed from specific alloys of titanium (Ti), aluminum (Al) and niobium (Nb), where Ti is about 5%. It is further an object of the present invention to provide novel alloys of Ti, Al and Nb, which are particularly adapted for implant into mammals, particularly humans. These and other objects will become increasingly apparent from the following description and the drawings.

SUMMARY OF THE INVENTION

The present invention relates to an implant prosthesis in finished form comprising a forged and machined alloy of Ti(x %)Al(y %)Nb, wherein x is about 50% to 52% by atoms, y is about 15% to 21% by atoms and the balance is Nb as an atom percent, wherein the implant is able to withstand at least $10^5$ fatigue cycles at a stress of 400 MPa and has a surface finish which is biocompatible. Preferably, the alloy is Ti-15Al-33Nb. Preferably, the implant is the alloy Ti-21 Al-29Nb. Preferably, the implant prosthesis is biocompatible in mouse testing of implanted micron sized particles of the alloy.

The present invention also relates to a method for forming a finished implant prosthesis which comprises:

(a) providing an unforged alloy of Ti(x %)Al(y %)Nb wherein x is between about 45 to 54% by atoms, y is between about 15 to 25% by atoms and the balance is niobium;

(b) forging the alloy at an elevated temperature below a melting point of the alloy in a shape which is an implant preform;

(c) machining the implant preform to provide a machined implant; and (d) finishing the exposed surfaces of the implant so as to provide the exposed surfaces with a finish which provides biocompatibility, to thereby form the implant prosthesis. Preferably, the alloy is Ti-15Al-33Nb. Preferably, the alloy is Ti-21Al-29Nb. Preferably, the implant prosthesis is biocompatible in mouse testing of implanted micron sized particles of the alloy.

The present invention also relates to a method for treating a patient by implanting an implant prosthesis with modification of a bone surface so as to accept the prosthesis, the improvement which comprises:

(a) implanting the implant prosthesis wherein the implant prosthesis comprises a forged and machined alloy of Ti(x %)Al(y %)Nb, wherein x is between about 45 to 54% by atoms and wherein y is between about 15 to 25% by atoms and the balance is Nb, wherein the implant is able to withstand at least $10^5$ fatigue cycles at a stress of 400 MPa and has a surface finish which is biocompatible. Preferably, the alloy is Ti-15Al33Nb. Preferably, the implant is the alloy Ti-21Al-29Nb. The present invention also relates to a preferred alloy consisting essentially of Ti-15Al-33Nb. The present invention also relates to a preferred alloy consisting essentially of Ti-21Al-29Nb. Preferably, the alloy has been forged and machined as an implant prosthesis.

FIG. 1 shows an implant 10 with a femoral head 11 attached to a neck 12 and with a proximal stem 13 and a distal stem 14 which is implanted into a shaped opening hollowed into the femur adjacent to the hip and femur in the leg. The implant is anchored in place by various surface finishes such as described in U.S. Pat. Nos. 5,310,464 and 5,413,693 to Redepenning; U.S. Patent Application No. 2005/0048193 A1 to Li et al; U.S. Patent Application No. 2001/0039454 A1 to Ricci et al, all of which are incorporated herein by reference in their entireties. Most preferably, the surface 15 of the implant 10 is provided with a roughened surface which enables bonding to the bone without causing a rejection reaction over time in the patient.

Implants fulfill many roles and can be classified either by functional as load bearing, frictional bearing (hip joint replacements), space filling (following resection), and active (pacemakers). Of these classifications load-bearing implants are the most common in both dentistry and bone replacement surgery. The implant should exhibit biocompatibility, defined as the ability of a material to perform with an appropriate host response in a specific application. Osseointegration is the relationship between the bone and the implant and materials which form a diffuse interface layer with bone are said to osseointegrate. Commercially pure Ti, Ti alloys, stainless steel, cobalt-chromium-molybdenum (Co—Cr—Mo) alloys, and bioceramics and bioglasses all osseointegrate with bone; however, metals are the most common implant materials as the ceramics and glasses tend to be brittle thus precluding use in a load bearing environment.

As the market for improved biomedical devices such as artificial hips, knees, shoulders, fingers, and the like is large and ever increasing the broader impact of this invention is to overcome one of the most challenging aspects of artificial joint design, namely poor osseointegration and mismatch of mechanical properties, particularly using novel Ti -21Al-29Nb(at. %) and Ti-15Al-33Nb(at. %) alloys, which are non-toxic, resulting in a Ti-based alloys with superior mechanical properties to those currently in use.

The substance and advantages of the present invention will become increasingly apparent by reference to the following drawings and the description.

DESCRIPTION OF FIGURES

The patent or application file contains at least one drawing executed in color. Copies of this patent with color drawing(s) will be provided by the Patent and Trademark Office upon request and payment of necessary fee.

FIG. 12A is as-processed and FIG. 12B heat-treated microstructures exhibiting faceted fracture with cleavage and some ductile dimples.

FIG. 13A is as-processed and FIG. 13B is heat-treated microstructures exhibiting primarily ductile dimpling in the as-processed condition and mixed-mode fracture in the heat-treated condition.

FIG. 14A is as-processed alloys tested in both air at RT as well as Ringer's solution. FIG. 14B is as-processed alloys tested at RT at both the Fraunhofer Institute (run out=$2\times10^6$ cycles) and Toyohashi University of Technology (run out=$1\times10^7$ cycles).

FIG. 15A is as-processed (AP) and heat-treated (Hted) Ti-21Al-29Nb and Ti-15Al-33Nb alloys tested at RT in the high-stress regime. FIG. 15B is the same data plotted against other biomedical Ti alloys. Note that run out was $1\times10^7$ cycles.

FIG. 16A is a fatigue crack initiation where the arrows indicate the crack growth direction and emanate from the specimen surface. FIG. 16B is a stable crack propagation. FIG. 16C shows overload regions.

FIG. 17A is a fatigue crack initiation. FIG. 17B is a stable crack propagation. FIG. 17C shows overload regions.

FIG. 18A shows high magnification. FIG. 18B shows fracture surface images of the as-processed Ti-21Al-29Nb fatigue-tested samples at 650 MPa applied stress exhibiting brittle fracture characteristics within the crack initiation and propagation regions. Note that the arrows in FIG. 18B indicate the crack growth direction and emanate from the specimen surface.

FIG. 19A Ti-21Al-29Nb; max. cyclic stress=890 MPa, $N_f$=14, 963 and FIG. 19B Ti-15Al-33Nb max. cyclic stress-865 MPa, $N_f$=37, 972 cycles.

FIG. 20A shows Ti-15Al-33Nb (max cyclic stress=450 MPa) and FIG. 20B shows Ti-21Al-29Nb (max cyclic stress=450 MPa).

FIG. 22A shows Ti-15Al-33Nb and FIG. 22B shows Ti-21Al-29Nb sheet microstructures. The matrix consists of the body-centered cubic phase and the dark phase is hexagonal close packed.

FIG. 25A shows baseline and non-particle treated calvaria. FIG. 25B shows $Al_2O_{3-}$. FIG. 25C shows CP Ti. FIG. 25D shows Ti-15Al-33Nb. FIG. 25E shows Ti-21Al-29Nb-treated calvaria. Pink staining indicates bone tissue. Note the wider mid-line sagittal suture (blue staining) in FIGS. 25B and 25C.

FIG. 27A shows baseline and non-particle treated calvaria. FIG. 27B shows $Al_2O_{3-}$. FIG. 27C shows CP Ti. FIG. 27D shows Ti-15Al-33Nb. FIG. 27E shows Ti-21Al-29Nb-treated calvaria. Reddish-brown staining indicates the presence of T-cells in the section.

FIG. 28A shows control. FIG. 28B shows $Al_2O_{3-}$. FIG. 28C shows CP Ti. FIG. 28D shows Ti-15Al-33Nb. FIG. 28E shows Ti-21Al-29Nb by macrophages. All images were taken of stimulated cells after a 24-hour period of incubation in a 37° C. incubator.

(FIG. 31A), 910° C. (FIG. 31B), 960° C. (FIG. 31C), 990° C. (FIG. 31D) and 1005° C. (FIG. 31E) for 3 hours followed by water quenching. The darkest phase is the $\alpha_2$ phase, the lightest phase is B2, and the intermediate contrast phase is O.

FIG. 32A shows HT:960. FIG. 32B shows HT:1005° C. The lightest phase is B2 while the gray phase is O.

DESCRIPTION OF THE PREFERRED EMBODIMENTS

Figure 1:
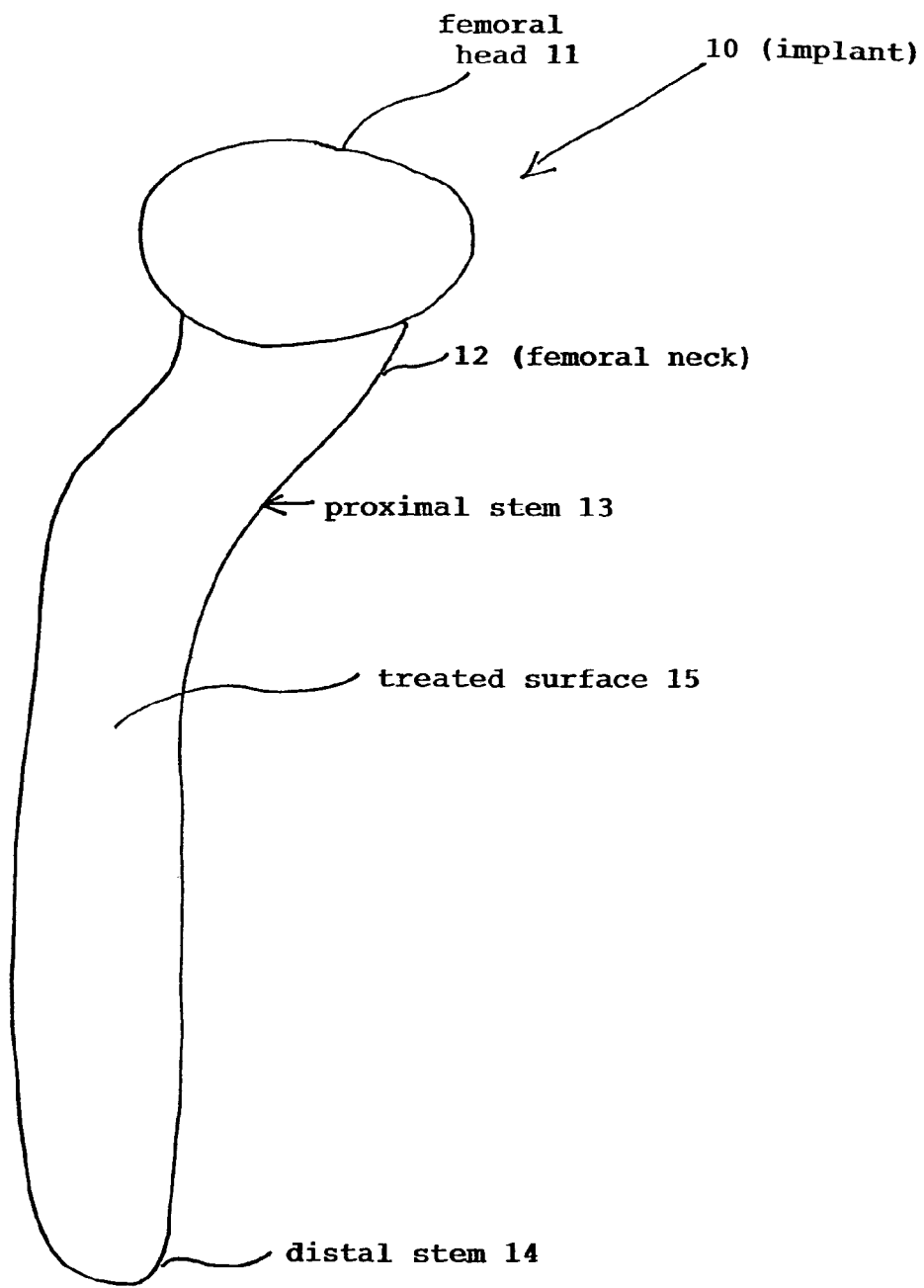
FIG. 1 is a front view of an implant 10 of the present invention with specific alloys of Ti, Al and Nb.

There are several advantages of using Ti-15Al-33Nb(at. %) and Ti-21Al-29Nb(at. %) alloys over other metals, metallic alloys (including Ti-6Al-4V(wt. %), and ceramics. The commonly used implant alloy is Ti-6Al-4V (wt. %) [i.e. "old method"] which contains the toxic element, vanadium. One main advantage of the alloys of the present invention is that Ti, Al and Nb are nontoxic elements. The mechanical properties of 15Al-33Nb(at. %) and Ti-21Al-29Nb(at. %) alloys in particular surpass the requirements for an implant material. Surgical implants require strength levels greater than that of bone and an elastic modulus close to that of bone. The yield strength of Ti-15Al-33Nb(at. %) and Ti-21Al-29Nb(at. %) alloys range between 800-1200 MPa, whereas bone has an ultimate strength of 83-117 MPa. High yield strength is critical in applications such as hip prostheses, where the weight of the body is supported on this highly stresses point. Bone must bend without breaking and this is where the modulus of Ti-015Al-33Nb(at. %) and Ti-21Al-29Nb(at. %) alloys is important. As the modulus of Ti-15Al-33Nb(at. %) and Ti-21Al-29Nb(at. %) alloys implant alloys is about half that for stainless steel and Co—Cr—Mo alloys, it is much more appropriate for use. The density of Ti implant alloys is also about half that of the stainless steel and Co—Cr—Mo alloys and this is especially important to older individual and people with frail builds such as children. A lightweight yet strong implant improves the recipient's comfort and ability to function. Ti-15Al-33Nb(at. %) and Ti-21Al-29Nb(at. %) alloys are resistant to general corrosion, pitting attack, and crevice corrosion, which occurs for several other metallic alloy systems as a result of attack from aggressive organic fluids. Other advantages of Ti-15Al-33Nb(at. %) and Ti-21Al-29Nb(at. %) alloys are that Ti is one of the most abundant minerals in the earth's crust, and it is affordable with the cost of Ti constantly dropping due to its demand in a large number of markets, including the aerospace and sports and recreational industries. Thousands of implants are manufactured and input into human patients annually, thus a large market is expected for the present invention.

Examples for Tensile and Fatigue Evaluation of Ti-15Al-33Nb(at. %) AND Ti-21Al-29Nb(at. %) Alloys Particularly for Biomedical Applications In these Examples, the fatigue and tensile behavior of Ti-15Al-33Nb(at. %) and Ti-21Al-29Nb(at. %) were evaluated and compared to that for other titanium-based biomedical implant alloys, in particular Ti-6Al-4V(wt. %). The mechanical properties of interest were fatigue strength, tensile strength, elastic modulus, and elongation-to-failure. Fatigue stress versus life curves were obtained for tests performed at room temperature in air as well as in Ringer's solution at R=0.1 for maximum stresses between 35%-90% of the ultimate tensile strength. The results indicated that the fatigue strength and lives and elastic modulus of these alloys is comparable to that for Ti-6Al-4V(wt. %). Considering the data scatter and deformation behavior, the Ringer's solution did not significantly affect the fatigue behavior. Heat treatment reduced the tensile strength and this corresponded to a reduction in the fatigue strength. The tensile strength of the as-processed alloys was slightly lower than that for Ti-6Al-4V(wt. %), and the Ti-15Al-33Nb(at. %) exhibited lower strengths and higher elongations than Ti-21Al-29Nb. Based on the current results, these titanium-aluminum-niobium alloys are useful for biomedical applications.

In the current invention, Ti—Al—Nb alloys containing lower Ti concentrations, in particular Ti~50 at. %, were evaluated to determine their attractiveness for biomedical implant applications. It was necessary to evaluate various mechanical properties of such alloys for such applications. Fatigue strength is one of the most important mechanical parameters which are needed in order to assess the reliability of a material in medical implant application as an implant has to withstand not only one-time peak stresses, but also several million load cycles which it usually experiences during its lifetime. In this regard, the fatigue behavior, tensile strength, and elastic modulus of Ti-21Al-29Nb and Ti-15Al-33Nb (at. %), were evaluated and compared to those for other Ti biomedical alloys.

Experimental Procedures

Materials and Processing

Titanium, aluminum, and niobium master alloys were mixed to produce nominally Ti-17Al-33Nb(at. %) and Ti-22Al-28Nb(at. %) compositions, and then double vacuum arc remelted in a vacuum furnace (preferably at 1400 to 1800° C.). The melts were cast into 15 cm diameter ingots (weighing 27 kg), which were then multistep forged to approximately 14 cm by 7 cm by 58 cm. Approximately 1.6 cm thick slabs were then cut from the transverse sections of the ingots and hot rolled (preferably 800 to 999° C.) to 1.65 mm thick by 7 cm wide sheets. The hot rolling produced a reduction in area of 90% and introduced a total effective true shear strain on the order of two. Identical hot-working temperatures, which were always maintained below the body center cubic (BCC) phase transus temperature, were used for the forging and rolling operations for a given material. The Ti-17Al-33Nb (at. %) sheets were hot rolled at 899° C. and the Ti-22Al-28Nb(at. %) sheets were hot rolled at 982° C. After the hot rolling was complete, the sheets were annealed at their respective rolling temperatures for one hour and then air-cooled. All alloy processing was performed by RMI Titanium Company, Niles, Ohio. The chemical compositions of the rolled sheets, listed in Table 1, were determined using Inductively Coupled Plasma Optical Emission Spectroscopy (ICP-OES) and Inert Gas Fluorescence (IGF).

TABLE 1

| Alloy | Alloy compositions | | | | | |
|---|---|---|---|---|---|---|
| | Ti, at % | Al, at % | Nb, at % | Fe, ppm | O, ppm | N, ppm |
| Ti—15Al—33Nb | 51.4 | 15.3 | 33.3 | 110 | 1100 | 100 |
| Ti—21Al—29Nb | 50.7 | 20.6 | 28.7 | 2000 | 790 | 110 |

From Table 1, it was apparent that the alloys more closely resembled Ti-15Al-33Nb (at. %) and Ti-21Al-29Nb(at. %)1, and therefore, they are referred to as this composition throughout the Examples. Henceforth, the alloys will be referred to as Ti-21Al-29 Nb and Ti-15Al-33Nb. The samples were evaluated both in the as-processed (AP) condition as well as after the following heat treatment performed in flowing argon: 1005° C./3h/FC at 10° C. per minute to 855° C./8h/CC at 1° C./minute to 650° C. then furnace cooled (FC) to room temperature (RT)). A schematic illustrating this heat treatment schedule is given in FIG. 2.

Tensile and Fatigue Tests

Figure 2:
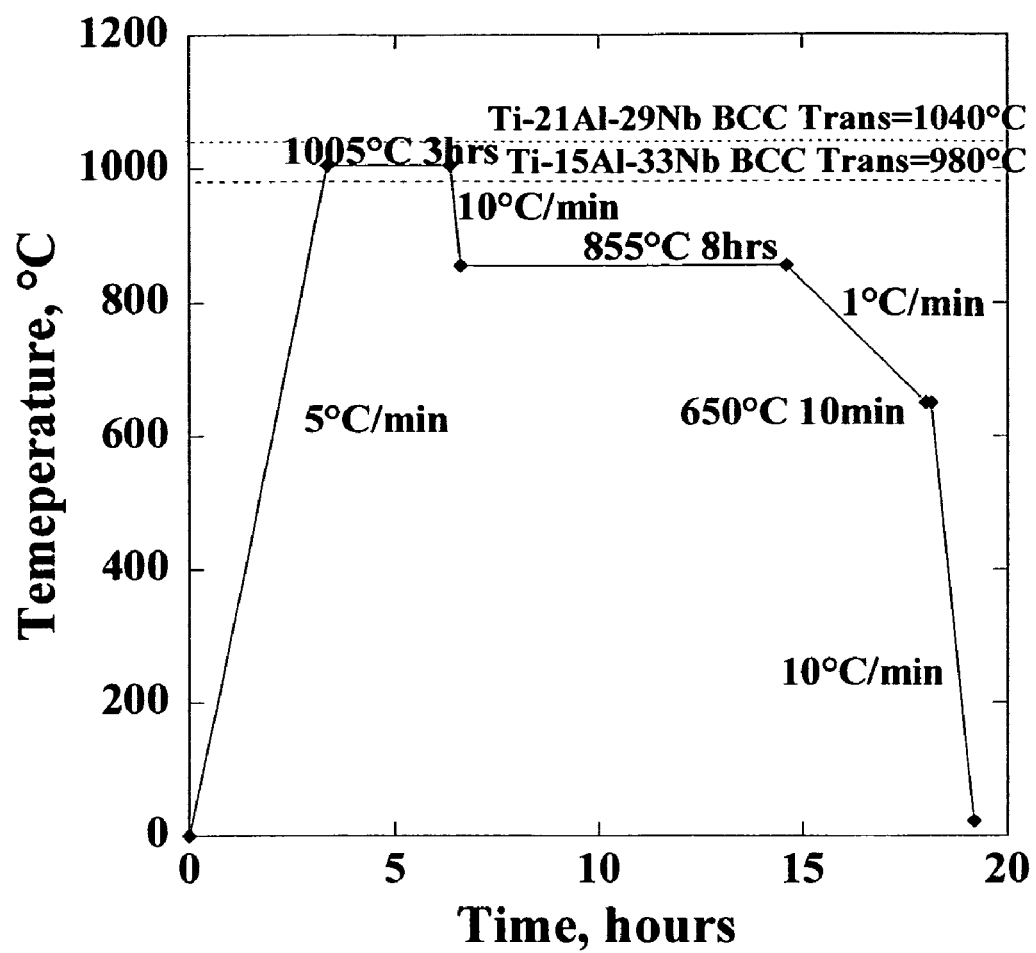
FIG. 2 is a graph showing a schematic of the heat-treatment schedule used on the processed alloys. Note that 1005° C. is above the BCC transus for ti-15Al-33Nb and below the BCC transus for Ti-21Al-29Nb.
Figure 3:
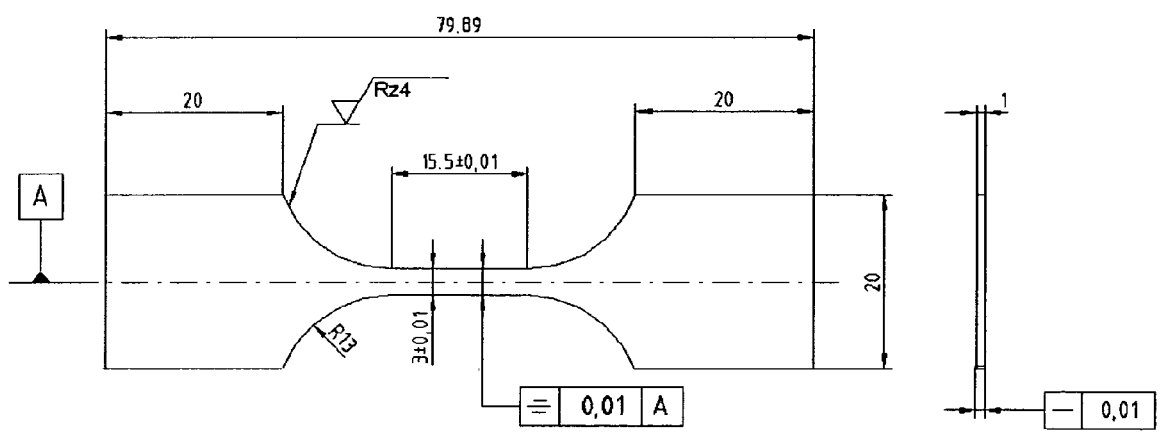
FIG. 3 is a plan view of the fatigue specimen geometry used. All values are given in millimeters.

Flat dogbone-shaped specimens were machined from the as-processed sheets with their longitudinal directions parallel to the rolling direction. The geometry of the fatigue test specimen, which is identical to that used for other investigations of biomedical Ti alloys (N. al Saffar and P.A. Revell: Br. J. Rheumatol 33 (1994), pages 309-316), is depicted in FIG. 2. Larger specimens, containing a gage section width of 13 mm and a gage length of 50 mm, were used for the tensile experiments. All the machined specimens were polished using a sequentially finer grits of silicon carbide (SiC) paper with a final polish using 0.06 μm colloidal silica to produce mirror surfaces.

Tensile tests were carried out on the specimens using an Instron 8562 test frame in air at 295K using a strain rate of $1.3\times10^{-3}s^{-1}$. The strain was measured using an extensometer attached to the gage section of the specimen. The average ultimate tensile stress (UTS), yield stress (0.2% YS), and elongation-to-failure ($\epsilon_f$) values were recorded for multiple samples tested in each condition. Young's modulus (E) for each sample was determined from the slope of the elastic portion of the stress versus strain curves.

Figure 4:
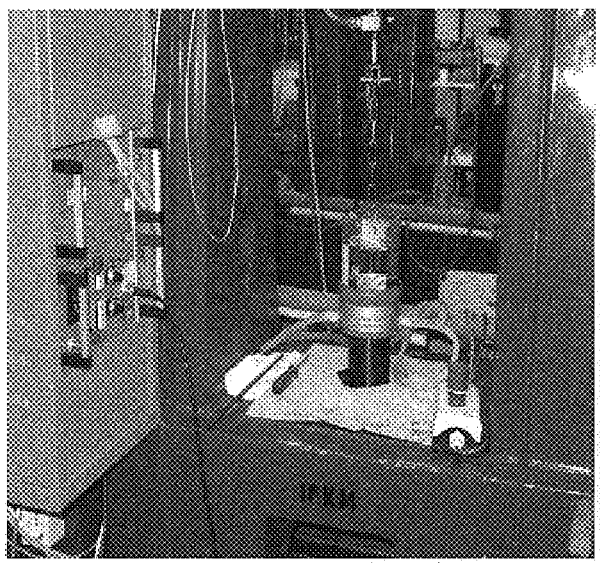
FIGS. 4 and 4A are photographs of the fatigue set-up. A pulsating sinusoidal load (tension-tension mode) was used for the tests which were performed in a Ringer's solution bath according to DIN 58840 at 37° C. Selected experiments were also performed in air at RT.
Figure 4A:
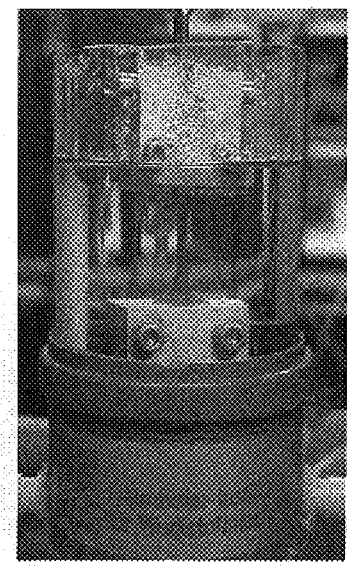

Fatigue tests were carried out at two institutions using two different test apparatuses. In each case, the fatigue testing was performed at a frequency of 10 Hz with a stress ratio of R=0.1 under a tension-tension stress mode in air at 295K. The fatigue experiments performed at Toyohashi University of Technology, Japan, used an electro-servo-hydraulic fatigue-testing machine (N. al Saffar, Ibid). The maximum applied stresses ranged between 820-950 MPa ($\geqq0.86$UTS) and $1\times10^7$ cycles were considered to be "run out" whereafter the unfractured sample was removed. Typically, more than one sample was tested in each condition, and such samples were polished through 0.06 μm colloidal silica in order to identify surface deformation through scanning-electron microscopy (SEM) observations of post-tested specimens. The fatigue experiments performed at the Fraunhofer Institute for Mechanics of Materials, Freiburg Germany, used servo-hydraulic testing machines with a chain assembly and stainless steel grips in order to avoid transverse stresses as depicted in FIG. 4. In this case, the maximum stresses ranged between 350-750 MPa (0.35-0.75UTS). In addition to testing in air at RT, samples were tested in Ringer's solution (37° C.) in order to obtain insight into the fatigue behavior under physiological conditions. Due to the significant fatigue data scatter, up to five specimens were tested for each stress level chosen. For such testing, $2\times10^6$ cycles was considered to be run out, and all the samples which experienced run out were removed from the machine and subsequently examined in RT tensile experiments, identical to those described previously, in order to characterize strength loss due to fatigue. The fracture surfaces of both the tensile and fatigue specimens were evaluated using SEM.

Microstructural Characterization

Characterization of the microstructures was carried out using optical microscopy (OM), SEM, and X-ray diffraction (XRD) analysis. Samples were mounted in Konductomet™ (made by Buehler; Lake Bluff, Ill.) then ground using successively finer grits of SiC paper. After grinding, the samples were polished using diamond paste, according to the following schedule: 30 μm for 5 minutes, 15 μm for 5 minutes, 6 μm for 5 minutes, 1 μm for 20 minutes. Colloidal silica with an average particle size of 0.06 μm was used for the final polish, with polishing times ranging between 20 minutes to 2 hours. For the OM observations, after mirror finishing, each specimen was etched using a standard 75 ml $H_2O$-20 ml HF-5 ml $HNO_3$ etchant solution. High-contrast digitized backscattered-electron (BSE) SEM images, obtained using both an AMRAY 1810 SEM and Phillips 515 SEM (Boston, Mass.), were used for volume fraction analysis of the body-centered cubic (BCC), orthorhombic (O), and hexagonal close packed (HCP) α2 phases present. Approximately twenty BSE images were taken at different magnifications and from different sections of each sample. These images were then analyzed using NIH Image Analysis Software to measure the area fraction of the phases containing different contrast due to different chemical contents. By performing this analysis on several images from the different sheet orientations of the samples, the average volume fraction of each phase was determined.

Average equiaxed grain size was determined using the ASTM standard E112 (T. A. Blaine 1996, ibid). As with phase volume fraction determinations, several micrographs were taken at different magnifications from different sheet orientations for the grain size calculations. The grain size measurements were in good agreement with those based on the analysis from the electron backscattered diffraction (EBSD) orientation maps. The spatially resolved EBSD orientation maps were obtained using a Phillips 515 SEM with $LaB_6$ filament. The EBSD hardware and software were manufactured by EDAX-TSL, Inc. (Mahwah, N.J.). In order to remove the mechanically polished surface layer of the metallographically-prepared SEM samples, electropolishing was used by means of Struers TenuPol-5 (Westlake, Ohio) with a TETET adapter, which can polish an area of 10 mm diameter. The EBSD samples were electropolished in 6% $H_2SO_4$ methanol solution at −40° C. using 70V for approximately one minute. XRD analysis was performed using a Cu Kα source with an accelerating voltage of 40 kV and a current of 30 mA.

Results and Discussion

Microstructure

Table 2 lists the measured phase volume fractions and grain sizes for the microstructures evaluated.

TABLE 2

Average phase volume fractions and grain size.

| Alloy | Heat Treatment, ° C. | $\alpha_2$ Vol. Fraction | O Vol. Fraction | BCC Vol. Fraction | Grain Size*, μm |
|---|---|---|---|---|---|
| Ti—15Al—33Nb | AP | 10 | 0 | 90 | 3 |
| Ti—15Al—33Nb | 1005° C. | 1 | 44 | 55 | 120** |
| Ti—21Al—29Nb | AP | 4 | 0 | 96 | 3 |
| Ti—21Al—29Nb | 1005° C. | 5 | 78 | 17 | 12 |

*Measured independent of phase except in the case of ** where the grain size represented the prior-BCC grain size for this supertransus heat-treated sample.

Figure 5A:
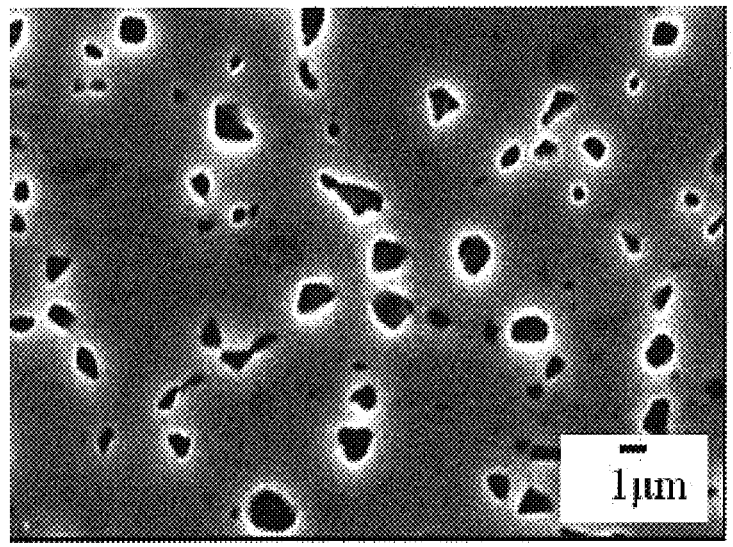
FIG. 5A is a SEM image.
Figure 5B:
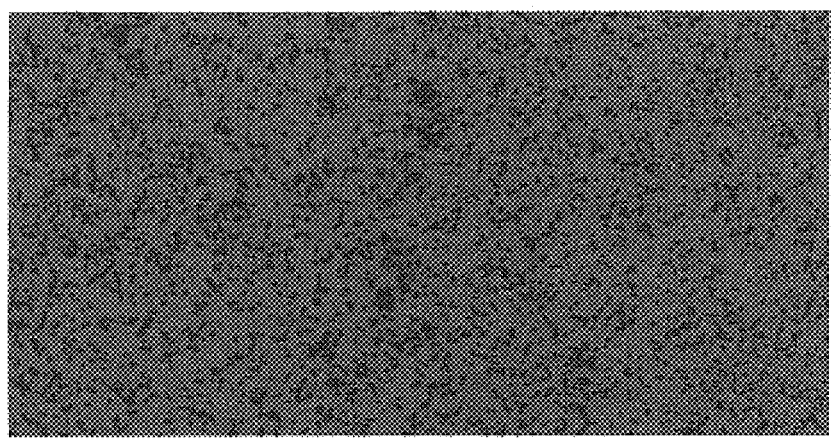
FIG. 5B is a EBSD phase map where green is the B2 phase and red is either the O or $\alpha_2$ phase.
Figure 5C:
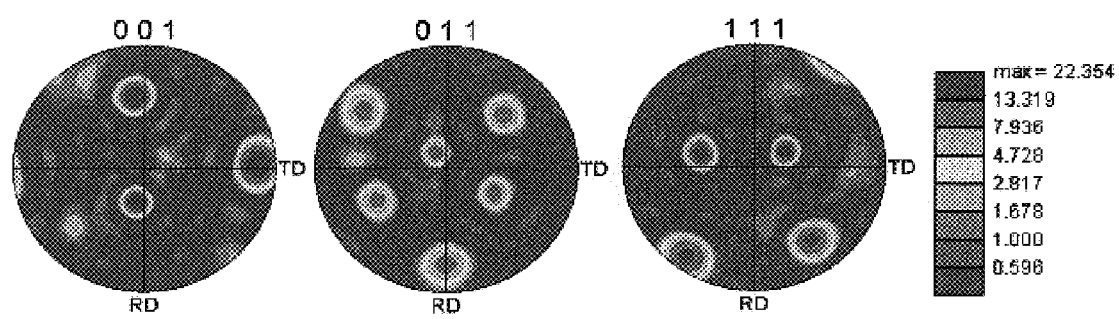
FIG. 5C is a (001, (011), and (111) B2-phase pole figures for the as-processed Ti-21Al-29Nb microstructure.
Figure 6A:
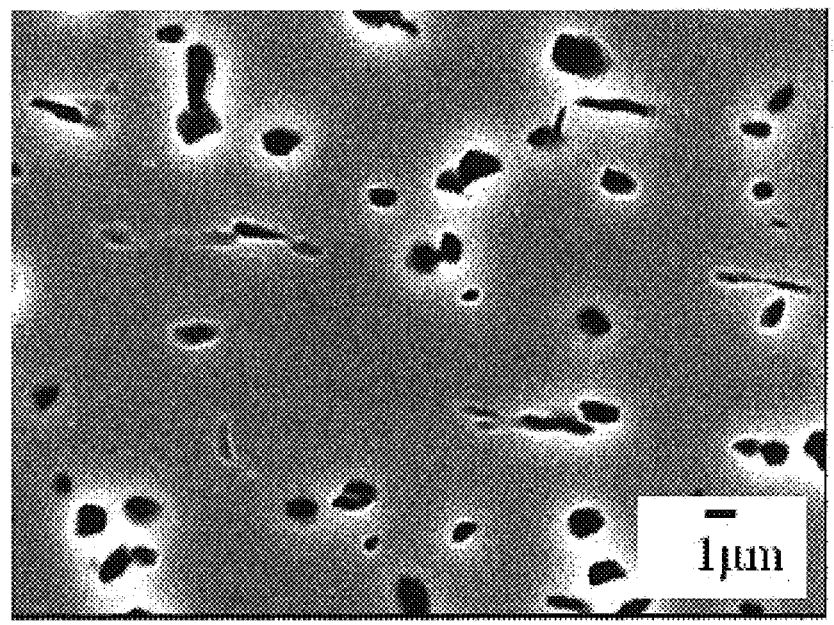
FIG. 6A is a SEM image.
Figure 6B:
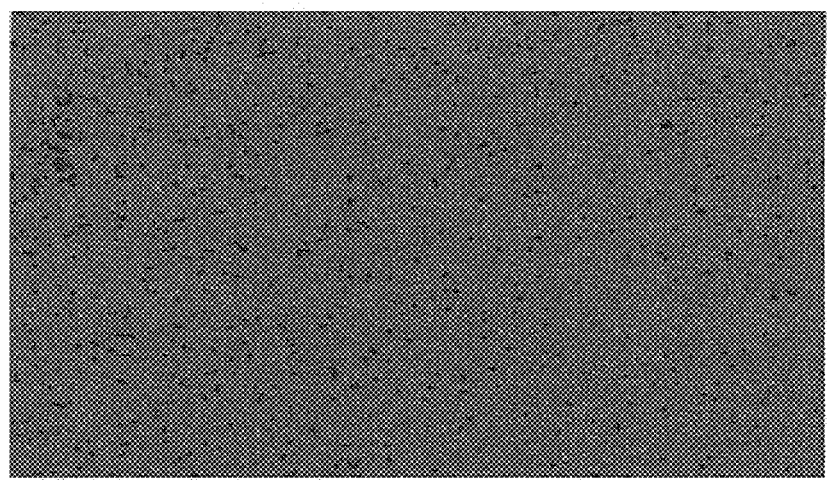
FIG. 6B is a EBSD phase map where green is the β phase and-red is either the O or $\alpha_2$ phase.
Figure 6C:
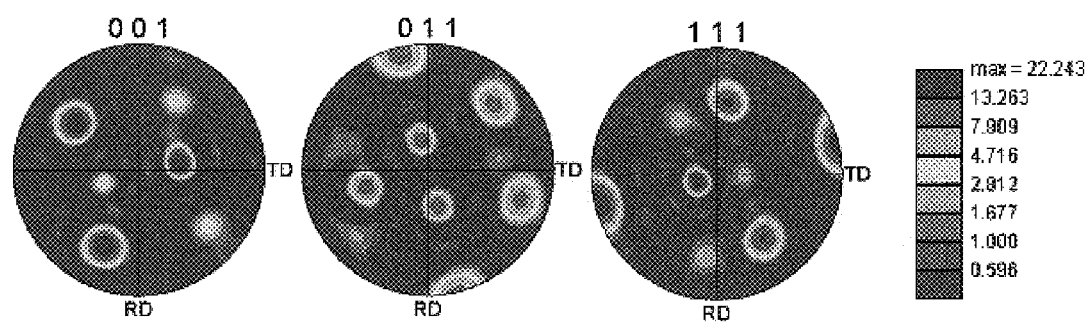
FIG. 6C is (001), (011) and (111) β-phase pole figures for the as-processed Ti-15Al-33Nb microstructure.
Figure 7A:
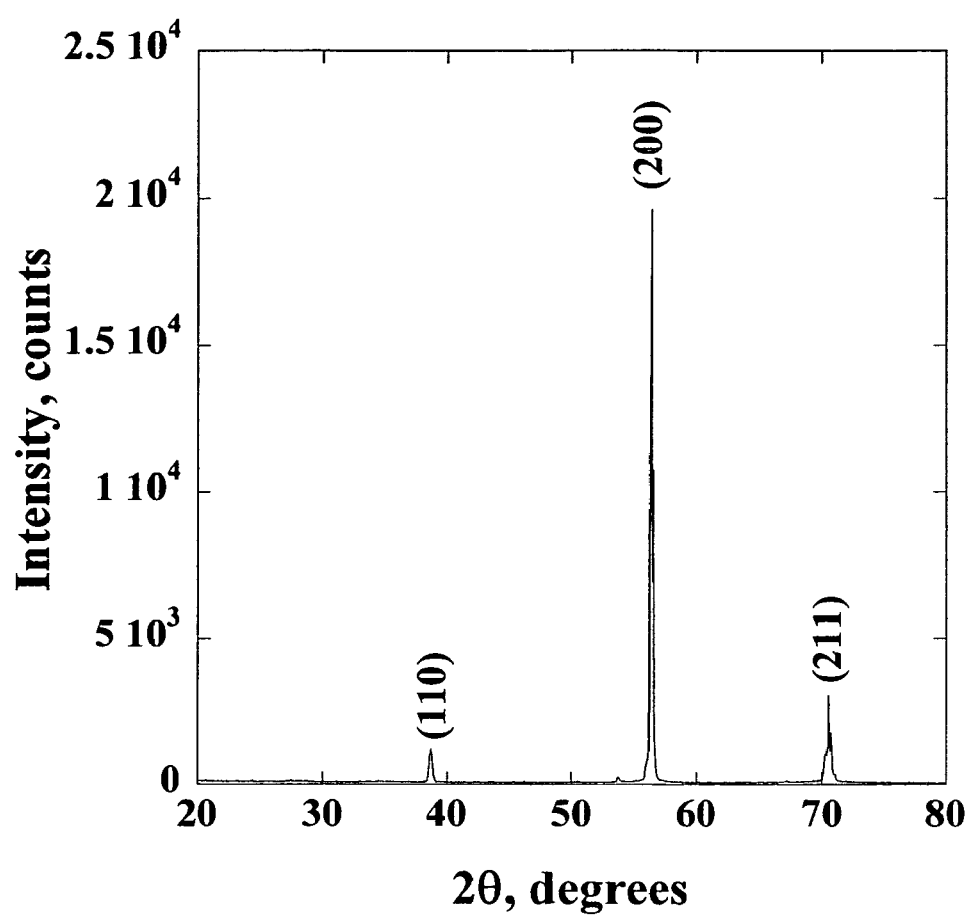
FIGS. 7A and 7B are XRD plots of intensity versus 2θ for Ti-15Al-33Nb (HT: 1075° C./3h/WQ) (FIG. 7A—20-80° 2θ scan and (b) 60-65 ° 2θ long-count-time scan. The lack of a (210) peak in FIG. 7B indicates the BCC phase was disordered (β).
Figure 7B:
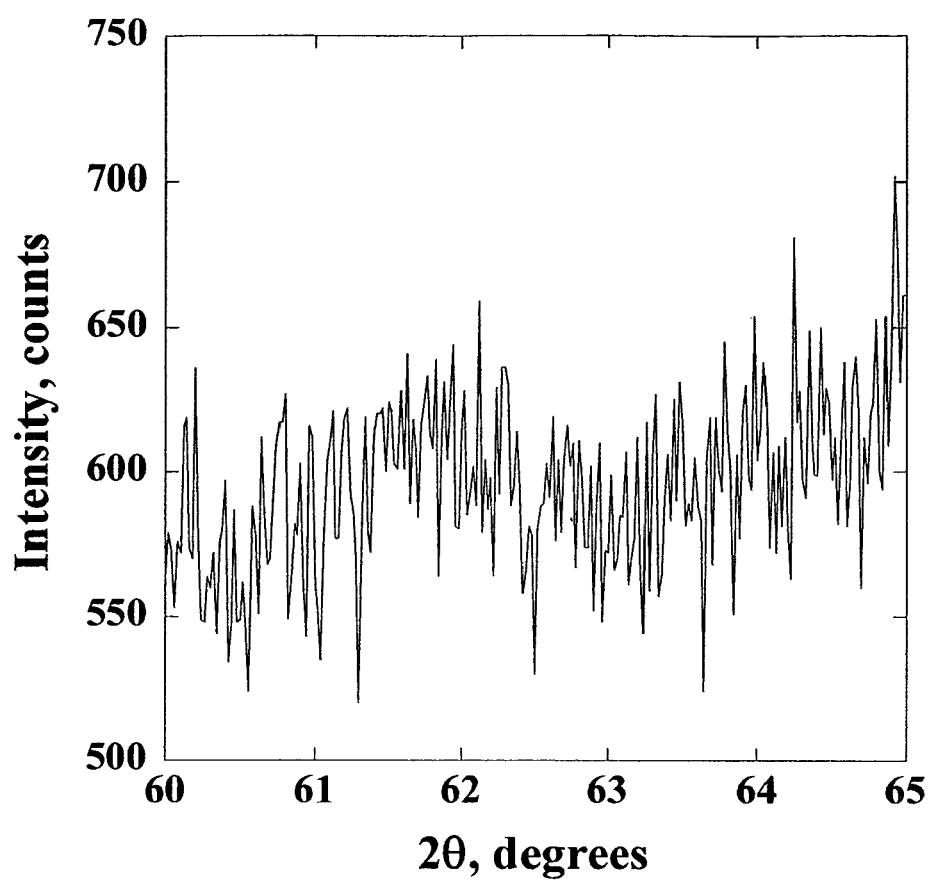
Figure 8A:
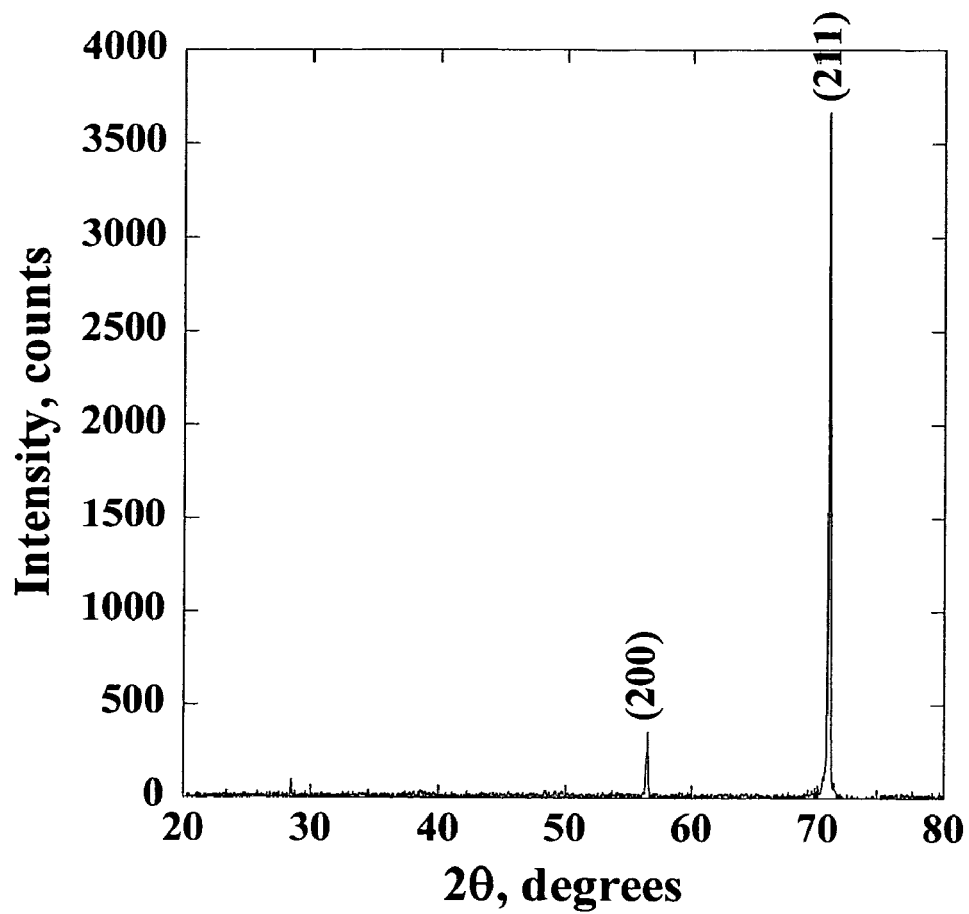
FIGS. 8A and 8B are XRD plots of intensity versus 2θ for Ti-15Al-33Nb (HT: 1075° C./3h/WQ) (FIG. 8A—20-80° 2θ scan and (b) 60-65° 2θ long-count-time scan. The presence of a (210) peak in FIG. 8B indicates the BCC phase was ordered (B2).
Figure 8B:
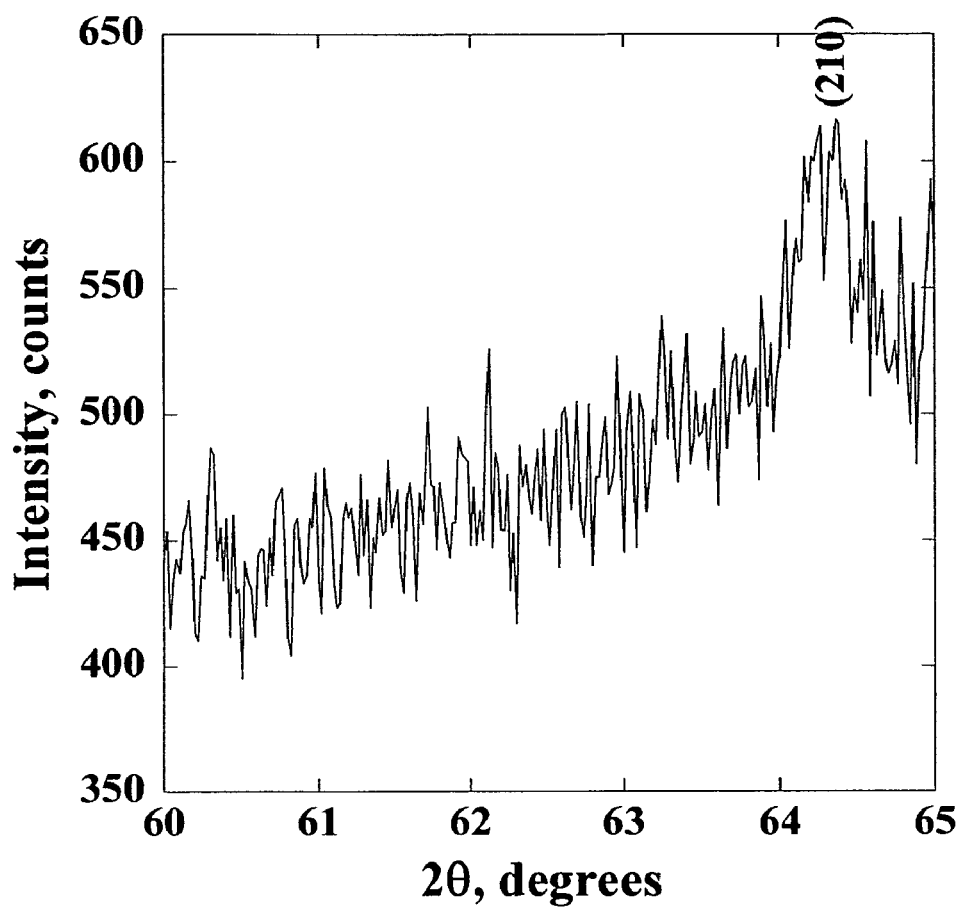
Figure 9A:
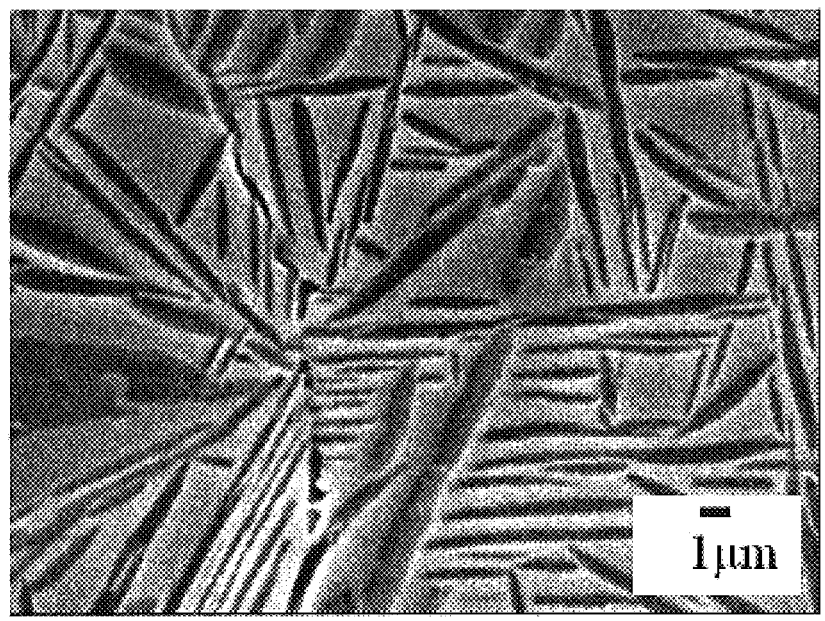
FIG. 9A is a BSD SEM image.
Figure 9B:
FIG. 9B is a EBSD phase map where green is the B2 phase and red is either the O or $\alpha_2$ phase.
Figure 9C:
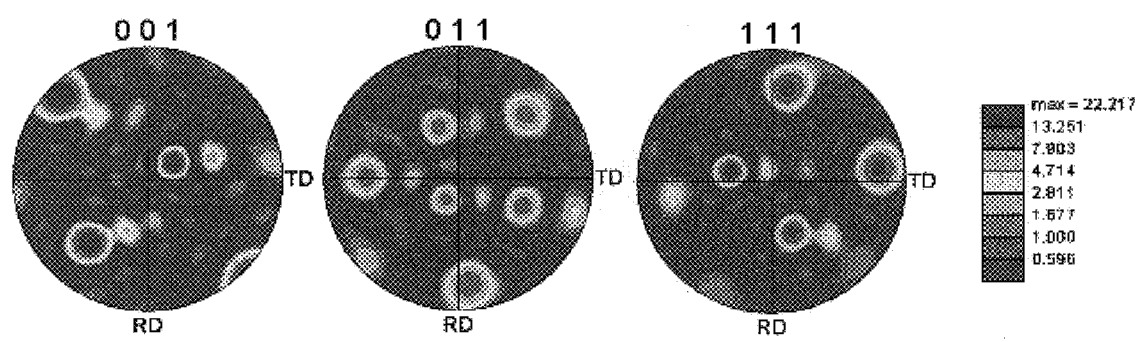
FIG. 9C is a (001), (011) and (111) B2-phase pole figures for the heat-treated Ti-21Al-29Nb microstructure.
Figure 10A:
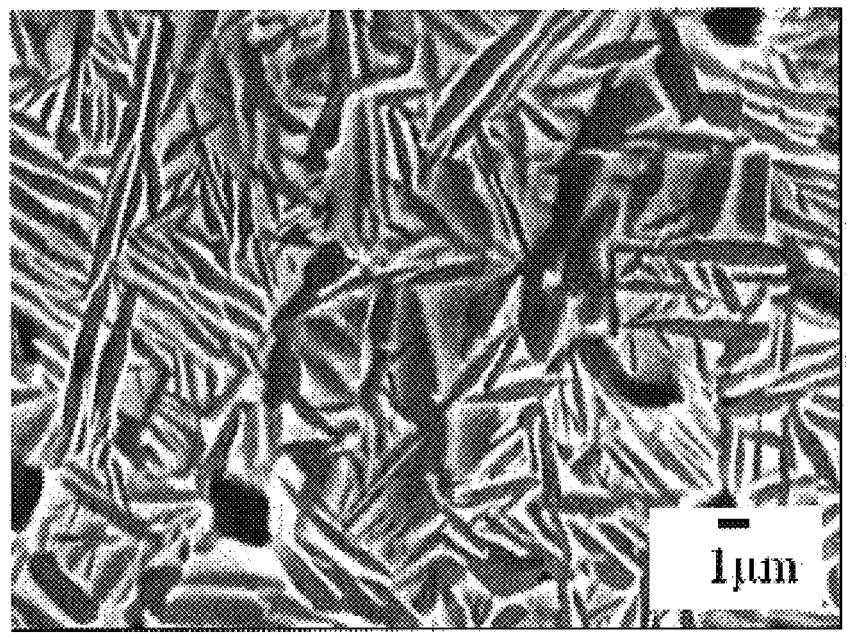
FIG. 10A is a BSD SEM image.
Figure 10B:
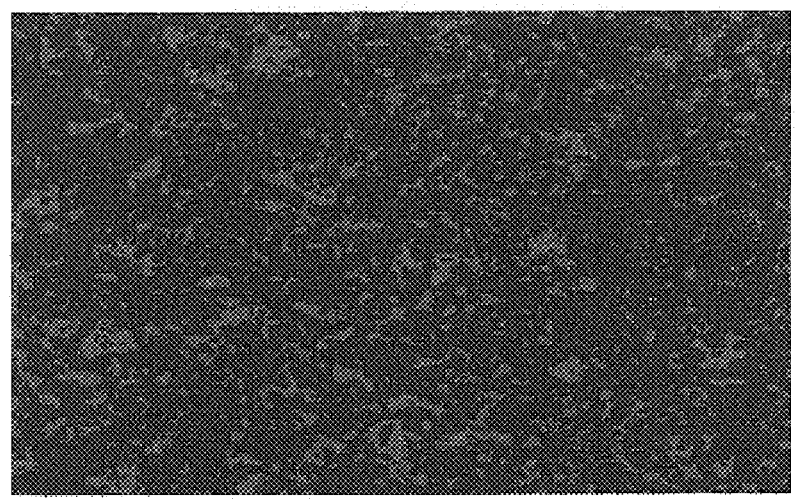
FIG. 10B is a EBSD phase map where green is the β phase and red is either the O or $\alpha_2$ phase.
Figure 10C:
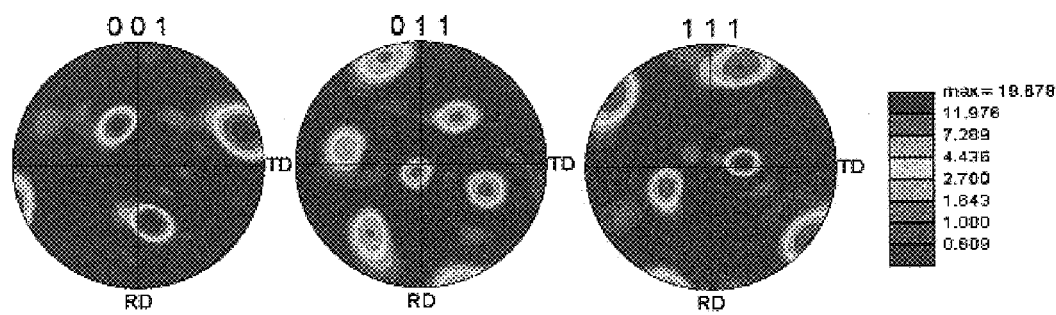
FIG. 10C is a (001), (011) and (111) β-phase pole figures for the heat-treated Ti-15Al-33Nb microstructure.

SEM images and EBSD phase maps of the as-processed Ti-21Al-29Nb and Ti-15Al-33Nb microstructures are shown in FIGS. 5A and 5B and 6A and 6B. Each of the as-processed microstructures was somewhat textured as illustrated in FIGS. 5C and 6C. XRD observations on super-transus solutionized and water-quenched microstructures indicated that the BCC phase in Ti-21Al-29Nb was ordered (B2) and it was disordered (β) in Ti-15Al-33Nb, see FIGS. 7A and 7B and 8A and 8B (note the super lattice (210) reflection in FIG. 8B). Combining the NIH image analysis with the EBSD analysis, it is evident that the as-processed alloys were composed almost entirely of the BCC phase, see Table 1. SEM images and EBSD phase maps of the heat-treated Ti-21Al-29Nb and Ti-15Al-33Nb microstructures are shown in FIGS. 9A and 9B and 10A and 10B. The heat-treatments resulted in greater overall grain sizes, greater volume fractions of the O phase, and lower volume fractions of the BCC phase. In addition the BCC phase was not as strongly textured, see FIGS. 9C and 10C, indicating that some recrystallization likely occurred during the heat treatment.

Tensile Behavior

Figure 11:
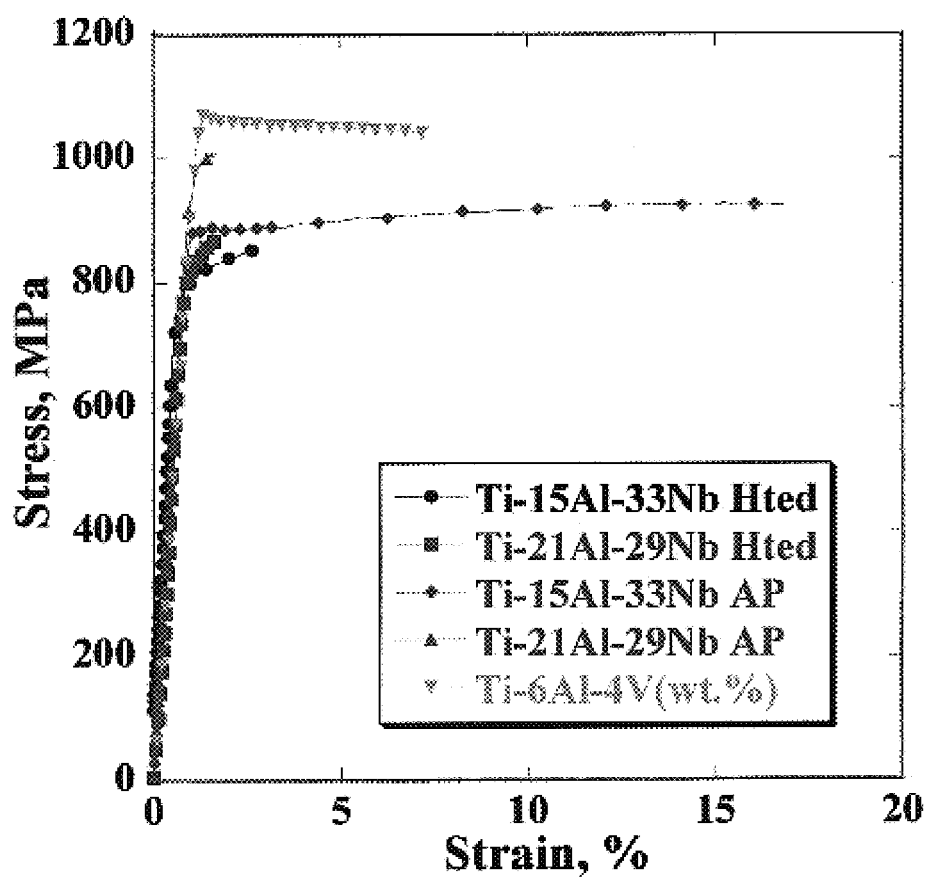
FIG. 11 shows RT tensile stress versus strain curves for the as-processed and heat-treated (Hted) Ti-21Al -29Nb and Ti-15Al-33Nb alloys along with tensile data for Ti -6Al-4V (wt. %).
Figure 12A:
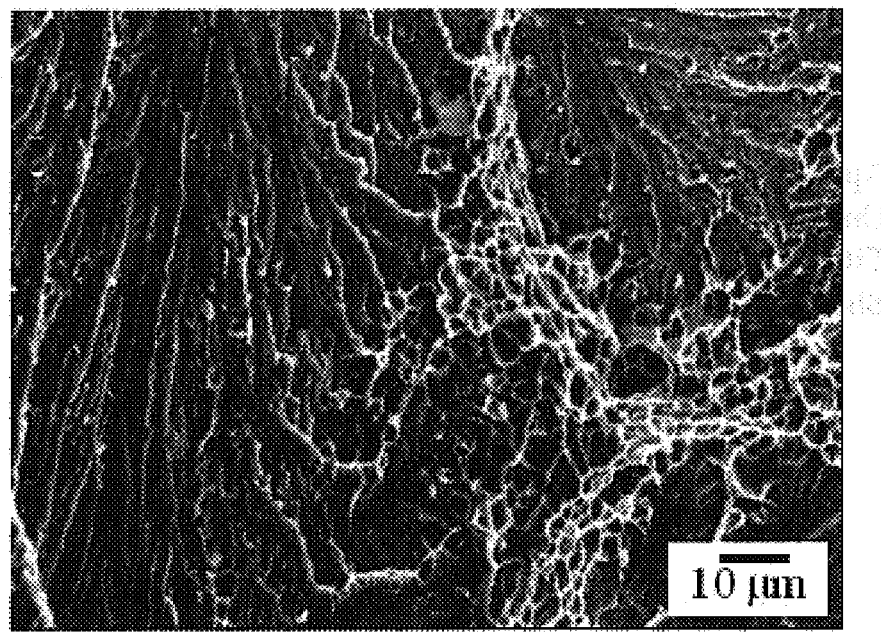
FIGS. 12A and 12B are SEM images of the fracture surfaces of the RT tensile tested Ti-21Al-29Nb.
Figure 12B:
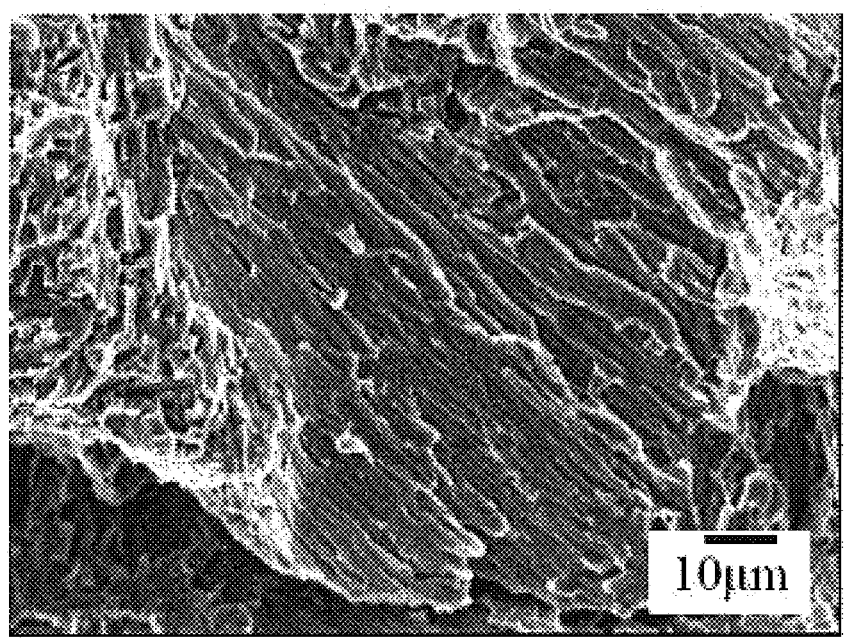
Figure 13A:
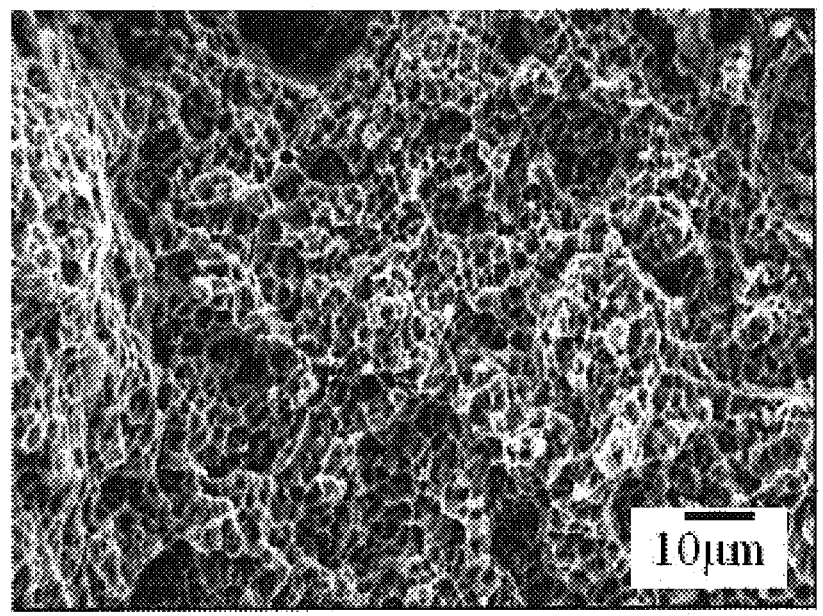
FIGS. 13A and 13B are SEM images of the fracture surfaces of the RT tensile tested Ti-15Al-33Nb.
Figure 13B:
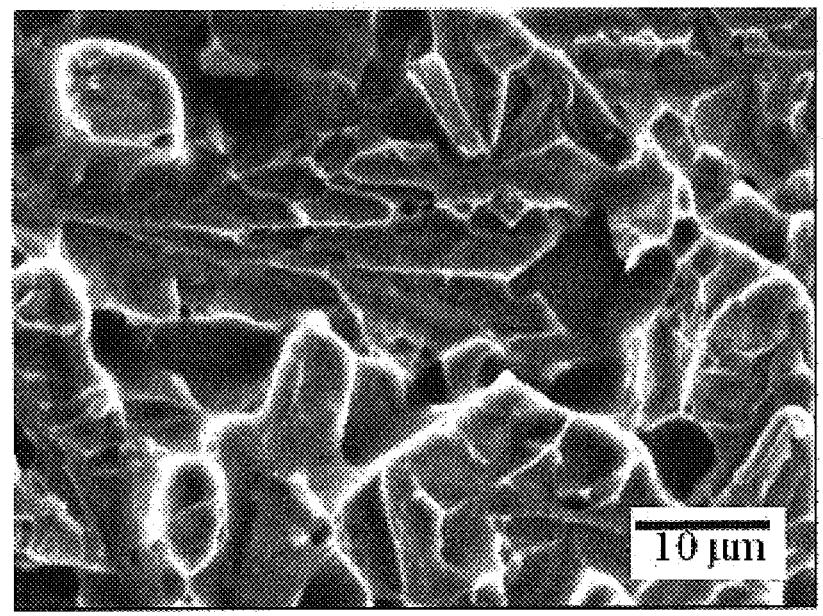

Representative RT tensile stress versus strain plots of each of the alloys is shown in FIG. 11 along with those for Ti-6Al-4V sheet material. The average UTS, 0.2% YS, and $N_f$ values of the as-processed alloys were 1010 MPa, 972 MPa, and 1.7% for Ti-21Al-29Nb and 916 MPa, 876 MPa, and 12.4% for Ti-15Al-33Nb. Thus, the tensile strength of Ti-21Al-29Nb was greater than that for Ti-15Al-33Nb however it exhibited poorer processability and lower $N_f$ values. The heat treatments lowered both the strength and the $N_f$ in both alloys, see FIG. 11 and Table 3. Since greater O-phase volume fractions tend to lead to lower $N_f$ values (K. Kobayashi, 2000, ibid), this result is not unexpected. It is noted that some ductile behavior is observed for Ti-15Al-33Nb as the average $N_f$ value for the heat-treated samples was 2.1% and the fracture surfaces exhibited ductile dimpling. As a result, Ti-15Al-33Nb alloy is considered to have exhibited a better balance of RT strength and elongation, while Ti-21Al-29Nb exhibited a greater strength due mainly to the higher Al content. The fracture surfaces of the as-processed and heat-treated samples, illustrated in FIGS. 12A and 12B and 13A and 13B, exhibited the ductile and brittle features of the alloys. The Ti-6Al-4V(wt. %) sheet exhibited a slightly higher strength than Ti-21Al-29Nb and an average $N_f$ less than that for the as-processed Ti-15Al-33Nb.

The average E values ranged between 94-111 GPa for Ti-15Al-33Nb and 103-115 GPa for Ti-21Al-29Nb. The E data followed the observed trend that greater volume fractions of BCC phase tend to reduce E for O+BCC alloys and in particular the disordered β phase is less rigid than ordered B2. It is noted that order in the BCC structures is dependent on Al content where above 17Al, the disordered β structure tends to order into the B2 structure (E. M. Schwarz (1998) ibid and K. D. Merkel (1999), ibid). The E value for Ti-6Al-4V(wt. %) was 110 GPa. Thus, E was similar for the Ti—Al—Nb alloys compared to the α+β Ti-6Al-4V(wt. %). In both cases, the E values were significantly greater than that for other α alloys (E<65 GPa) recently targeted for biomedical applications (N. al Saffar (1994), ibid)

Fatigue Behavior

Figure 14A:
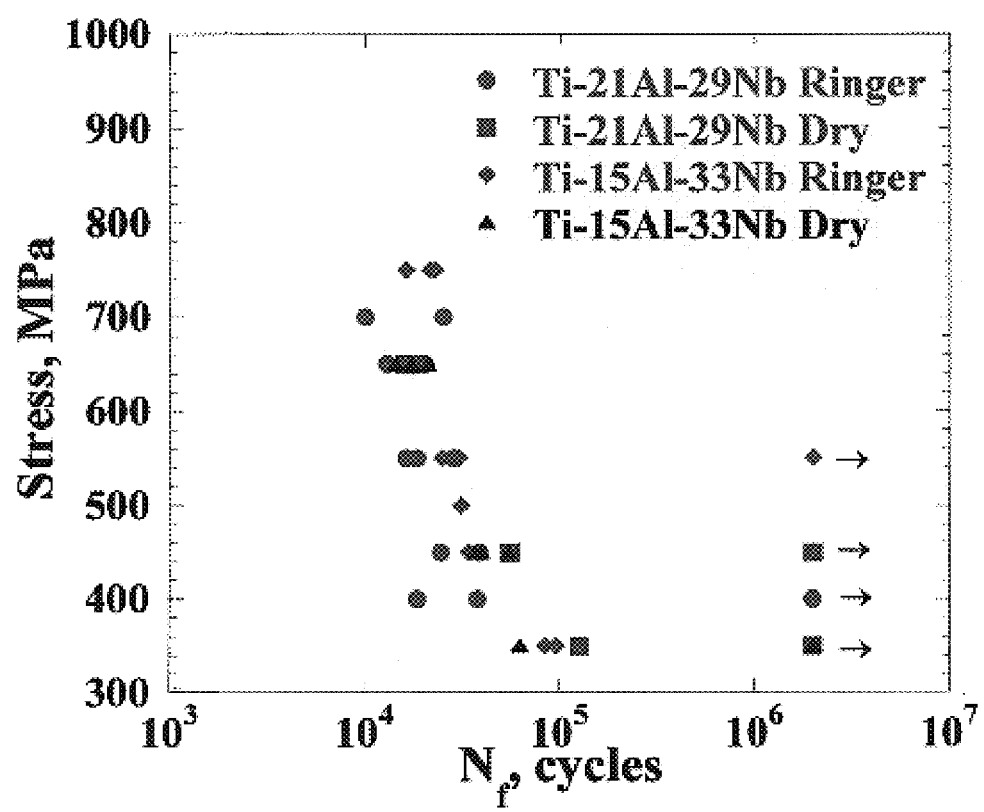
FIGS. 14A and 14B show maximum applied stress versus fatigue life.

The S—N curves for the as-processed alloys tested by the Fraunhofer Institute are illustrated in FIG. 14A. Considering the 95% confidence band for the fatigue live values, determined according to the ASTM E 739-80 standard (Y. H. Kim et al (1999), ibid), one alloy was not clearly superior to another and the Ringer's solution did not have a significant effect on the fatigue lives. Run-out samples were noted for both alloys at maximum stresses of 350-450 MPa, and one Ti-15Al-33Nb sample tested in Ringer's solution at 550 MPa maximum stress also exhibited run out. Although we did not observe a fatigue limit based on our data (i.e. there were failures even at the lowest maximum stress of 350 MPa), we expect it to be close to 350 MPa as the majority of the samples tested at this maximum stress level exhibited run out.

Figure 14B:
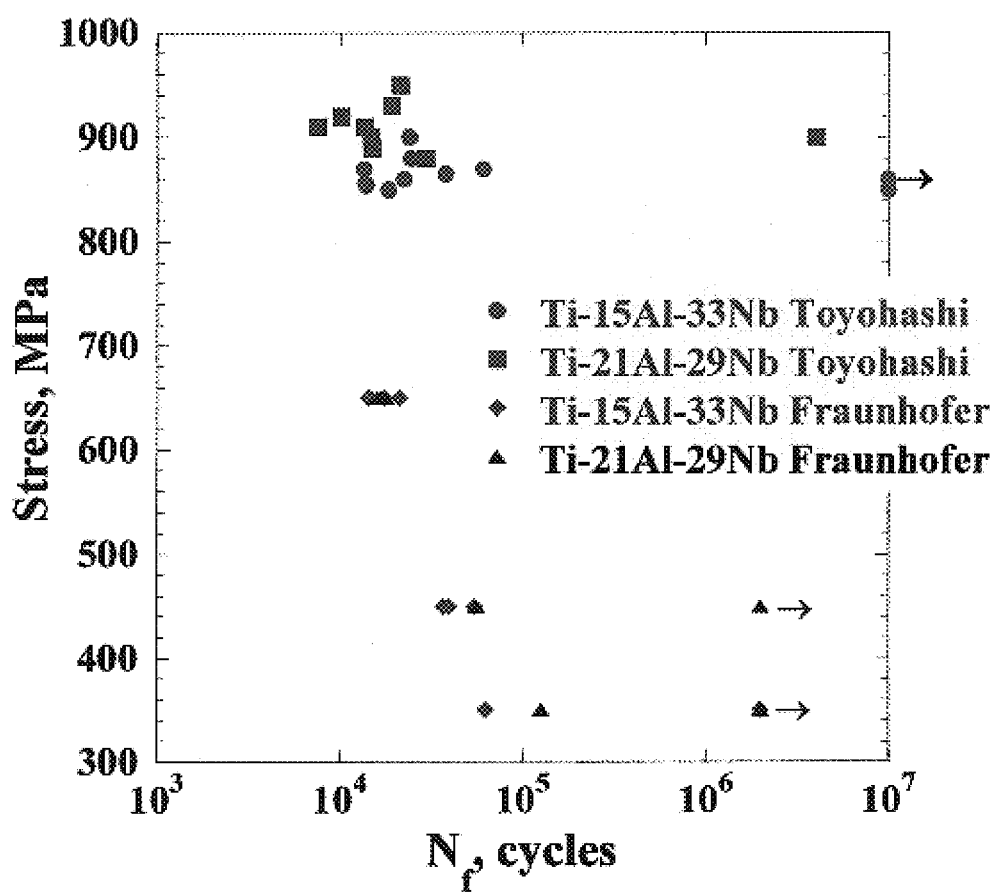

The S—N curves of all the as-processed alloy samples tested in air at RT are provided in FIG. 14B. The two (2) institutions tested the specimens in different stress regimes; i.e. all the Fraunhofer Institute data was obtained at σ<750 MPa while all the Toyohashi University of Technology data was obtained at σ>820 MPa, see Table 4.

TABLE 4

Fatigue Lives in Number of Cycles for all the Tested Samples.

| Maximum Cyclic Stress, MPa | AP Ti—15Al—33Nb Dry | AP Ti—15Al—33Nb Ringer | AP Ti—21Al—29Nb Dry | AP Ti—21Al—29Nb Ringer | Hted Ti—15Al—33Nb Dry | Hted Ti—21Al—29Nb Dry |
|---|---|---|---|---|---|---|
| 350 | 62680 | 84200 | 126230 | 2000000* | | |
|  | 2000000* | 96250 | 2000000* | 2000000* | | |
|  | 2000000* | 2000000* | 2000000* | | | |
| 400 | | | | 18600 | | |
|  | | | | 38060 | | |
|  | | | | 2000000* | | |
| 450 | 36950 | 34330 | 55350 | 24670 | | |
|  | 39500 | 2000000* | 55980 | 39200 | | |
|  | 54680 | 2000000* | 2000000* | 2000000* | | |
| 500 | | 31300 | | | | |
| 550 | | 24850 | | 16300 | | |
|  | | 30270 | | 18530 | | |
|  | | 2000000* | | 28320 | | |
| 650 | 14301 | 17150 | 15890 | 12950 | | |
|  | 17296 | 18270 | 16510 | 19130 | | |
|  | 21081 | 20330 | 17760 | 20130 | | |
| 700 | | | | 10000 | 10000000* | 10000000* |
|  | | | | 25180 | | |
| 750 | | 16220 | | | 8643185 | 10000000* |
|  | | 21360 | | | | |
|  | | 22720 | | | | |
| 820 | | | | | 13705 | |
| 840 | | | | | 21996 | |

TABLE 4-continued

Fatigue Lives in Number of Cycles for all the Tested Samples.

| Maximum Cyclic Stress, MPa | AP Ti—15Al—33Nb Dry | AP Ti—15Al—33Nb Ringer | AP Ti—21Al—29Nb Dry | AP Ti—21Al—29Nb Ringer | Hted Ti—15Al—33Nb Dry | Hted Ti—21Al—29Nb Dry |
|---|---|---|---|---|---|---|
| 850 | 18376 | | | | | |
|  | 10000000* | | | | | |
| 855 | 13762 | | | | | |
| 860 | 22363 | | | | 30402 | |
|  | 10000000* | | | | | |
| 865 | 37973 | | | | | |
| 870 | 13472 | | | | 11183 | |
|  | 60662 | | | | | |
| 880 | 24449 | | 29270 | | 17076 | 6807 |
| 890 | | | 14963 | | | 1633 |
| 900 | 24037 | | 14808 | | 8956 | 2706 |
|  | | | 4010000 | | | |
| 910 | | | 7549 | | | |
|  | | | 13481 | | | |
| 920 | | | 10130 | | | 6933 |
| 930 | | | 19087 | | | |
| 940 | | | | | | 3282 |
| 950 | | | 21395 | | | |

AP: as processed;
Hted: heat treated;
*run-out samples

Figure 15A:
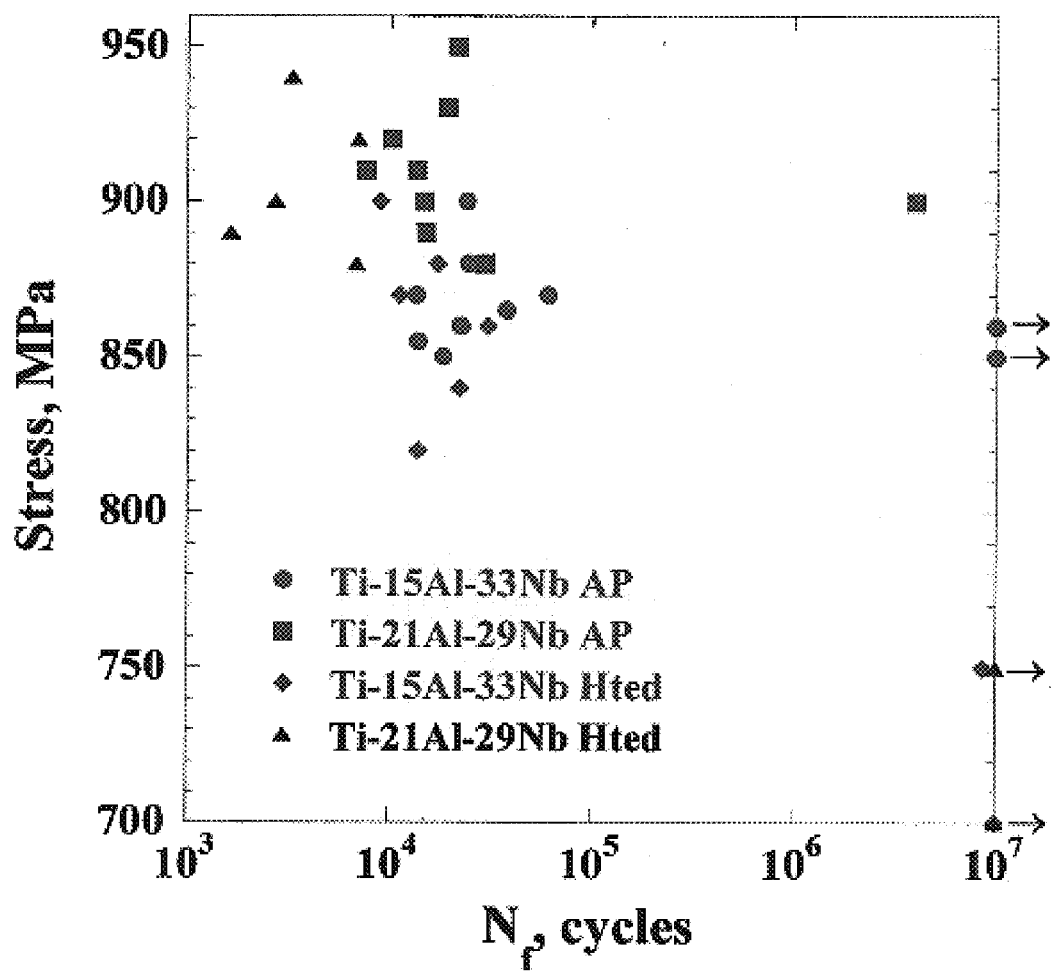
FIGS. 15A and 15B show maximum applied stress versus fatigue life.
Figure 15B:
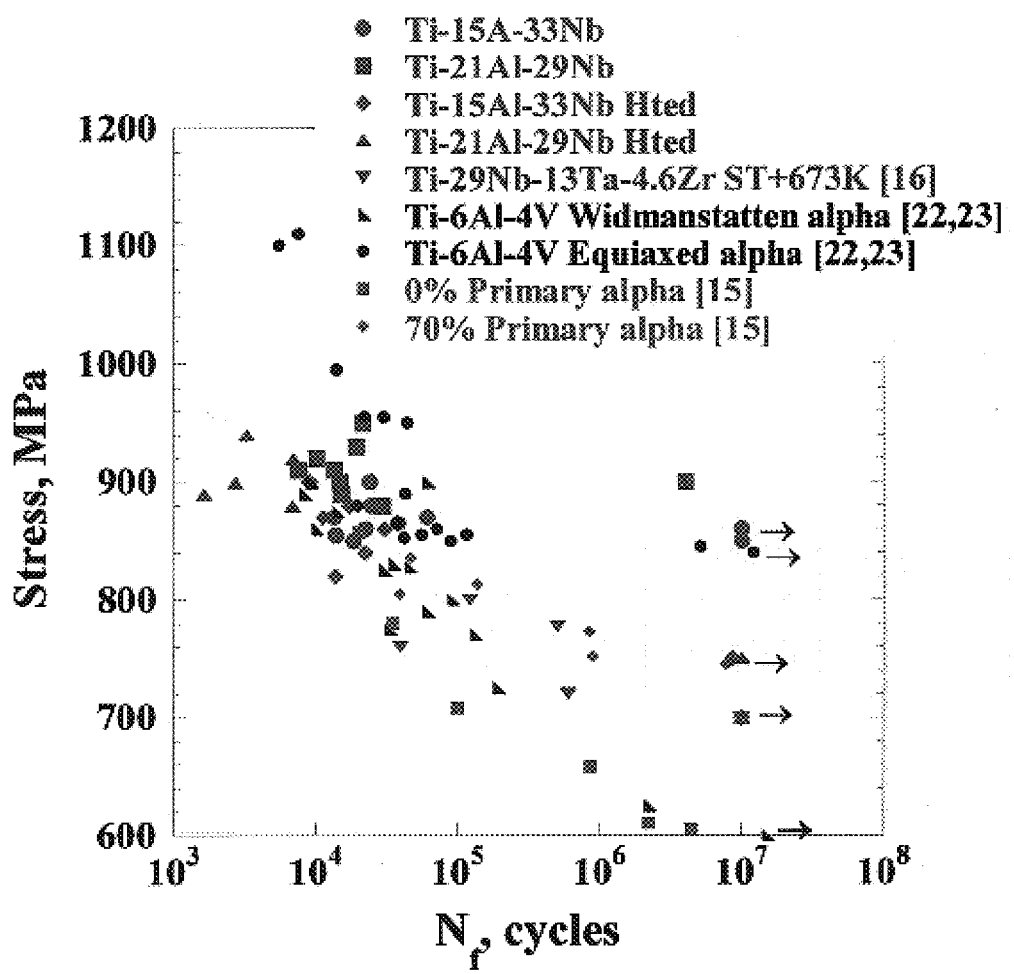
Figure 16A:
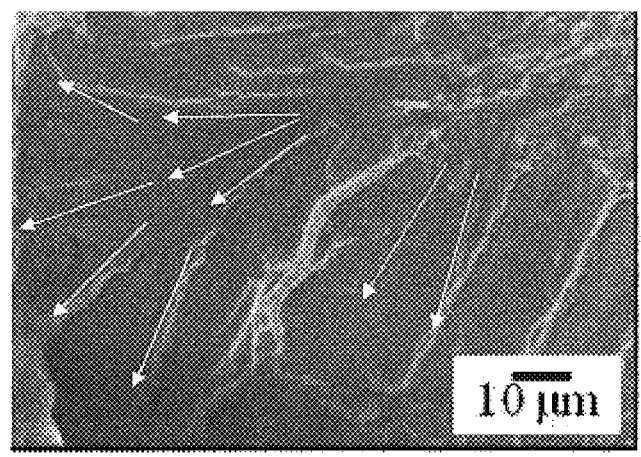
FIGS. 16A, 16B and 16C are SEM fractgraphs of as-processed Ti-21Al-29Nb samples tested at RT in air for a maximum stress of 930 MPa.
Figure 16B:
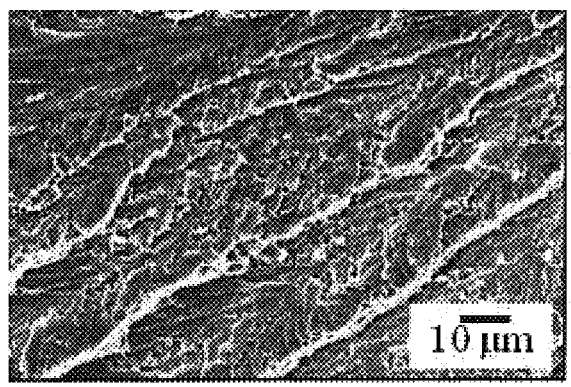
Figure 16C:
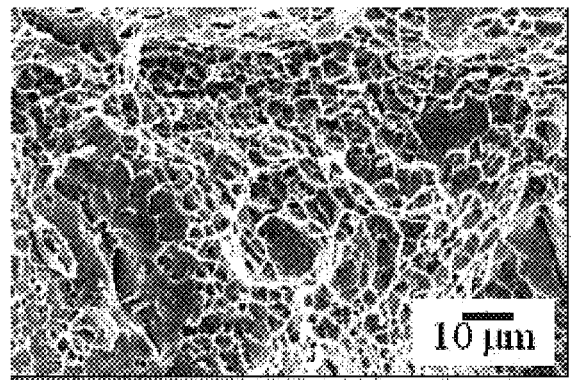
Figure 17A:
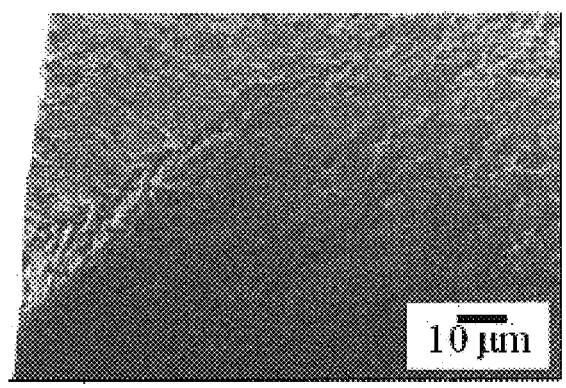
FIGS. 17A, 17B and 17C are SEM fractographs of as-processed Ti-15Al-33Nb samples tested at RT in air for a maximum stress of 865 MPa.
Figure 17B:
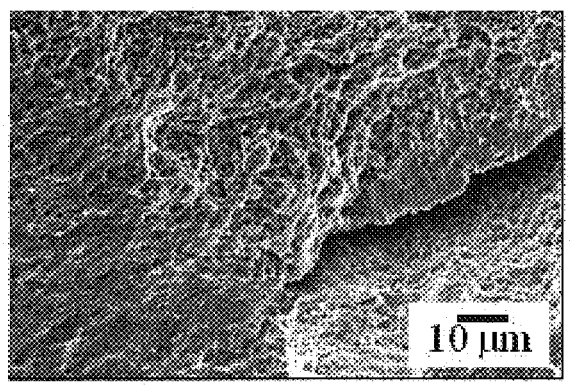
Figure 17C:
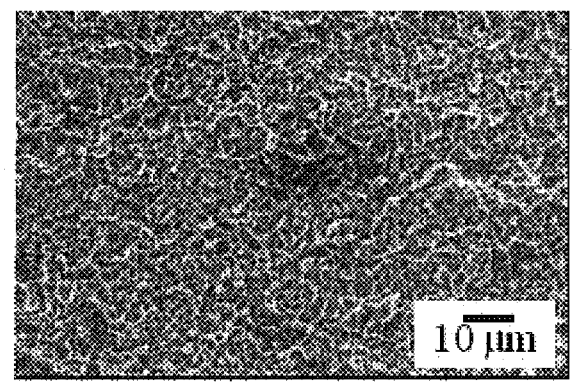
Figure 18A:
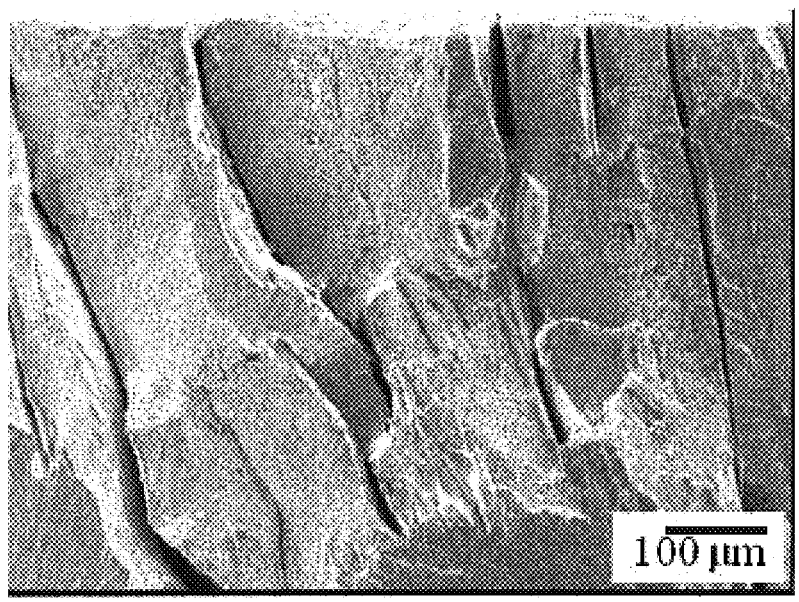
FIGS. 18A and 18B show low magnification.
Figure 18B:
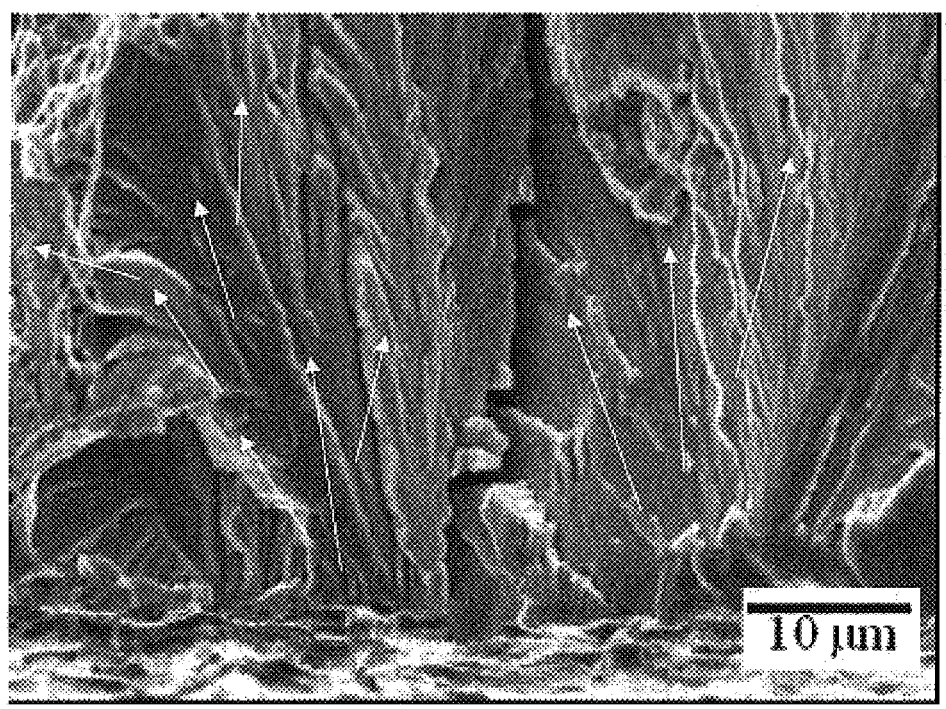

It is possible that the different test apparatuses may have lead to a discrepancy in the fatigue life data. Another explanation for the occurrence of relatively early failures and run-outs on many of the stress levels could be the potential existence of two (2) flaw populations. One (1) of the flaw populations (e.g. surface notches) leads to early failures, but is not present on all the tested specimens. In order to compare the current alloy results with other Ti alloys, the data obtained by Toyohashi University of Technology were used as all the Ti alloys compared were tested using an identical testing apparatus and similar maximum applied cyclic stresses (C. S. Lader, (1998), ibid; N. al Saffar (1994), ibid; D. Fender, (1999), ibid; and J. J. Callaghan (1998), ibid). FIG. 15A compares the S—N behavior for the as-processed and heat-treated Ti-21Al-29Nb and Ti-15Al-33Nb samples. The as-processed samples maintained higher fatigue lives on average than the heat-treated samples, and this may have been related to the increased RT tensile strength, which is particularly important for high-cycle fatigue and is in agreement with recent correlations between tensile strength and high-cycle fatigue behavior for a Ti-22Al-27Nb(at. %) alloy (G. C. McKay (1996), ibid). The ranges of fatigue strength of other Ti alloys, including conventional biomedical Ti-6Al-4V(wt. %) ELI and Ti-6Al-7Nb (wt. %), obtained from the literature (T. Akahori et al, (2000), ibid; M. Niinomi, (2003), ibid; M. Ikazaki, T. Hizume, J. Soc. Mater. Sci. Japan (1994) 43, pages 1238-1244; and T. Akahori, M. Niinomi, K. Fukunaga, I. Inagaki, Metall. Mater. Trans., 31A (2000) pages 1937-1948)), are also shown in the FIG. 15B for comparison. The current alloys exhibited greater fatigue strength than Ti-6Al-7Nb (wt. %) and the other β Ti alloys, while the fatigue lives were comparable to those for Ti-6Al-4V(wt. %) at a given maximum applied stress. It is noted that the actual compositions of the current alloys in weight percent was Ti-9.8Al-47.0Nb (wt. %) [Ti-21Al-29Nb] and Ti-6.9Al-51.7Nb (wt. %) [Ti-15Al-33Nb]. Thus, the additional Al and Nb concentration at the expense of Ti improved the fatigue life as evident in the comparison with Ti-6Al-7Nb (wt %). This is considered to be related to the greater RT tensile strength exhibited by the Ti-21Al-29Nb and Ti-15Al-33Nb alloys compared with Ti-6Al-7Nb (I. Watanabe, et al (2004), ibid), see Table 3.

TABLE 3

RT Tensile Properties of the studied alloys as well as Ti—6Al—4V (wt %)

| Alloy | Heat Treatment, °C. | E, GPa | YS, MPa | UTS, MPa | $\epsilon_f$, % |
|---|---|---|---|---|---|
| Ti—15Al—33Nb | AP | 94 | 876 | 916 | 12.4 |
| Ti—15Al—33Nb | 1005 | 111 | 799 | 852 | 2.1 |
| Ti—21Al—29Nb | AP | 103 | 972 | 1010 | 1.7 |
| Ti—21Al—29Nb | 1005 | 115 | 803 | 868 | 1.6 |
| Ti—6Al—4V | AP | 110 | 1063 | 1070 | 7.3 |
| Ti—6Al—7Nb [13] | na | 110 | 773 | 893 | 5.5 |

* results represent an average of at least two tests;
na: not available

The good fatigue strength of the investigated microstructures is considered to be due to the balance of strength and ductility brought by the O and BCC phases which leads to increased resistance to fatigue crack initiation and small fatigue crack propagation. It has been reported that, for the Ti alloys with relatively fine microstructures, a large part of fatigue life is occupied by the small fatigue crack initiation and propagation life (M. Hagiwara, Mater. Japan, (1998), 37: pages 35-38). This may be one reason why the fine microstructures exhibited good fatigue strength compared to the other biomedical Ti alloys. FIGS. 16A to 16C and 17A to 17C are SEM fractographs of as-processed Ti-21Al-29Nb and Ti-15Al-33Nb samples, respectively, in the fatigue crack initiation, propagation, and overload regions. The fatigue cracks tended to initiate at the specimen surface then propagate parabolically towards the inside of the specimen in every case. Relatively wide striations were observed in the stable crack growth region, and equiaxed dimples were observed in the overload or fast fracture region. Such fracture surface morphologies are observed generally for ductile metallic materials. It is noted that a smaller area of dimpled regions was observed for Ti-21Al-29Nb than for Ti-15Al-33Nb, which may have been a result of the lower $\epsilon_f$ values. In addition, the fracture surface in the crack initiation and stable crack growth regions was relatively flat for Ti-21Al-29Nb compared with the more tortuous Ti-15Al-33Nb surfaces. Considerable facets were observed near the crack initiation site in both low and high cycle fatigue life regions for Ti-21Al-29Nb, see FIGS. 16A to 16C and 18A and 18B. In the fast fracture area, a mixed-mode fracture surface composed of intergranular fractures, facets, and dimples were observed. Therefore, the fatigue crack initiation and propagation characteristics of Ti-21Al-29Nb resembled more of a brittle fracture than that for Ti-15Al-33Nb.

Figure 19A:
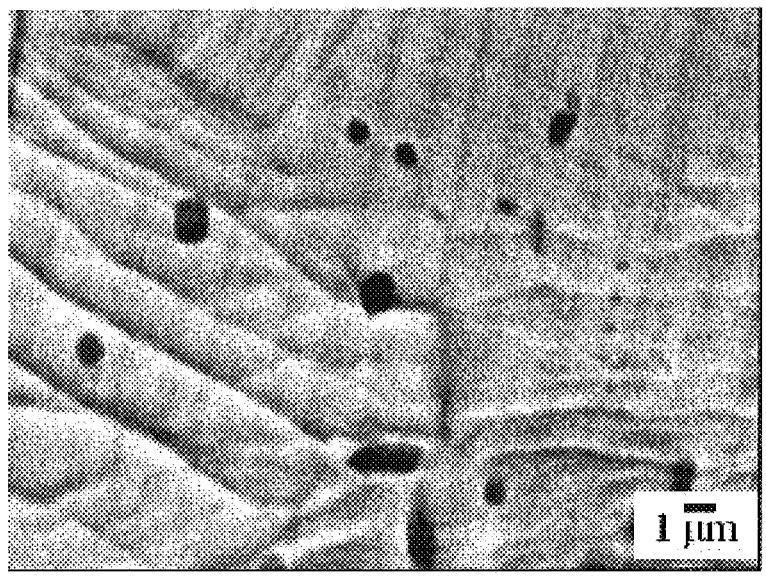
FIGS. 19A and 19B are SEM observations of surface slip traces for the as-processed fatigue samples.
Figure 19B:
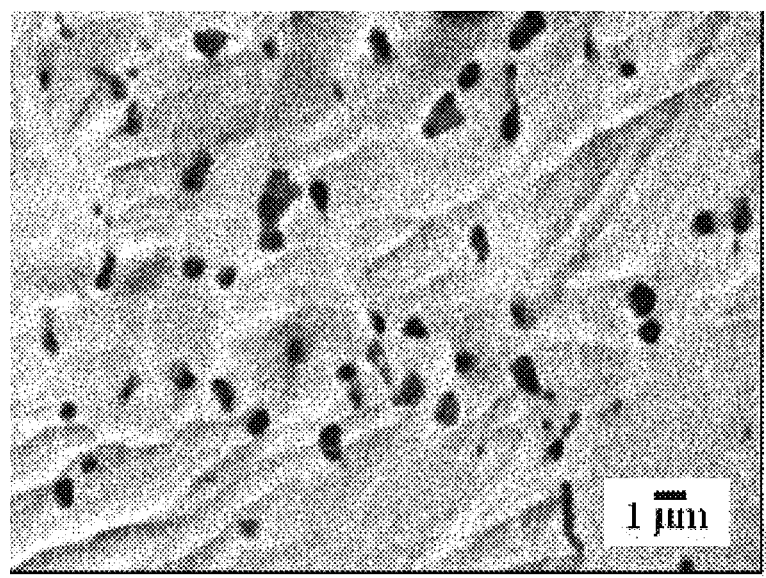

Surface slip traces were evident on all the as-processed fatigue samples, see FIGS. 19A and 19B. Such observations indicated that the slip was wavy within the ductile BCC phase and slip did transfer from the BCC phase to either the O phase or $\alpha_2$ phase. The ductile behavior is expected to have had a beneficial effect especially within the low-cycle fatigue regions where crack propagation is expected to dominate fatigue lives. The slip was more evident within the BCC phase than either the O or $\alpha_2$ phases. Thus, the BCC phase may play a significant role in promoting low-cycle fatigue resistance at RT for the Ti—Al—Nb alloys, as low-cycle fatigue is dominated by crack propagation for Ti alloys (L. Wagner, "Fatigue Life Behavior", in: Fatigue and Fracture Properties of Titanium Alloys, ASM Handbook Vol. 19 Fatigue and Fracture, ed. S. R. Lampman, ASM International, Materials Park, Ohio, 1996, pages 829-845).

The run-out samples were subsequently examined in RT tension, as described in the experimental section, and the associated data are listed in Table 5.

TABLE 5

RT Tensile UTS values of the as-processed fatigue run-out samples

| Alloy | Number of Cycles | Stress Cycled at, MPa | UTS, MPa |
|---|---|---|---|
| Ti—15Al—33Nb | 2,000,000 | 350 | 887 |
| Ti—15Al—33Nb | 2,000,000 | 350 | 1002 |
| Ti—15Al—33Nb | 2,000,000 | 350 | 907 |
| Ti—15Al—33Nb | 2,000,000 | 450 | 972 |
| Ti—15Al—33Nb | 2,000,000 | 550 | 928 |
| average | | | 939 |
| Ti—21Al—29Nb | 2,000,000 | 350 | 995 |
| Ti—21Al—29Nb | 2,000,000 | 350 | 1048 |
| Ti—21Al—29Nb | 2,000,000 | 350 | 1021 |
| Ti—21Al—29Nb | 2,000,000 | 350 | 1023 |
| Ti—21Al—29Nb | 2,000,000 | 400 | 897 |
| Ti—21Al—29Nb | 2,000,000 | 450 | 1106 |
| Ti—21Al—29Nb | 2,000,000 | 450 | 1062 |
| average | | | 1022 |

Figure 20A:
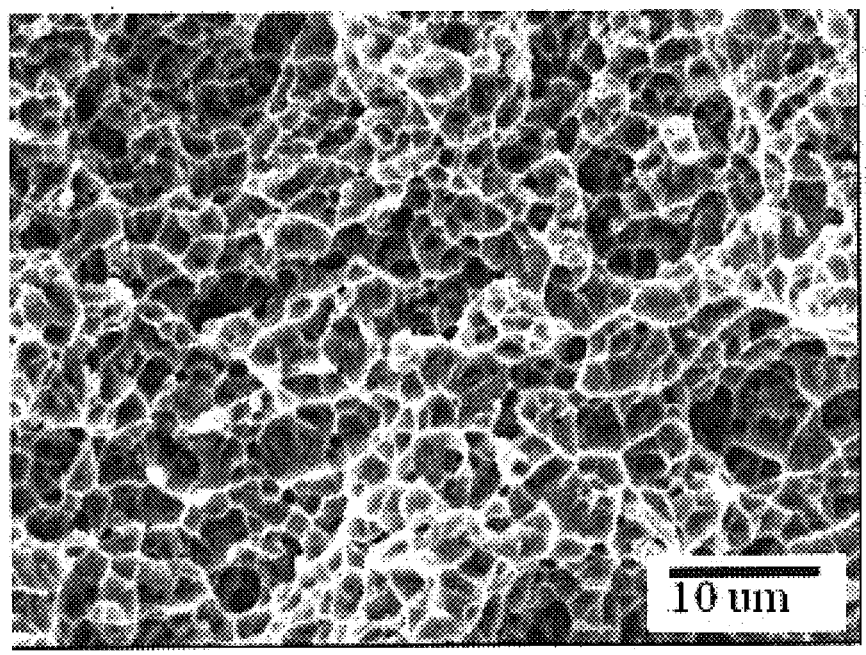
FIGS. 20A and 20B show SEM images of the fracture surfaces of the RT tensile tested as-processed specimens which underwent fatigue run out ($2\times10^6$ cycles).
Figure 20B:
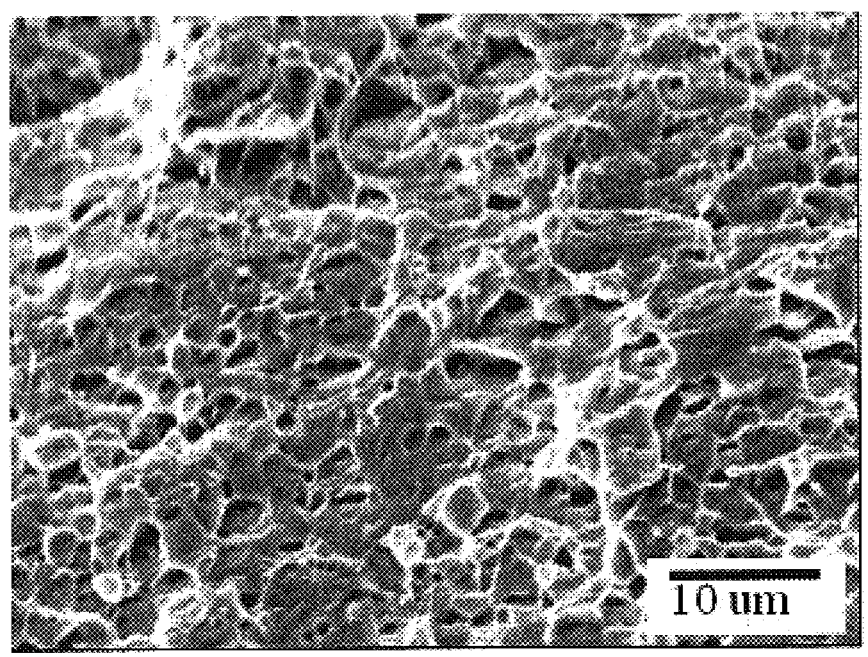

Such samples did not exhibit lower strength values on average than those which were not fatigue tested. Thus, no clear evidence, in terms of strength loss, was apparent that fatigue testing reduced tensile strength. The corresponding fracture surfaces, FIGS. 20A and 20B, exhibited similar features to those for virgin samples which were only RT tensile tested. No significant differences with respect to the number of crack initiation sites from those specimens which only underwent RT tensile fracture were evident. Thus, the run-out samples did not show deleterious effects from the fatigue cycling whatsoever. It is suggested that any microcracks which may have developed during fatigue in such specimens, were not detrimental to the tensile strength. Thereby, it is considered that few large cracks initiated and grew during fatigue for the specimens which exhibited run out.

Summary and Conclusions

The ambient-temperature fatigue and tensile behavior of Ti-21Al-29Nb and Ti-15Al-33Nb alloys was investigated and compared to that for Ti-6Al-4V (wt. %) and other alloys in order to evaluate newer Ti—Al—Nb alloys (i.e. other than Ti-6Al-7Nb(wt. %)) for potential biomedical implant applications. The following conclusions are summarized.

1. The as-processed Ti-21Al-29Nb and Ti-15Al-33Nb microstructures exhibited a majority of BCC phase and the grain sizes were relatively fine, containing an average diameter of 3 μm. The heat-treated microstructures contained a larger grain size and a greater volume fraction of the 0 phase.
2. The RT strength and elastic modulus of Ti-21Al-29Nb were larger than that for Ti-15Al-33Nb and this is expected to be a result of the greater Al content and corresponding greater O-phase volume fraction. Also a result of the greater Al content was the very low $\epsilon_f$ values. Higher BCC-phase contents are critical for maintaining ductility in the Ti—Al—Nb alloy system. The elastic modulus of the Ti—Al—Nb alloys was similar to that for Ti-6Al-4V (wt. %) ELI.
3. Ringer's solution neither degraded nor improved the fatigue lives and no significant differences were observed within the fracture surfaces for samples tested in Ringer's solution or air. The chosen heat treatment resulted in lower fatigue lives than the as-processed alloys, which exhibited fatigue lives comparable to those for Ti-6Al-4V (wt. %) ELI.
4. Surface crack initiation, striations within the stable fatigue crack propagation area, and equiaxed dimples on the fast fatigue crack propagation area were observed in low and high cycle fatigue life regions for both alloys. Ti-15Al-33Nb exhibited a ductile fracture surface morphology while Ti-21Al-29Nb tended to exhibit more of a brittle fracture surface morphology.
5. No clear evidence, in terms of strength loss, was apparent that fatigue testing reduced RT tensile strength.
6. Based on the data obtained on the tensile and fatigue behavior, the Ti-15Al-33Nb and Ti-21Al-29Nb alloys merit further evaluation for biomaterial applications.

Examples for Biocompatibility Evaluation of Ti-15Al-33Nb(at. %) and Ti-21-Al-29Nb(at. %)

In these Examples, the biocompatibility of two (2) vanadium-free Ti—Al—Nb alloys, Ti-15Al-33Nb and Ti-21Al-29Nb, was evaluated and compared to that for commercially pure titanium (CP Ti) and alumina ($Al_2O_3$). Fine particles were milled from sheet-processed material and implanted onto mice calvaria using an established animal model. Various stains, including methylene blue/acid fuchsin, TRAcP, and immunohistochemistry, were used on the particle-treated calvaria to measure the extent of bone deterioration of the calvaria, quantify the amount of osteoclasts, and approximate the presence of T-cells. In addition, reaction with particle-stimulated macrophages was observed and the production of the cytokine TNF was recorded and quantified. The results indicated that the Ti—Al—Nb alloys statistically outperformed both CP It and $Al_2O_3$ in terms of their overall biocompatibility with respect to the experiments performed.

Figure 21A:
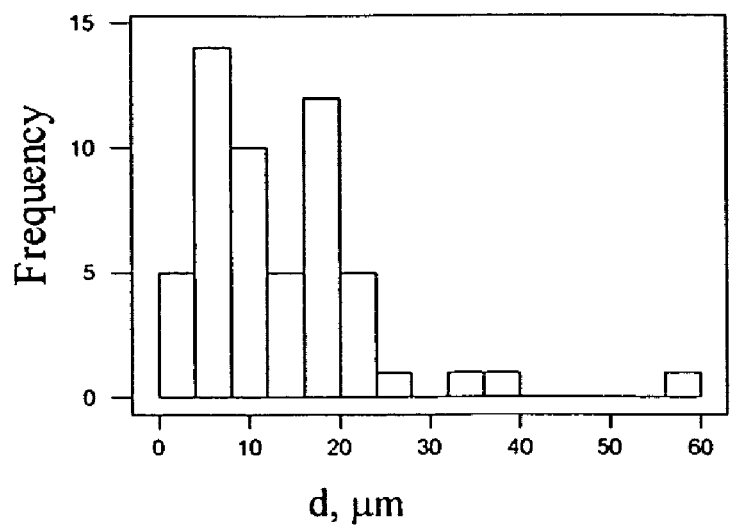
FIGS. 21A and 21B show representative particle size distribution for Ti-15Al-33Nb (FIG. 21A) and Ti-21Al-29Nb (FIG. 21B).
Figure 21B:
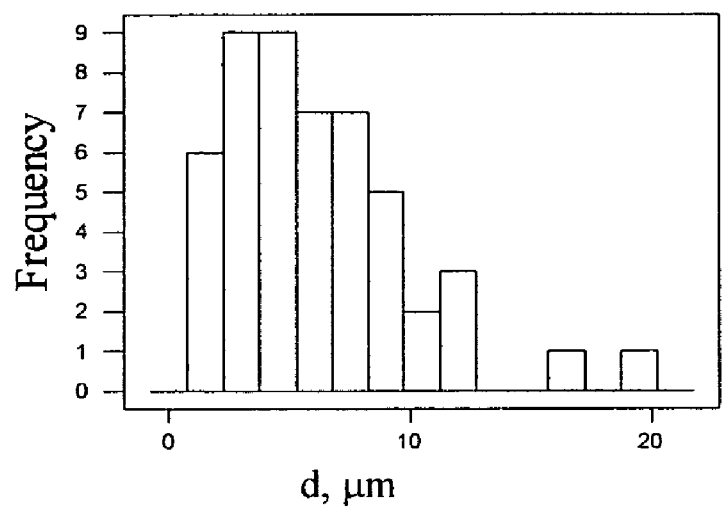

The Ti—Al—Nb alloy particles used for the experiments were first filed from the sheet samples of the preceding Examples. Approximately five grams of the filings were then shipped out to Spex CertiPrep, Inc. (Metuchen, N.J., USA) for further breakdown. The softer and ductile Ti-15Al-33Nb filings were milled for 20 minutes using a Shatterbox 8515 and a Zirconia Grinding Container 8506 along with 10 ml of Vertrel XF, a fluorocarbon fluid which prevents particles from welding together under pressure, as a grinding aid. The harder and brittle Ti-21Al-29Nb filings were broken down for two (2) hours in a 8004 Tungsten Carbide Vial, 8000M Mixer/Mill using 6 ml of Vertrel XF. The size distribution of the resulting particles was measured using both scanning electron microscopy (SEM) coupled with image analysis and a light scattering technique for powder suspensions (J. P. Krathovil, Light Scattering: Anal. Chem. 36:5 (1964) 458R and M. Kerker, Scattering of Light and Other Electromagnetic Radiation (Academic Press, New York, 1969) 1)). The SEM used was an AMRAY 1810 SEM and the light-scattering device was a Leeds Northrup Instruments Microtrac FRA. The results from these analysis indicated that the Ti-15Al-33Nb particles ranged in size from 2-60 µm and the average particle diameter was 13.6 µm, see FIG. 21A. The Ti-21Al-29Nb particles ranged in size from 1-20 µm and the average particle diameter was 6.1 µm, see FIG. 21B. CP Ti particles, obtained from Johnson Mathey Chemicals (Ward Hill, Mass., USA), were also evaluated, and the particle preparation was described previously (E. M. Schwarz, E. B. Benz, A. P. Lu, J. J. Goater, A. V. Mollano, R. N. Rosier, J. E. Puzas, and R. J. O'Keefe: Journal of Orthopedic Research 18 (2000) pages 849-855; and L. M. Childs, J. J. Goater, R. J. O'Keefe, and E. M. Schwarz: Journal of Bone and Mineral Research 16:2 (2001), pages 338-347)). SEM measurements indicated that 90% of these particles were less than 10 µm in diameter. Alumina oxide powers were purchased from Alfa Aesar (Ward Hill, Mass., USA) and the SEM measurements indicated that they ranged between 0.5-5 µm in diameter.

Particle Implantation

A mouse calvaria model of wear debris-induced bone loss, including quantification of in vivo osteoclast numbers, was utilized where implantation of particles in the mice was performed following the procedure discussed previously (E. M. Schwarz, E. B. Benz, A. P. Lu, J. J. Goater, A. V. Mollano, R. N. Rosier, J. E. Puzas, and R. J. O'Keefe: Journal of Orthopedic Research 18 (2000), pages 849-855; L. M. Childs, J. J. Goater, R. J. O'Keefe, and E. M. Schwarz: Journal of Bone and Mineral Research 16:2 (2001), pages 338-347; and J. J. Goater, R. J. O'Keefe, R. N. Rosier, J. E. Puzas, and E. M. Schwarz, Journal of Orthopedic Research 20 (2002), pages 169-173)). Briefly, five or six healthy homozygous C57BL/6 mice (The Jackson Laboratory, Bar Harbor, Me.) were used in each group. All animals were housed and treated according to guidelines approved by the Alfred University Institutional Animal Care and Use Committee. Mice were anesthetized with 70-80 mg/kg of ketamine and 5-7 mg/kg of xylazine by intraperitoneal (i.p.) injection. A 1×1 cm² area of calvarial bone was exposed by making a midline sagittal incision over the calvaria, leaving the periosteum intact. Approximately 30 mg of the particles were spread over the area and the incision was closed. Baseline animals did not undergo surgery nor received particle implantation. Ten (10) days after surgery, the mice were sacrificed and the calvaria were harvested. Each calvarium was cut in half laterally such that the midline suture was in the center of the cross-section. They were then fixed in 10% buffered neutral formalin (Pharmco Products Inc., Brookfield, CT, USA) for 24 hours. The calvaria were next decalcified in 10% EDTA (pH=7.2) for one (1) week. The calvaria were then processed, embedded in paraffin, and cut into 5 µm sections using a Microm 310 microtome (Richard-Allan Scientific, Kalamazoo, Mich., USA). These sections were then placed onto slides and let sit overnight at 75° C. in an oven. After baking overnight, the slides were deparaffinized for four (4) minutes in four (4) separate xylenes and rehydrated in a series of ethanol solutions prior to performing the staining procedures.

Methylene Blue/Acid Fuchsin Staining

The amount of bone deterioration was quantified using a new differential stain for bone and soft tissue (K. A. Rider and L. M. Flick: Analytical and Quantitative Cytology and Histology 26:5 (2004), pages 246-248). Briefly, slides were deparaffinized and rehydrated, set in 0.2% methylene blue (Fisher Scientific, Fairlawn, N.J., USA) for 30 seconds, rinsed and incubated in acid fuchsin (Fisher Scientific) for five (5) minutes. The stained slides were then dehydrated, cleared, and coverslipped then observed using an Olympus IX51 (Melville, N.Y., USA) inverted optical microscope (OM) at 40× magnification. Using Scion Image (Scion Corp., Frederick, Md., USA) software, the area of soft tissue between the parietal bones of the midline sagittal suture was traced and measured. These measurements of the particle-treated calvaria were compared with the measurements from calvaria that were not treated.

TRAcP Staining

Osteoclasts are multinucleated cells which are derived from monocyte precursors and resorb bone. Therefore, the more osteoclasts present, the more deterioration of the calvaria bone. The number of TRAcP+ osteoclasts was determined in calvarial sections using a cytochemical staining technique. Positive control slides of mouse tibia were also stained. Slides were incubated in a naphthol AS-BI phosphate (Sigma) substrate solution at 37° C. for 45 minutes followed by treatment in pararosaniline-nitrite dye for 6 minutes. Slides were then counterstained with hematoxylin. Each section was digitally photographed at 40× magnification using the OM and the number of TRAcP+ cells within the midline sagittal suture area was counted.

Immunohistochemistry Staining

The immunohistochemistry stain highlights the T-cells present in the particle-treated calvaria as a result of chemokine-mediated T-cell migration to the calvaria. Immunohistochemistry was performed on calvaria and spleen (positive control) sections following citrate buffer antigen retrieval using an antibody to the pan-T-cell marker CD3ε (Santa Cruz Biotechnology, Santa Cruz, Calif., USA). VECTASTAIN ABC and NovaRED substrate kits (Vector Laboratories, Burlingame, Calif., USA) were used to develop the sections which were then counterstained with hematoxylin. The slides were observed using the OM at 40× magnification, and photographed using the Olympus DP12 digital camera (Melville, N.Y., USA).

Cytokine Production In Vitro

RAW 264.7 murine macrophage cell line was obtained from the American Type Culture Collection (Rockville, Md., USA) and grown in Dulbecco's Modified Eagle's Medium (DMEM; Sigma) supplemented with 10% fetal bovine serum and 1% antibiotic/antimycotic solution (Gibco, Grand Island, N.Y., USA). $8 \times 10^5$ cells were plated into each well of a 6-well culture plate and stimulated with various concentrations of CP Ti, $Al_2O_3$, Ti-15Al-33Nb and Ti-21Al-29Nb for 24 hours. Cells were photographed using the OM at 100× magnification and culture media was collected for analysis. TNFα was determined by enzyme-linked immunosorbent assay (ELISA) using antibodies and recombinant standards obtained from R&D Systems (Minneapolis, Minn., USA) as previously described (L. M. Childs (2001), ibid). The recombinant standard was used to create a standard curve from which the concentration of TNFα in the samples could be calculated.

Statistical Analysis

Statistical significance was determined using Student's t-test where values less than p=0.05 were considered significant for single comparisons.

Electron Microscopy Characterization

Microstructure

Characterization of the as-processed Ti—Al—Nb sheet microstructures was carried out using OM, SEM, and X-ray diffraction (XRD) analysis. Sheet samples were diamond cut and mounted in epoxy then ground using successively finer grits of silicon carbide paper. After grinding, the samples were polished using diamond paste according to the following schedule: 30 μm for five minutes, 15 μm for five minutes, 6 μm for five minutes, 1 μm for 20 minutes. Colloidal silica with an average particle size of 0.06 μm was used for the final polish. SEM images were obtained using an AMRAY 1810 SEM. The constituted phases were examined through XRD analysis, carried out using a Cu target with an accelerating voltage of 40 kV and a current of 30 mA.

Particle-Treated Calvaria

Extracted calvaria were placed in 1×PBS for approximately five (5) hours. The samples were then transferred to 70% ethanol for two days then placed in a weighing tray to dry at room temperature. OM images of the calvaria samples were then obtained. Samples were then secured to SEM stubs using colloidal graphite and vacuum sputter-coated with a thin gold-palladium layer order to ensure conductivity of the samples for SEM imaging, performed using a Phillips model 515 SEM (Boston, Mass. (FEI Corp.). Multiple SEM magnifications were used to examine the boundary between bone and particles on the samples. Energy dispersive spectroscopy (EDS) analysis was performed on the calvaria, particles, and the interface between the calvaria and particles. The particle interaction with the calvaria was also characterized using a FEI Quanta 200 (Boston, Mass.) environmental scanning microscope (ESEM) in low-vacuum mode where no conductive coating was necessary.

Results and Discussion

Microstructure

Figure 22A:
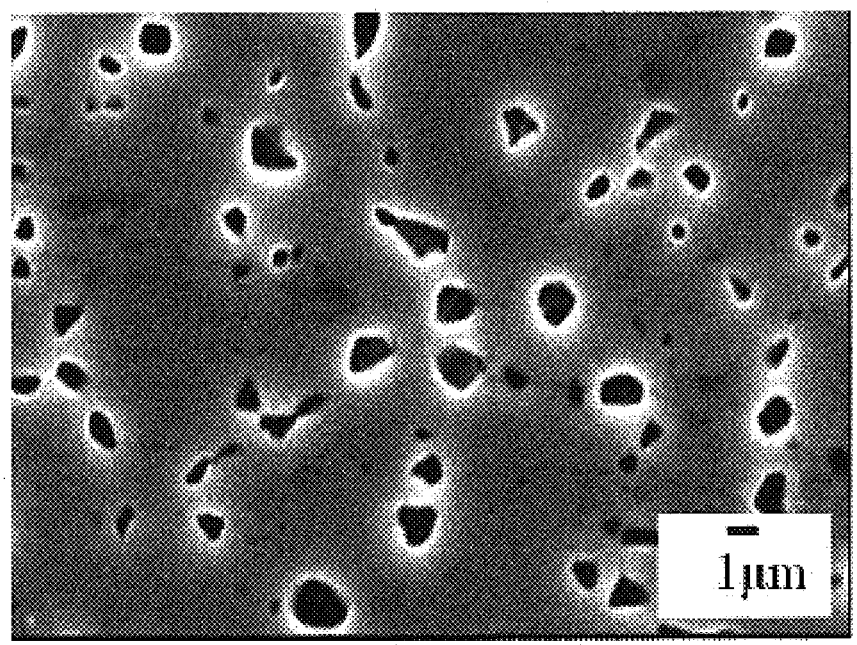
FIGS. 22A and 22B are SEM images of the as-processed.
Figure 22B:
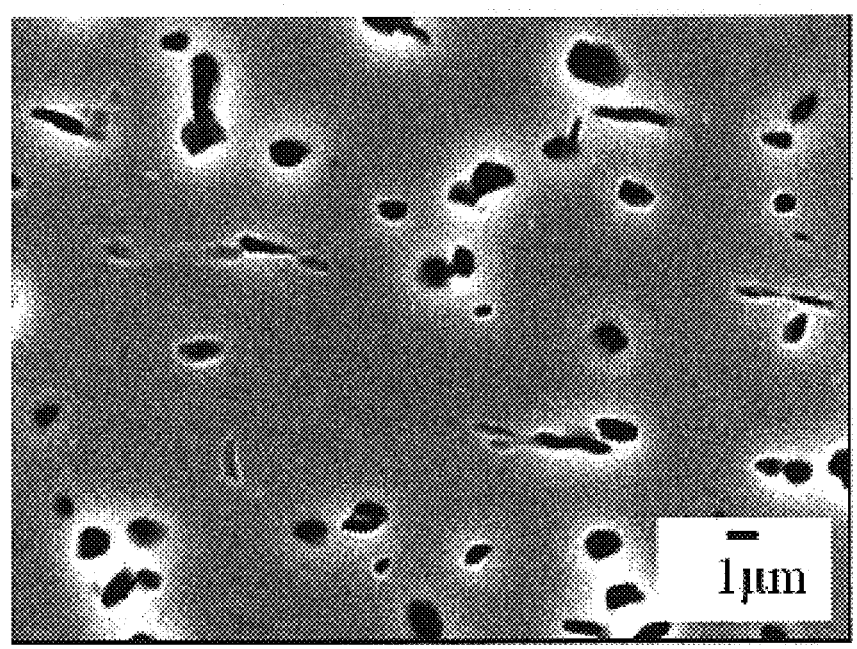

The measured chemical compositions of the Ti—Al—Nb alloys are provided in Table 6 and the as-processed sheet microstructures are shown in FIGS. 22A and 22B. The as-processed alloys were composed almost entirely (≧90% by volume of the body-centered-cubic phase and smaller quantities of the orthorhombic and hexagonal-close-packed phase were dispersed throughout the sample.

TABLE 6

Ti—Al—Nb Alloy compositions

| Alloy | Ti (at %) | Al (at %) | Nb (at %) | Fe (ppm) | O (ppm) | N (ppm) |
|---|---|---|---|---|---|---|
| Ti—15Al—33Nb | 51.4 | 15.3 | 33.3 | 110 | 1100 | 100 |
| Ti—21Al—29Nb | 50.7 | 20.6 | 28.7 | 2000 | 790 | 110 | ppm: parts per million

Imaging of Treated Calvaria

Figure 23A:
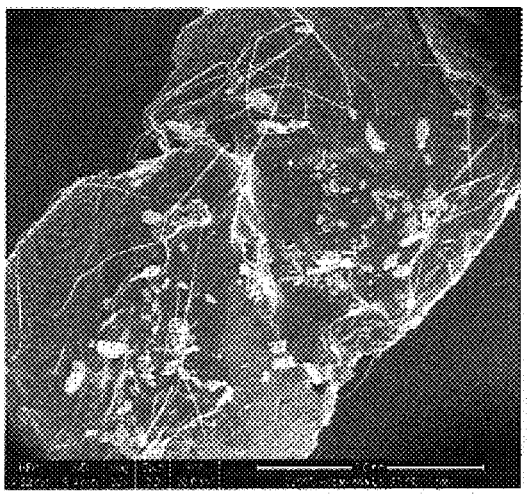
FIGS. 23A and 23B show low (FIG. 23A) and high (FIG. 23B) magnification ESEM images of Ti-15Al-33Nb particle-treated calvaria indicating a coherently-bonded interface. These images indicate that the particles (lighter) were denser than the calvaria soft and hard tissue (darker). No adverse reactions were noted with the cantilever or the soft tissue for 10 days after attachment of the particles.
Figure 23B:
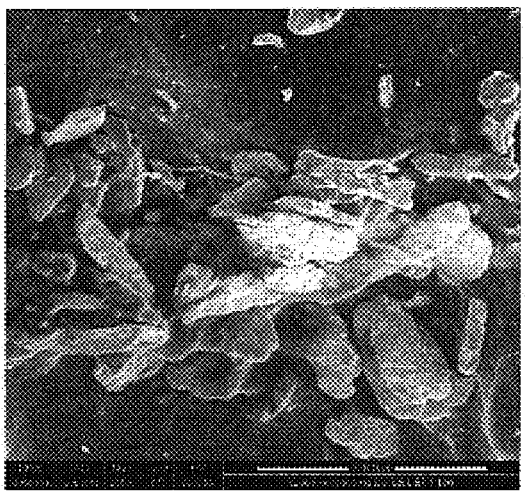
Figures 24A, 24B:
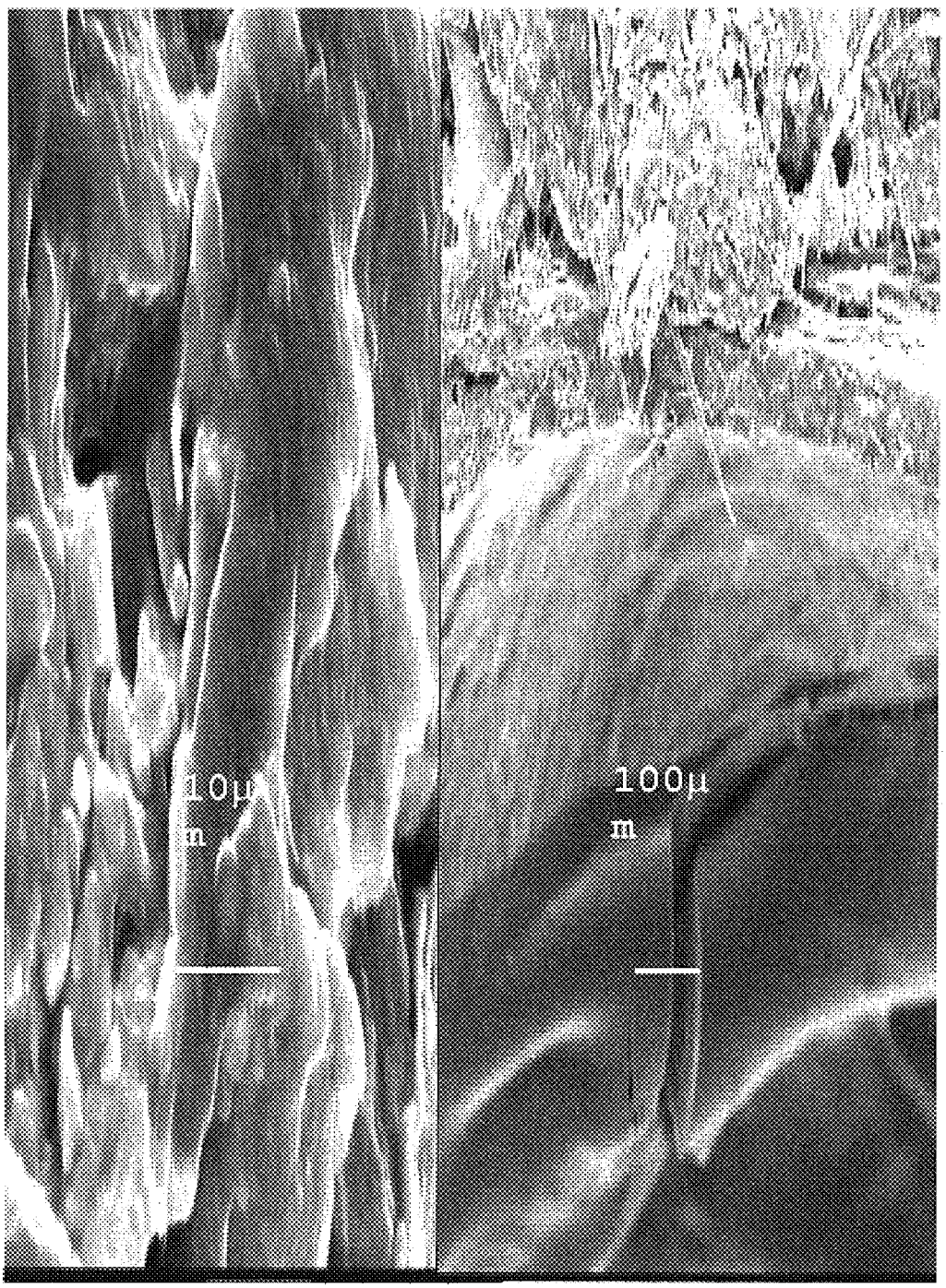
FIGS. 24A and 24B show low (FIG. 24A) and high (FIG. 24B) magnification SEM images of the interface between Ti-21Al-29Nb powders and a mouse calvaria indicating the coherent interface. No adverse reactions were noted with the cantilever or the soft tissue.

OM, SEM, and EDS analysis confirmed that no significant detrimental reaction occurred between the Ti—Al—Nb alloy particles and the calvaria. FIGS. 23A and 23B illustrate ESEM images of the interaction between the Ti-15Al-33Nb particles and the calvaria. The particles appeared to have adhered well with the calvaria where no interfacial cracking or detrimental reaction layer were observed, see FIGS. 24A and 24B. The EDS spectra taken from the calvaria region indicated carbon, oxygen, phosphorous, and calcium were present while analysis of the particles indicated Al, Nb, and Ti were present. For EDS analysis of the boundary between the particles and calvaria, elements from both components were observed further indicating that there was some interaction between the calvaria and particles.

Methylene Blue/Acid Fuchsin

Figure 25A:
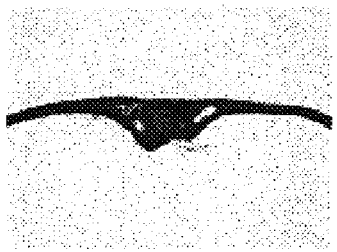
FIGS. 25A, 25B, 25C, 25D and 25E show OM images (40×) of methylene blue/acid fuchsin-stained.
Figure 25B:
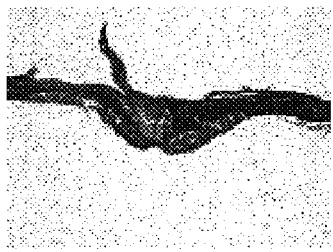
Figure 25C:
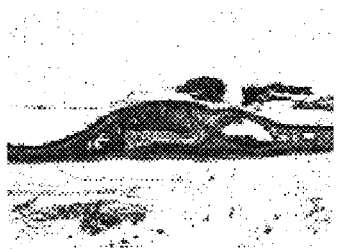
Figure 25D:
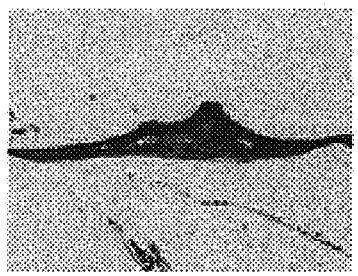
Figure 25E:
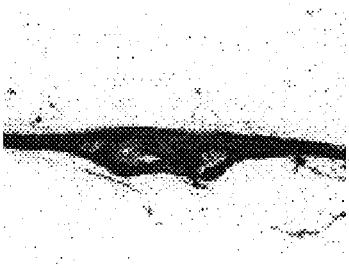

The amount of bone deterioration was quantified by using a methylene blue/acid fuchsin stain imaged optically at 40× magnification, see FIGS. 25A and 25B. As compared to the baseline samples, the bone edges for the particle-treated samples were more jagged indicating that there was more deterioration that took place in the particle-treated samples. The Scion Image software was used to trace the center portion of the calvaria. Once traced, the program computes the total area enclosed, and this is the total midline sagittal suture area (MSA). The difference between the average MSA for the baseline and treated samples represents the amount of bone deterioration in response to the particles. In comparing the particle-treated samples, Ti-15Al-33Nb- and Ti-21Al-29Nb-treated samples showed the least amount of deterioration, see Table 7, where the Ti-21Al-29Nb-treated samples exhibited slightly more deterioration than Ti-15Al-33Nb. In comparing the $Al_2O_3$, and CP Ti-treated particles, it was found that slightly more deterioration occurred in the $Al_2O_3$-treated samples. The overall measurement for the baseline was found to be 0.1382 $mm^2$ followed by Ti-15Al-33Nb and Ti-21Al-29Nb-treated samples with measurements of 0.1497 and 0.1862 $mm^2$ respectfully, which were significantly lower than those for the $Al_2O_3$-treated (0.3272 $mm^2$) and CP Ti-treated (0.2959 $mm^2$) samples. The difference between the measurements for the $Al_2O_3$- and CP Ti-treated samples was not statistically significant.

TABLE 7

Area measurements (in $mm^2$) of the relative bone deterioration for the particle-treated calvaria samples

|  |  | Average |
|---|---|---|
| Baseline 1 | 0.0728 | 0.1383 |
| Baseline 2 | 0.1338 |  |
| Baseline 3 | 0.0551 |  |
| Baseline 4 | 0.2353 |  |
| Baseline 5 | 0.2027 |  |
| Baseline 6 | 0.1298 |  |
| $Al_2O_3$ 1 | 0.2814 | 0.3272 |
| $Al_2O_3$ 2 | 0.3255 |  |
| $Al_2O_3$ 3 | 0.4207 |  |
| $Al_2O_3$ 4 | 0.1325 |  |
| $Al_2O_3$ 5 | 0.2895 |  |
| $Al_2O_3$ 6 | 0.5134 |  |
| CP Ti 1 | 0.3786 | 0.2959 |
| CP Ti 2 | 0.2404 |  |
| CP Ti 3 | 0.2272 |  |
| CP Ti 4 | 0.3762 |  |
| CP Ti 5 | 0.2572 |  |
| Ti—15Al—33Nb 1 | 0.1246 | 0.1497 |
| Ti—15Al—33Nb 2 | 0.1287 |  |
| Ti—15Al—33Nb 3 | 0.2455 |  |
| Ti—15Al—33Nb 4 | 0.1715 |  |

TABLE 7-continued

Area measurements (in mm²) of the relative bone deterioration for the particle-treated calvaria samples

| | | |
|---|---|---|
| Ti—15Al—33Nb 5 | 0.0782 | |
| Ti—21Al—29Nb 1 | 0.1975 | 0.1862 |
| Ti—21Al—29Nb 2 | 0.1406 | |
| Ti—21Al—29Nb 3 | 0.3069 | |
| Ti—21Al—29Nb 4 | 0.1426 | |
| Ti—21Al—29Nb 5 | 0.1433 | |

TRAcP

Figure 26:
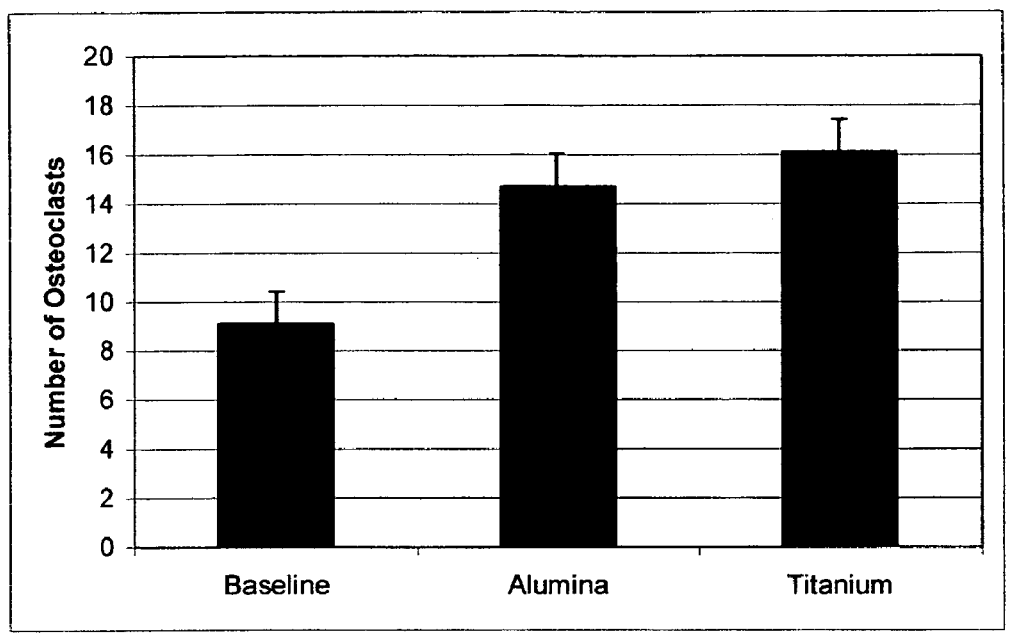
FIG. 26 is a bar chart indicating the average number of osteoclasts observed in the particle-treated calvaria.
Figure 27A:
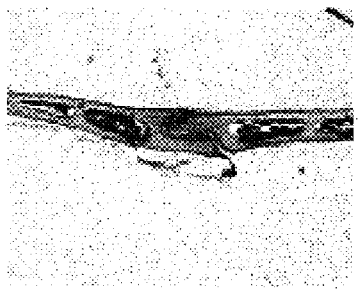
FIGS. 27A to 27E are OM images (40×) of immunohistochemistry-stained.
Figure 27B:
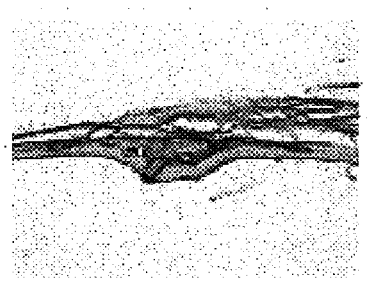
Figure 27C:
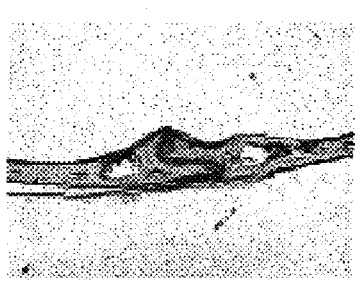
Figure 27D:
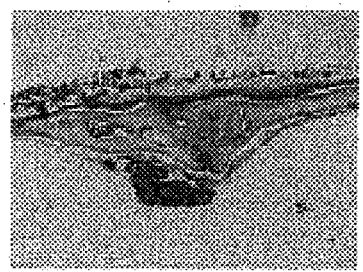
Figure 27E:
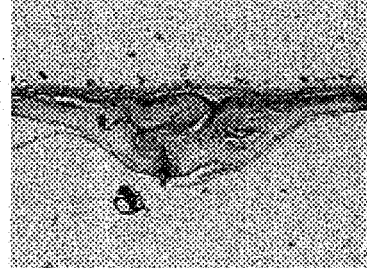
Figure 28A:
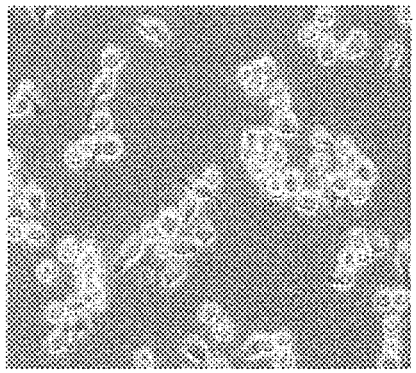
FIGS. 28A to 28E are OM images (40×) depicting particle phagocytosis.
Figure 28B:
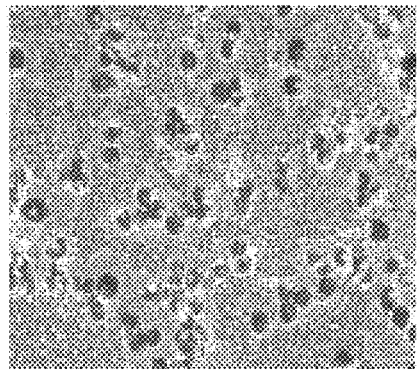
Figure 28C:
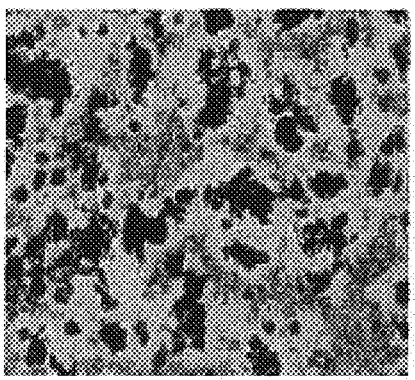
Figure 28D:
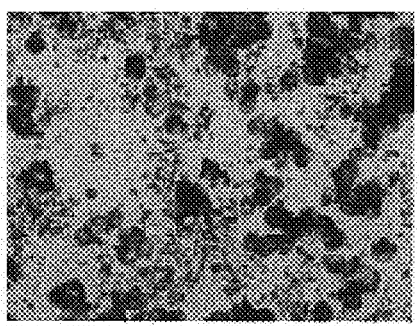
Figure 28E:
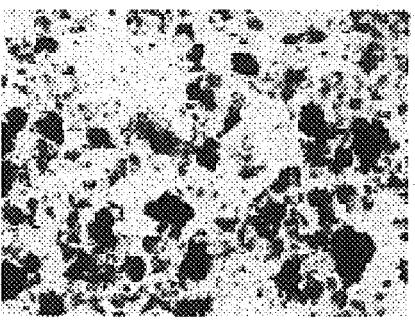

The number of osteoclasts present in both non-treated and particle-treated samples was measured using the TRACP stain. Osteoclasts were counted using the OM at 40× for the baseline, $Al_2O_3$- and CP Ti-treated calvaria samples. It was found that the CP Ti-treated samples contained the most osteoclasts while the baseline samples contained the least amount. The baseline, $Al_2O_3$-, and CP Ti-treated samples contained an average of 9.1, 14.7, and 16.1 osteoclasts, respectively (see Table 8 and FIG. 26). Statistical analysis indicated that the baseline value was statistically significant compared to that for both the $Al_2O_3$- ($p=0.0001$) and CP Ti-treated samples, however the difference between the $Al_2O_3$- and CP Ti-treated samples was not statistically significant ($p=0.07$). This agrees with the data from the methylene blue/acid fuchsin stain which showed bone deterioration is higher in $Al_2O_3$- and CP Ti-treated samples compared to baseline and Ti—Al—Nb alloy treated mice.

ited few T-cells. The CP Ti treated calvaria showed intense reddish-brown staining indicating larger quantities of T-cells compared to baseline (as expected), while minimal staining was present in Ti-15Al-33Nb and Ti-21Al-29Nb-treated calvaria (similar to baseline samples). This indicates that the alloys induce less T-cell migration into calvarial tissues than the CP Ti. The least amount of T-cells was present in the $Al_2O_3$ samples which suggests that this material induces inflammation and bone erosion but not T cell infiltration.

Stimulation of Cells

OM images were taken of untreated as well as $Al_2O_3$-, CP Ti,- Ti-15Al-33Nb-, and Ti-21Al-29Nb-stimulated macrophages, see FIGS. 28A to 28E. All images were of stimulated cells after a 24-hour period of incubation in a 37° C. incubator. After only 24 hours, the macrophages have engulfed nearly all of the particles in the vicinity of each cell as indicated by the density of particles in each cell and the clear zone containing no particles surrounding each individual macrophage or cluster of cells. In comparing the four (4) different materials, all cells reacted nearly equally to the particles, and all macrophages consumed the particles with no apparent harm to the cell itself (cells are still viable).

TNFα Production

TNFα is a critical inflammatory cytokine involved in inducing inflammation and bone erosion. TNFα is produced when macrophages phagocytose particulate material, therefore, particles which stimulate more TNFα are likely to cause

TABLE 8

Amount of osteoclasts present in baseline, $Al_2O_3$— and CP Ti-treated calvaria samples

| Sample | Sets 1-3 | Ave. | Sample | Sets 1-3 | Ave. | Sample | Sets 1-3 | Ave. |
|---|---|---|---|---|---|---|---|---|
| Baseline 1 | 12 | 11.7 | $Al_2O_3$ 1 | 13 | 14.3 | CP Ti 1 | 18 | 17.3 |
| | 18 | | | 17 | | | 16 | |
| | 15 | | | 13 | | | 18 | |
| Baseline 2 | 11 | 10.3 | $Al_2O_3$ 2 | 21 | 17 | CP Ti 2 | 11 | 16 |
| | 8 | | | 17 | | | 17 | |
| | 12 | | | 13 | | | 20 | |
| Baseline 3 | 13 | 8.7 | $Al_2O_3$ 3 | 11 | 12.3 | CP Ti 3 | 19 | 17 |
| | 5 | | | 13 | | | 17 | |
| | 8 | | | 13 | | | 15 | |
| Baseline 4 | 8 | 8.7 | $Al_2O_3$ 4 | 11 | 13 | CP Ti 4 | 15 | 14.7 |
| | 10 | | | 15 | | | 12 | |
| | 8 | | | 13 | | | 17 | |
| Baseline 5 | 9 | 8 | $Al_2O_3$ 5 | 11 | 14.7 | CP Ti 5 | 17 | 17.3 |
| | 7 | | | 16 | | | 16 | |
| | 8 | | | 17 | | | 19 | |
| Baseline 6 | 9 | 7.3 | $Al_2O_3$ 6 | 15 | 17 | CP Ti 6 | 13 | 14.3 |
| | 7 | | | 16 | | | 15 | |
| | 6 | | | 20 | | | 15 | |
| Overall Ave. | | 9.1 | | | 14.7 | | | 16.1 |

Immunohistochemistry

Qualitative analysis of the T-cells was performed by evaluating the immunohistochemistry stained samples for the amount of red color. Baseline, $Al_2O_3$, CP Ti, Ti-15Al-33Nb, and Ti-21Al-29Nb-treated calvaria slides were observed using the OM at 40×magnification, see FIGS. 27A to 27E. As the baseline samples had not been treated with the particles, one might expect a minimal number of T-cells in these samples. In agreement with theory, the baseline slides exhibmore inflammation and bone deterioration and indicate poor biocompatibility. Table 9 shows that CP Ti particles stimulate 100-fold more TNFα than untreated macrophages. The $Al_2O_3$ and both Ti—Al—Nb alloys induced slight increases in TNFα concentration compared to the untreated macrophages but significantly less than CP Ti particles ($p=0.01$). These results agree with the animal studies, showing that the CP Ti particles are the most reactive and that the two different Ti—Al—Nb alloys exhibit similar behavior and show promise as potential implant materials.

TABLE 9

TNFα stimulation as a function of particle type.

| Particle Type | Dose | Peak TNFα level (pg/mL) |
|---|---|---|
| None | | 12.8 |
| CP Ti | 10^7 particles/mL | 1175 |
| Alumina | 0.001 M | 42.8 |
| Ti—15Al—33Nb | 0.01 M | 25.5 |
| Ti—21Al—29Nb | 0.01 M | 25 |

Summary and Conclusions

The degree of biocompatibility of the novel Ti—Al—Nb alloys investigated were evaluated and compared to that for CP Ti and $Al_2O_3$. Particle-treated calvaria underwent several tests to observe the deterioration of the bone, presence of osteoclasts, and T-cells. The various stains used were methylene blue/acid fuchsin, TRAcP, and immunohistochemistry. Overall, the Ti—Al—Nb alloys reacted favorably with mouse hard and soft tissue forming a solid coherent interface without significant cell swelling. The biocompatibility experiments involving measuring the resorption of mouse calvarial tissue in response to the Ti—Al—Nb particles, indicated that no significant detrimental reaction occurs between Ti—Al—Nb alloy particles and living cells. For the particle-treated calvaria, Ti-15Al-33Nb exhibited a midline sagittal suture area comparable to that of untreated mice, and such experiments demonstrated that there is only a small difference in the biological response for this alloy and Ti-21Al-29Nb. Both of these alloys were clearly superior to CP Ti and $Al_2O_3$ with respect to bone deterioration. In the other biocompatibility evaluations, the Ti—Al—Nb alloys exhibited behavior superior to that for CP Ti, thereby demonstrating their capability as feasible biomaterial substitutes for CP Ti. The results did not statistically indicate which of the two alloy compositions was more desirable from a biomedical implant point of view. Overall, it is apparent that Ti—Al—Nb alloys are used for biomedical implant applications.

The following conclusions were obtained from this work:

(1) The Ti-15Al-33Nb and Ti-21Al-29Nb particles adhered well to the mice calvaria without significant detrimental reaction as observed through OM, SEM, and EDS analysis.

(2) With respect to bone deterioration, the ranking for the particles in order from greatest-to-least bone deterioration exhibited was: $Al_2O_3$, CP Ti, Ti-21Al-29Nb, Ti-15Al-33Nb.

(3) The CP Ti particles exhibited a similar number of osteoclasts compared to the $Al_2O_3$ particles for TRAcP stained samples, both of which were greater than the baseline number of osteoclasts.

(4) CP Ti particle treatment resulted in the greatest infiltration of T-cells followed by the Ti-15Al-33Nb and Ti-21Al-29Nb alloys. $Al_2O_3$ particles demonstrated the least infiltration of T-cells.

(5) Macrophages phagocytosed the Ti-15Al-33Nb, Ti-21Al-29Nb, CP Ti, and $Al_2O_3$ particles equally readily with no apparent harm to the cell itself.

(6) The Ti—Al—Nb alloy particles stimulated significantly less TNF than $Al_2O_3$ and CP Ti, where the CP Ti particles exhibited the worst response by stimulating 100-fold more TNFα than untreated macrophages.

Examples For Microstructure, Creep, and Tensile Behavior of a Ti-21Al-29Nb(at. %) Orthorhombic+B2 Alloy The creep and tensile deformation behavior of a Ti-21Al-29Nb(at. %) alloy were studied. Monolithic sheet materials were produced through conventional thermomechanical processing techniques. Heat treatments at all temperatures above 1050° C., followed by water quenching, resulted in fully-B2 microstructures. Below 1050° C., either equiaxed or Widmanstätten O-phase precipitated within the B2 grains. RT elongation-to-failure values of less than 2% were recorded for aged microstructures containing 72-78 volume percent O phase. Tensile-creep experiments were conducted in the temperature range 650-710° C. and stress range 48-250 MPa. The measured creep exponents and activation energies suggested that the creep mechanisms were dependent on stress and microstructure. Microstructural effects on the tensile properties and creep behavior are discussed and the data was compared to that for other $Ti_2AlNb$-based alloys.

Introduction

Due to the excellent creep resistance of the orthorhombic (O) phase (T. K. Nandy, R. S. Mishra, and D. Banerjee, Creep behavior of an orthorhombic phase in a Ti—Al—Nb alloy, Scr. Metall. Mater. 28 (1993), pages 569-574 and T. K. Nandy and D. Banerjee, The Mechanical Behavior of the Intermetallic $Ti_2AlNb$, in: M. V. Nathal, R. Darolia, C. T. Lium P. L. Martin, D. B. Miracle, R. Wagner, and M. Yamaguchi (Eds.), Structural Intermetallics, The Minerals, Metals, and Materials Society, Warrendale, Pa., 1997, pages 777-786)), $Ti_2AlNb$ intermetallic alloys are being considered for use in elevated-temperature structural applications. The excellent creep resistance of $Ti_2AlNb$ intermetallics is balanced against its low fracture toughness and elongation-to-failure at ambient temperatures (R. G. Rowe et al., Tensile and Creep Behavior of Ordered Orthorhombic $Ti_2AlNb$-Based Alloys, in: L. A. Johnson et al., High Temperature Ordered Intermetallic Alloys IV, The Materials Research Society, Pittsburgh, Pa., 1991, pages 703-708 and C. J. Boehlert, Part III. The Tensile Behavior of Ti—Al—Nb O+Bcc Orthorhombic Alloys, Metall. Mater. Trans. A. 32 (2001), pages 1977-1988)). This Example describes the physical metallurgy of the Ti-21Al-29Nb(at. %) alloy containing predominately the orthorhombic and ordered body-centered cubic (BCC), B2, phases. All alloy compositions are given in atomic percent. In particular, the microstructural evolution, creep, and tensile behavior are described. The main objective of this work was to understand microstructure-property relationships. The mechanical behavior of various microstructures was compared and both creep and tension deformation mechanisms were studied. In particular, microstructural observations of the deformation behavior and calculated creep parameters based on the secondary creep rate were characterized. The understanding gained from the mechanical behavior was then applied to develop microstructure-property relationships. The creep and tensile behavior of Ti-21Al-29Nb was compared with that of O-dominated alloys, such as Ti-25Al-24Nb, Ti-22Al-27Nb, and Ti-23Al-27Nb, in order to provide additional insight to the microstructure-property relationships of higher Al containing O+B2 alloys.

Experimental

Deformation processing was performed on a double vacuum arc remelted (VAR) Ti-21Al-29Nb ingot, which was processed by RMI Titanium Company (Niles, Ohio, now RTI International Metals, Inc.). The ingot was heated at 982° C., which is below the BCC-transus, then unidirectionally forged to an approximately 3:1 ratio. The forged pancake exhibited a significant amount of exterior cracks, and therefore, the initially planned further attempts at forging were conceded. Instead, subtransus hot rolling was used to further breakdown the cast structure. Slabs of 127 mm×19.05 mm×25.4 mm were cut from the forgings and isothermally soaked at 982° C. prior to rolling. Unidirectional multipass rolling was carried out with interpass reheating at 982° C. for 5 minutes. The reduction per pass ranged between 5-10% and the total reduction was approximately 90%. The total effective true shear strain which the original cast ingot underwent was calculated to be on the order of two. The final thickness of the sheet was approximately 1.5 mm. Overall, this alloy was less amenable to subtransus processing than lower Al containing Ti—Al—Nb alloys (C. J. Boehlert, Microstructure, creep, and tensile behavior of a Ti-12Al-38Nb (at. %) beta+orthorhombic alloy, Mater. Sci. Eng. A 267 (1999), pages 82-98). However, it is possible to process this alloy at subtransus temperatures enabling the possibility of obtaining a wide range of microstructures, containing varying phase volume fractions, grain sizes, and morphologies, through post processing heat treatment similar to other Ti—Al—Nb alloys (C. J. Boehlert and J. F. Bingert, Microstructure, Tensile, and Creep Behavior of O+BCC $Ti_2AlNb$ Alloys Processed Using Induction-Float-Zone Melting, J. Mater. Process. Technol., 117 (2001), pages 401-409 and C. J. Boehlert, B. S. Majumdar, V. Seetharaman, and D. B. Miracle, Part I. The microstructural Evolution in Ti—Al—Nb O+BCC Orthorhombic Alloys, Metall. Mater. Trans. A. 30 (1999), pages 2305-2323).

Samples for the phase evolution study were diamond-saw cut from the rolled sheet, then cleaned and wrapped in tantalum foils prior to being subjected to solution treatments at temperatures between 855-1105° C., followed by water quenching. Other samples were subjected to similar solution heat treatments followed by furnace cooling (10° C./min) to 855° C., a hold for 8 hours at that temperature, control cooling (1° C./min) to 650° C., then furnace cooling to RT. This heat treatment was used in order to study the aging transformation behavior. The two (2) microstructures produced through this heat-treatment schedule will henceforth be referred to by their solutionizing temperatures: HT:960 and HT:1005. The chemical composition of the as-processed material was determined using Inductively Coupled Plasma Optical Emission Spectroscopy (ICP-OES) and Inert Gas Fluorescence (IGF). Grain size (d) was determined using the line-intercept method according to ASTM standard E112 ("Standard Test Methods for Determining Average Grain Size," ASTM Designation E112-96e3. American Society for Testing and Materials, West Conshohocken, Pa. (1996), and phase volume fractions were determined quantitatively using NIH image analysis software on digitized, high contrast, backscattered-electron (BSE) images taken using an AMRAY 1810 scanning electron microscope (SEM). Differential thermal analysis (DTA) was performed to estimate the BCC-transus temperature.

Blanks from the heat-treated sheet materials were machined, using either electrodischarge machining (EDM) or a mill, into a flat dogbone geometry used for tensile and tensile-creep specimens. Four (4) open-air creep experiments were performed on a vertical Applied Test System, Incorporated (ATS) load frame having a 20:1 lever-arm ratio. The testing temperatures and stresses ranged between 650° C.-710° C. and 48-250 MPa, respectfully. Although the experiments used a constant load, in most cases the reduction in cross-sectional area was not sufficient to significantly alter the stress. Therefore, the stresses were assumed to be constant. Creep strain was monitored during the tests using a linear variable differential transformer (LVDT) that was connected to a 25.4 mm gage length ATS high-temperature extensometer. The extensometer was attached directly to the gage length of each sample. The resolution of the strain measuring capability of the LVDT was 0.0001 mm/mm. The strain rate resolution was estimated to be 2.8E-9 $s^{-1}$ according to the resolution of the strain measurement technique. Specimen temperatures were monitored by three chromel-alumel type K thermocouples located within the specimen's reduced section. Targeted temperatures were maintained within ±5° C. All creep specimens were loaded parallel to the rolling direction, and the experiments were conducted such that the specimens were soaked at the creep temperature for at least 60 minutes prior to applying load in order to equilibrate the thermal stresses. After the creep strain had proceeded well into the secondary regime, either the load or temperature was changed or the creep test was discontinued. The tested specimens were cooled under load to minimize recovery of the deformed structures. Selected specimens were taken to failure. Six (6) tension experiments were performed in air at RT and 650° C. at a strain rate of $10^{-3}$ $s^{-1}$ using an Instron 8562 mechanical testing machine. An Instron extensometer, attached directly to the gage length of each sample, was employed to measure strain.

Results

Microstructure

Figure 29A:
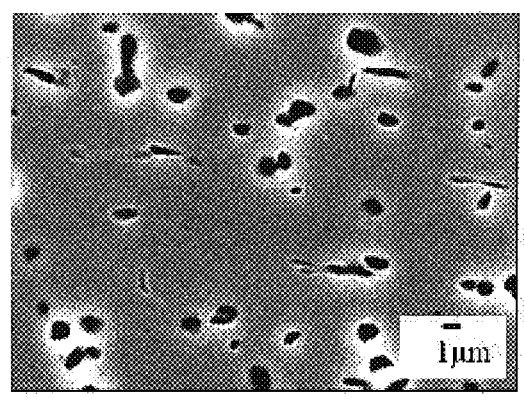
FIGS. 29A shows a secondary electron SEM image of the as-processed Ti-21Al-29Nb microstructure.
Figure 29B:
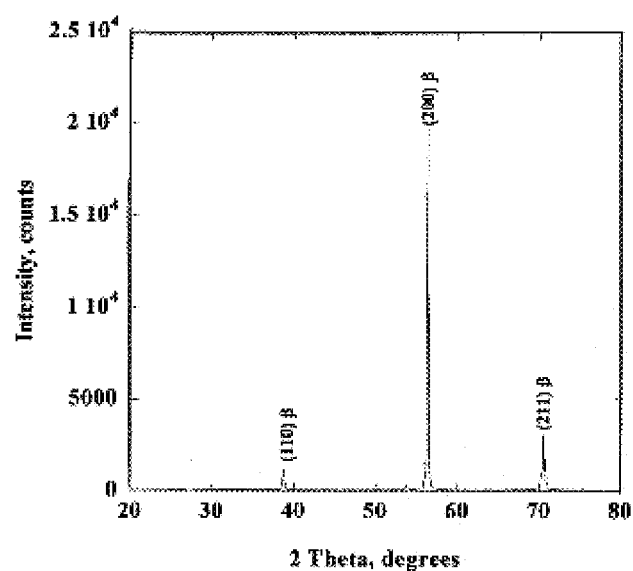
FIG. 29B shows an XRD pattern of 1075° C./3h/WQ heat-treated sample.
Figure 29C:
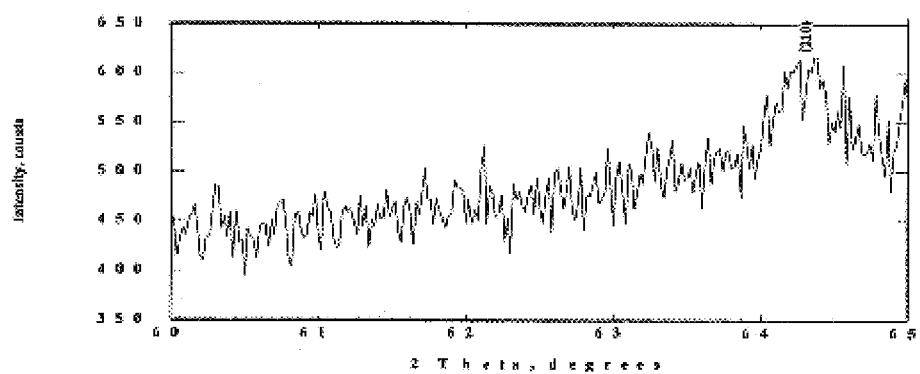
FIG. 29C shows long count time scan XRD pattern taken from the same sample in FIG. 29B. Note the presence of the (210) superlattice reflection in FIG. 29C.

The measured composition of the sheet material is provided in Table 10 and a secondary electron (SE) SEM image of the As-Processed (AP) sheet is depicted in FIG. 29A, where the B2 phase is the light phase and the $\alpha_2$ phase is the dark phase. The ordered B2 phase was identified by the (210) superlattice reflection present in the XRD pattern (see FIGS. 29B and 29C).

TABLE 10

Chemical Analysis of the As-Processed Sheet

| Atomic percent | | | weight parts per million | | |
|---|---|---|---|---|---|
| Ti | Al | Nb | N | Fe | O |
| Bal | 20.6 | 28.7 | 110 | 2000 | 790 |

Figure 30:
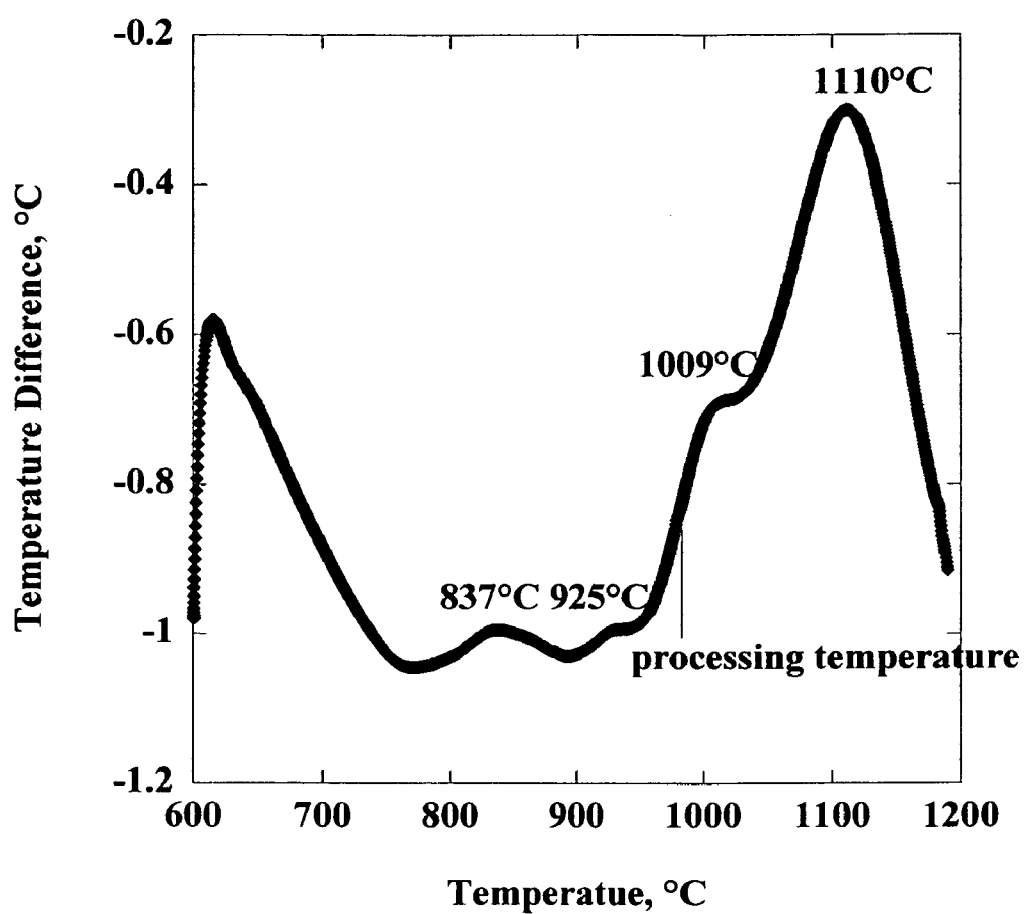
FIG. 30 is a graph of DTA plot of temperature difference versus temperature for the heating portion of the as-rolled sheet. The heating rate was 15° C./minute between 600-1200° C.
Figure 31A:
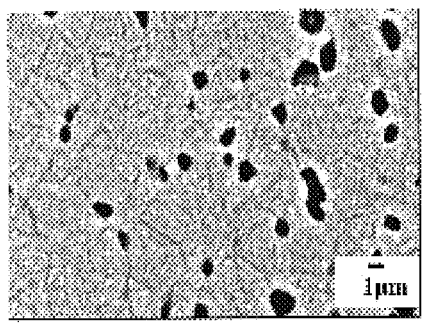
FIGS. 31A to 31E show microstructures solution treated at 855° C.
Figure 31B:
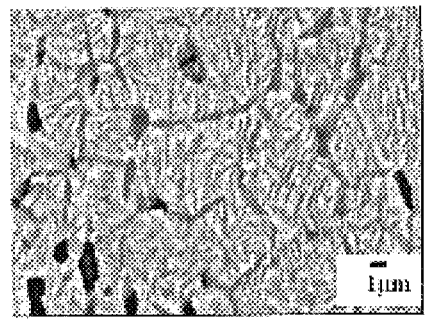
Figure 31C:
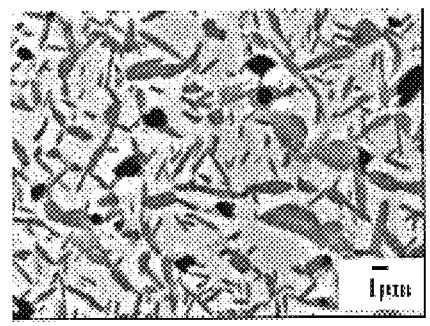
Figure 31D:
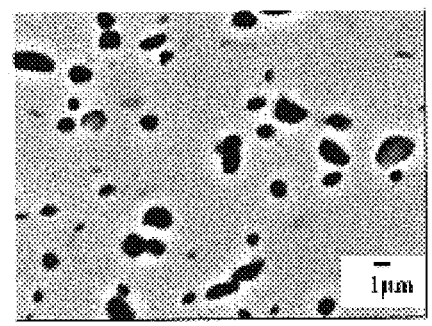
Figure 31E:
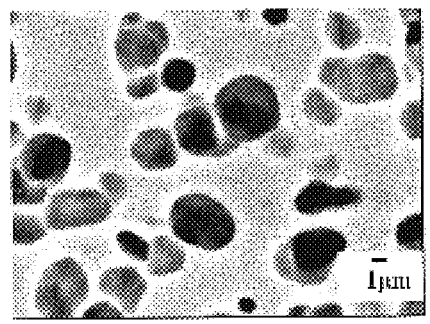

This superlattice reflection occurs at ~64°2θ with a relative intensity ($I/I_o$) of 1 (C. J. Boehlert et al., Processing and Heat Treatment Effects on the Phase Evolution, Tensile, and Creep Behavior of an Orthorhombic Ti-25Al-25Nb Alloy, in: W. O. Soboyejo et al., Deformation and Fracture of Ordered Interetallic Materials III, The minerals, Metals, and Materials Society, Warrendale, Pa., 1996, pages 565-582). The ordered structure was also identified using transmission electron microscopy diffraction patterns. $\alpha_2$ grains were evident in the as-rolled material indicating that 982° C. is within the two-phase ($\alpha_2$+B2) or three-phase ($\alpha_2$+B2+O) fields. DTA, using 15° C./minute heating and cooling rates, identified the BCC transus to lie between 1009-1100° C. and indicated that several phase transformations occurred between 600-1200° C., see FIG. 30. Based on the disappearing-phase method, the B2→B2+O transus was estimated to be slightly less than 1050° C. as a small volume of the $\alpha_2$ phase was observed for the 1005° C. condition, and above 1050° C., fully B2 microstructures were observed. Thus, the estimated temperature range of the phase fields, proposed from the DTA and solution-treatment study data, is: B2>1040° C., 990° C.<$\alpha_2$+B2<1040° C., 960° C.<$\alpha_2$+B2+O<990° C., and O+B2<960° C. The corresponding grain sizes and phase volume fractions for the solution treated and water-quenched samples along with the aged samples are listed in Table 11.

TABLE 11

Heat Treatment Schedules and the Corresponding Microstructural Parameters

| Heat Treatment, °C. | $\alpha_2$ Vp | O Vp | B2 Vp | d* (μm) |
|---|---|---|---|---|
| AP | 4 | 0 | 96 | 3 |
| 855/3 h/WQ | 4 | 83 | 13 | 5 |
| 910/3 h/WQ | 3 | 50 | 47 | 5 |
| 960/3 h/WQ | 1 | 38 | 61 | 8 |
| 990/3 h/WQ | 6 | 0 | 94 | 7 |
| 1005/3 h/WQ | 5 | 0 | 95 | 12 |
| 1050/3 h/WQ | 0 | 0 | 100 | 135 |
| 1075/3 h/WQ | 0 | 0 | 100 | 150 |
| 1105/3 h/WQ | 0 | 0 | 100 | 196 |
| HT: 960 | 0 | 72 | 28 | 8 |
| HT: 1005 | 5 | 78 | 17 | 12 |

Figure 32A:
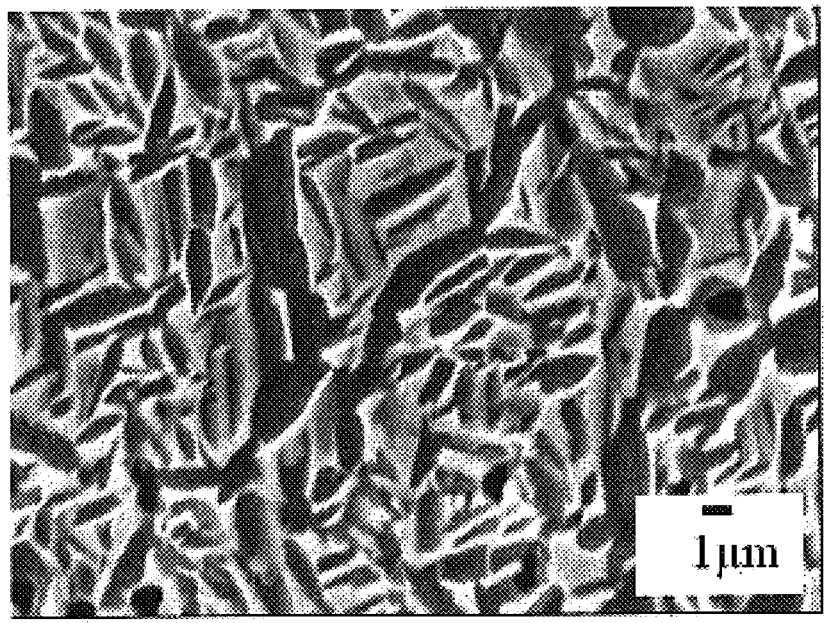
FIGS. 32A and 32B show solution-treated-and-aged microstructures.
Figure 32B:
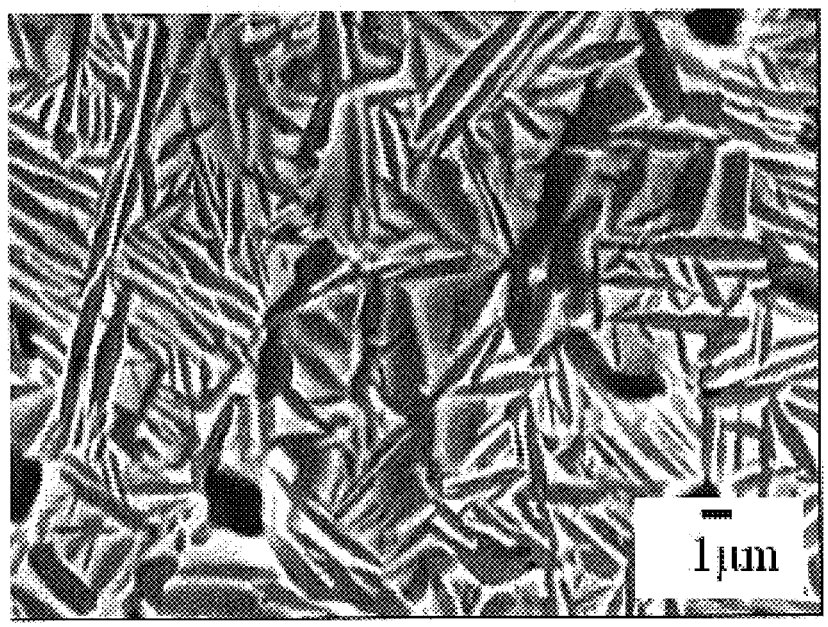

WQ: water quenched
*d represents the equiaxed grain size independent of phase.
Vp: volume percent
AP = as processed Increasing the solutionizing temperature above the BCC-transus resulted in larger equiaxed B2 grains. FIGS. 31A to 31E display microstructures that were solution treated within the O+B2 and $\alpha_2$+B2 phase fields followed by water quenching. Aging treatments were performed in order to identify morphological differences and O-phase volume fractions at lower temperatures. Similar to that found previously (C. J. Boehlert et al (1999), ibid), the morphology of the O-phase was related to aging temperature. Above 910° C. equiaxed, O-phase grains were possible whereas below 910° C., the O-phase precipitated as laths. BSE SEM images of the HT:960 and HT:1005 microstructures are depicted in FIGS. 32A and 32B. It is noted that each of these microstructures were selected for the mechanical property evaluation discussed later.

Figure 33:
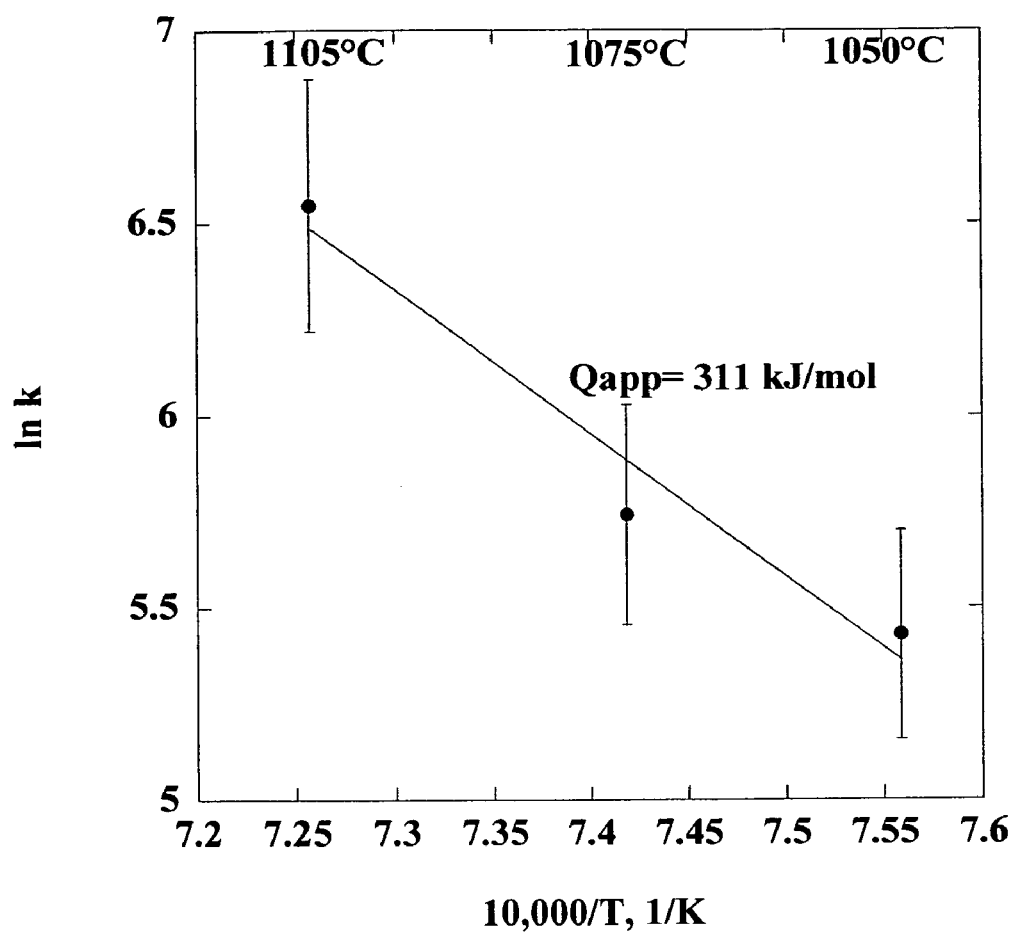
FIG. 33 is a graph showing a plot of ln k vs. (10,000/T), based on equations 1 and 2, depicting the B2 grain grown as a function of the solutionizing temperature.

The B2 grain size could be significantly varied using super-transus heat treatments followed by water quenching. Under isothermal heat-treatment conditions, normal grain growth for single-phase materials is well described by the following empirical equation (H. Hu and B. B. Rath, On the Time Exponent in Isothermal Grain Growth, Metall. Trans. 1 (1970) pages 3181-3184 and V. Seetharaman and S. L. Semiatin, Plastic Flow and Microstructure Evolution During Hot Deformation of a Gamma Titanium Aluminide Alloy, Metall. Mater. Trans. A. 28 (1997), pages 947-954)):

$$d^n - d_o^n = kt \quad (1)$$

where n is the grain growth exponent, d is the heat-treated B2 grain size, $d_o$ is the pre-heat treated grain size and in this case the B2 grain size of the as-rolled sheet, and t is the annealing time. The variable k is estimated by the Arrhenius equation:

$$k = k_o \exp(-Qapp/RT) \quad (2)$$

where $k_o$ is a kinetic constant, Qapp is the activation energy for grain growth, R is the gas constant, and T is absolute temperature. For most single-phase metals, the value of n ranges between 2-10 due to the drag force exerted by solute atoms on grain boundaries (G. T. Higgins, S. Wiryolukito, and P. Nash, Grain Growth in Polycrystalline Materials, Trans Tech Publications, Aedermannsdorf, Switzerland, 1992). Taking n=3, the corresponding values of k are represented on the in k versus (1/T) plot depicted in FIG. 33. For grain growth above 1050° C., Qapp is approximately 311 kJ/mol, which is significantly larger than that predicted from the diffusion coefficients of the binary Ti—Nb system presented by Shewmon (P. G. Shewmon, Diffusion in Solids, McGraw-Hill, New York, N.Y., (1963); the calculated Qapp for Ti-29Nb was approximately 185 kJ/mol. Thus, Al concentrations of more than 20 at. % significantly affect the diffusion rates and increase the Qapp value.

Tension

Properties

The RT tensile properties, including 0.2% yield strength (YS), ultimate strength (UTS), elongation-to-failure ($\epsilon_f$), and modulus (E), for selected microstructures are listed in Table 12.

TABLE 12

RT Tensile Properties

Figure 34:
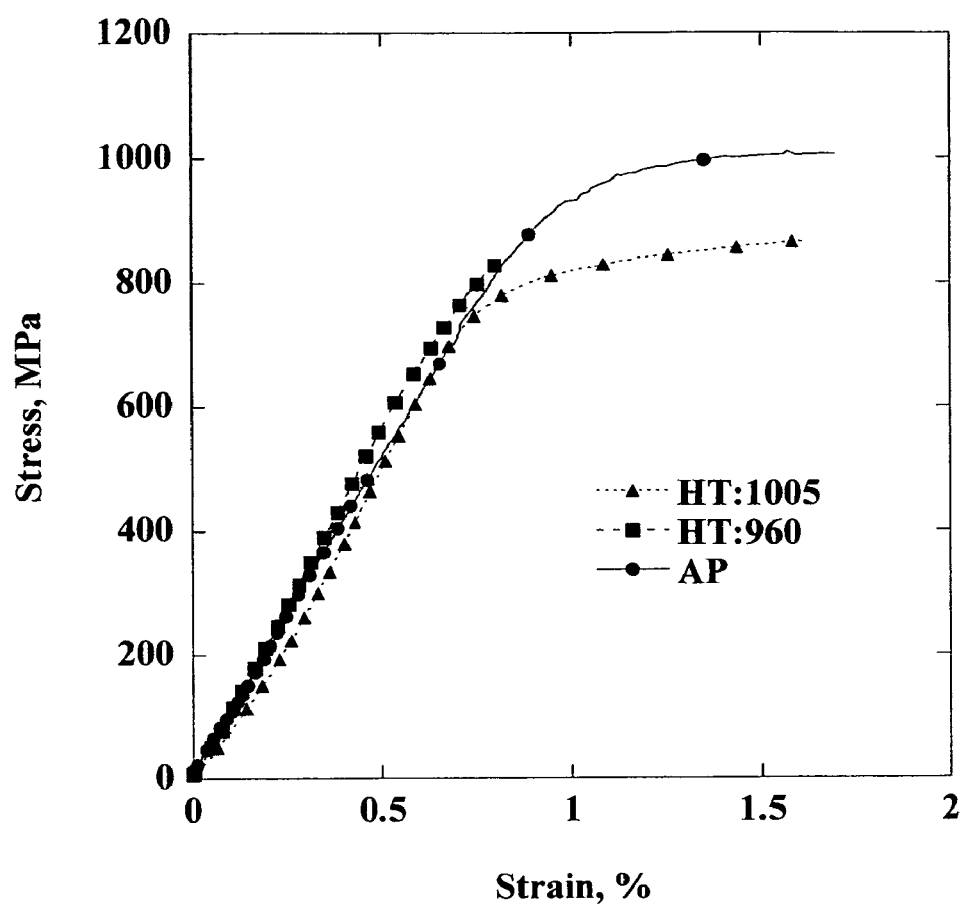
FIG. 34 is a graph of stress versus strain plots for the AP and heat-treated samples at RT.
Figure 35:
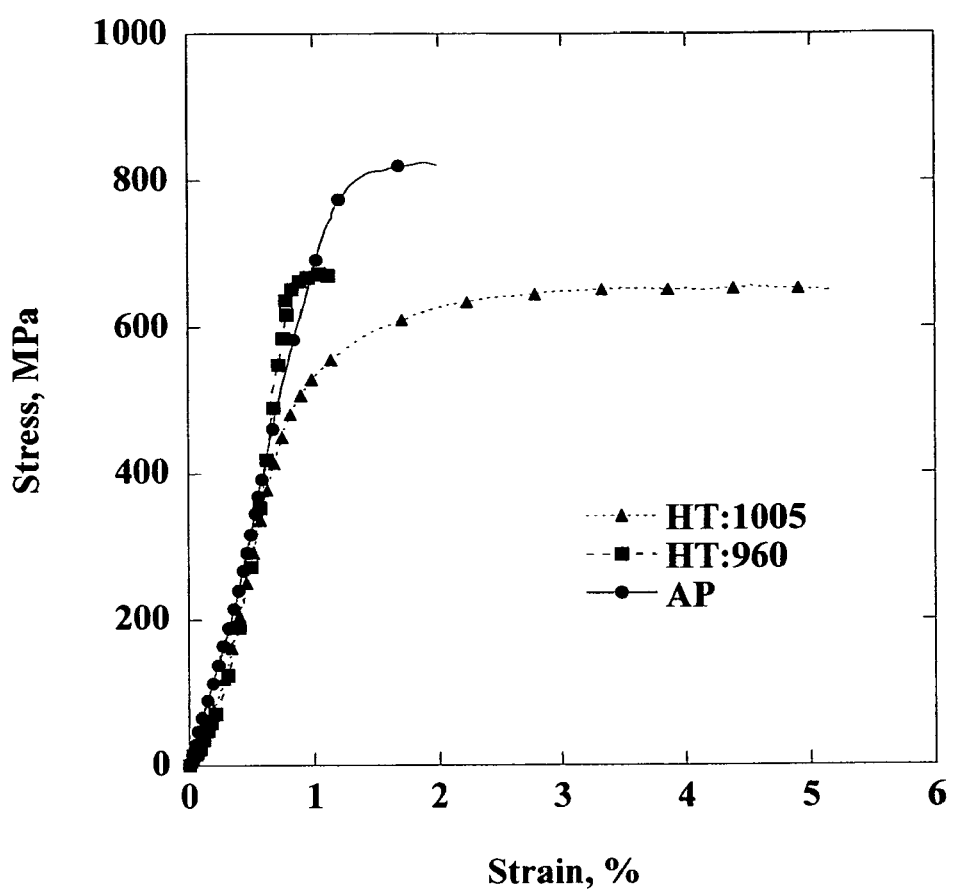
FIG. 35 is a graph showing the stress versus strain plots for the AP and heat-treated samples at 650° C.

| Heat Treatment, °C. | E, GPa | 0.2% YS, MPa | UTS, MPa | $\epsilon_f$, % |
|---|---|---|---|---|
| AP | 103 | 972 | 1010 | 1.7 |
| HT: 960 | 112 | n/a | 830 | 0.8 |
| HT: 1005 | 115 | 803 | 868 | 1.6 | n/a indicates 0.2% proportionality requirement was not met
RT = Rain Temperature
AP = As Processed The AP material exhibited the greatest volume fraction of B2 phase and the correspondingly highest $\epsilon_f$ value. This is depicted in FIG. 34 which compares the RT tensile stress-strain curves for the AP and heat-treated microstructures evaluated. In each sample, RT $\epsilon_f$ values of less than 2% were measured. The 650° C. tensile results (see Table 13) are shown in FIG. 35 and the trends were similar to those at RT; however, each of the samples exhibited lower strength and higher $\epsilon_f$ values than at RT.

TABLE 13

650° C. Tensile Properties

| Heat Treatment, °C. | E, GPa | 0.2% YS, MPa | UTS, MPa | $\epsilon_f$, % |
|---|---|---|---|---|
| AP | 71 | 810 | 825 | 2.0 |
| HT: 960 | 82 | 656 | 664 | 1.6 |
| HT: 1005 | 77 | 537 | 657 | 5.2 |

Deformation Behavior

Figure 36A:
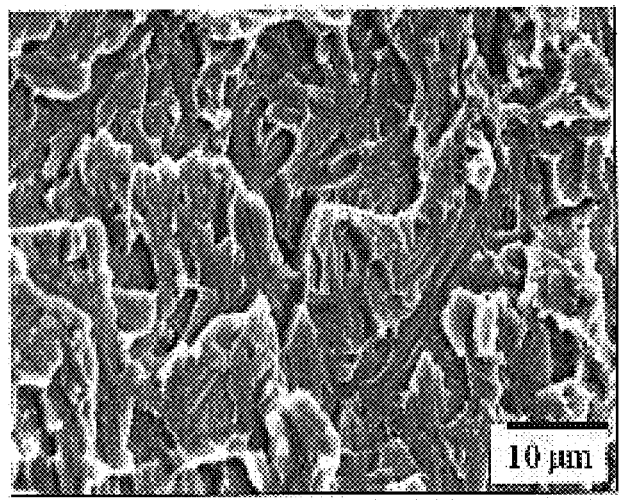
FIGS. 36A and 36B are photomicrographs showing fracture surface of a HT:1005 sample after RT (FIG. 36A) and 650° C. tensile failure (FIG. 36B). Note the cleavage and faceted fracture evident throughout this O-phase dominated microstructures, particularly at RT.
Figure 36B:
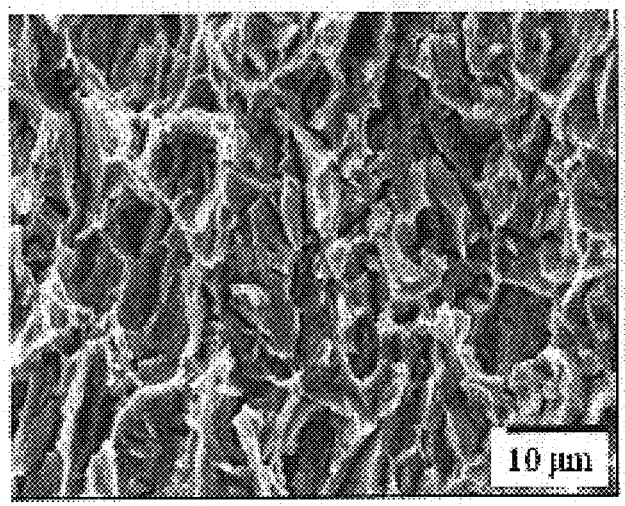

Tensile fracture surfaces of the specimens depicted the brittle characteristics of the O phase, see FIGS. 36A and 36B. Cleavage and faceted fracture were evident throughout. In addition, the specimens exhibited a flat fracture characteristic of brittle metals (R. W. Hertzberg, Deformation and Fracture Mechanics of Engineering Materials, Fourth Edition, John Wiley and Sons, New York, N.Y., 1996). Selected RT specimens, which were metallographically polished prior to testing, exhibited little evidence of surface slip.

Creep Behavior

Properties

The creep strain-life behavior resembled that for most pure metals and alloys (R. W. Evans and B. Wilshire, Creep of Metals and Alloys, The Institute of Metals, New York, N.Y., 1985), where the primary, secondary, and tertiary stages were each present. The minimum creep rate was determined from the following creep law equation:

$$\epsilon_{min} = B\sigma^n \quad (3)$$

where B is a constant, σ is the applied stress, and n is the creep stress exponent. Table 14 lists the testing conditions, $\epsilon_{min}$, and d for each of the heat-treated specimens tested.

TABLE 14

Creep Properties for Heat-Treated Microstructures

| Heat Treatment, °C. | σ/T (MPa/°C.) | $\dot{\epsilon}$ min (s$^{-1}$) | B2 d (μm) |
|---|---|---|---|
| HT: 960 | 48/650 | 4.57E−09 | 8 |
| HT: 960 | 48/710 | 1.01E−08 | 8 |
| HT: 960 | 73/650 | 7.02E−09 | 8 |
| HT: 960 | 77/710 | 1.49E−08 | 8 |
| HT: 960 | 99/650 | 7.64E−09 | 8 |
| HT: 960 | 122/650 | 1.16E−08 | 8 |
| HT: 960 | 148/650 | 1.50E−08 | 8 |
| HT: 960 | 170/650 | 1.98E−08 | 8 |
| HT: 1005 | 48/650 | 3.63E−10 | 12 |
| HT: 1005 | 73/650 | 6.31E−10 | 12 |
| HT: 1005 | 100/650 | 3.18E−09 | 12 |
| HT: 1005 | 126/650 | 3.74E−09 | 12 |
| HT: 1005 | 148/650 | 6.54E−09 | 12 |
| HT: 1005 | 148/670 | 8.93E−09 | 12 |
| HT: 1005 | 148/690 | 1.65E−08 | 12 |
| HT: 1005 | 148/710 | 3.60E−08 | 12 |
| HT: 1005 | 172/650 | 1.10E−08 | 12 |
| HT: 1005 | 225/650 | 3.80E−08 | 12 |
| HT: 1005 | 250/650 | 5.93E−08 | 12 |

Figure 37:
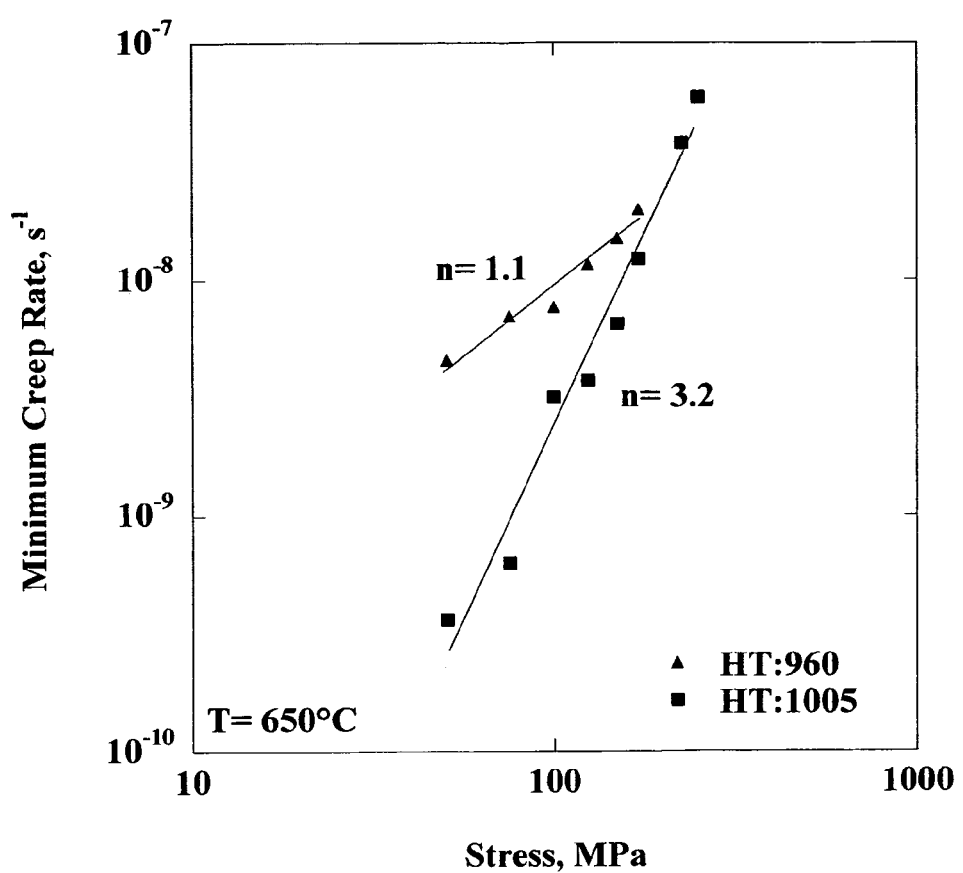
FIG. 37 is a graph showing Log $\epsilon_{min}$ vs log σ curves at T=650° C. for the different heat-treated conditions.
Figure 38:
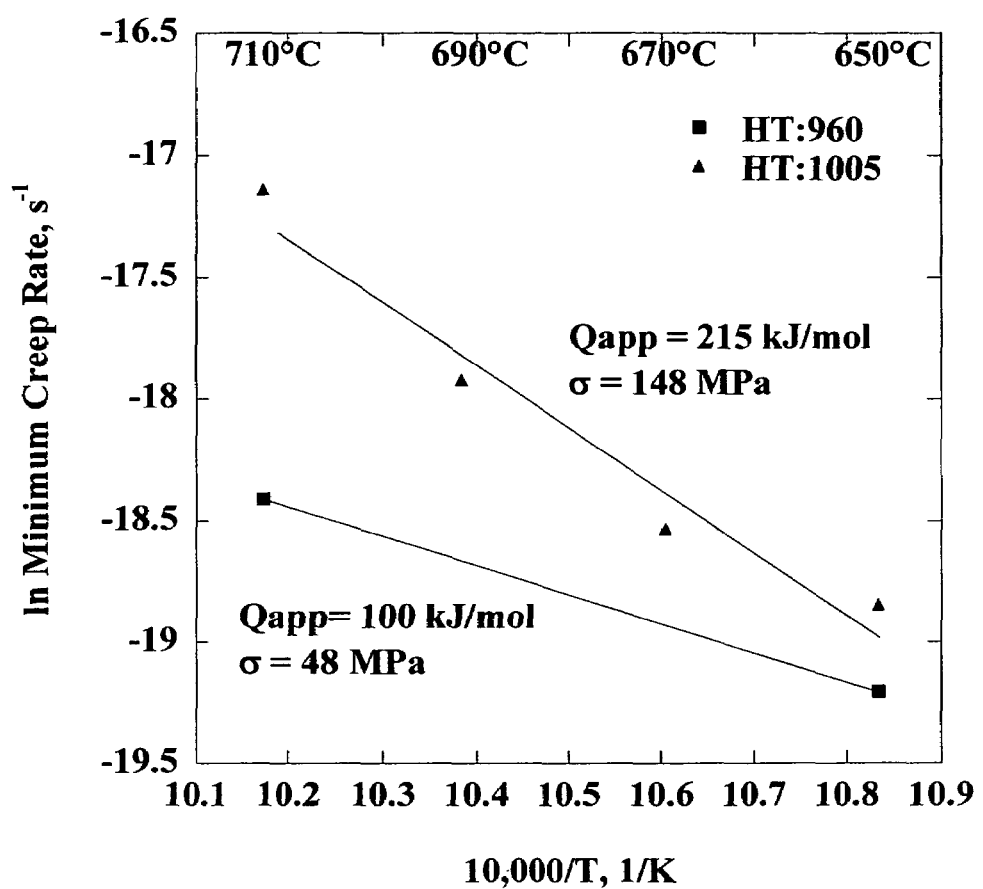
FIG. 38 is a graph showing temperature dependence of $\epsilon_{min}$ at 48 MPa for the HT:960 sample and 148 MPa for the HT:1005 sample.

The HT:1005 microstructure outperformed the HT:960 microstructure. Thus, minimum creep rates decreased with increasing grain size from 8 to 12 μm and increasing O-phase volume fraction from 0.72 to 0.78. The creep parameter data suggested that different creep mechanisms exist for each microstructure. Table 15 summarizes the creep parameter data, while FIGS. 37 and 38 show plots of the $\epsilon_{min}$ dependence on stress and temperature, respectively.

TABLE 15

Creep Exponents and Apparent Activation Energies

| Heat Treatment, °C. | σ/T, MPa/°C. | N | σ/T, MPa/°C. | Qapp, kJ/mol |
|---|---|---|---|---|
| HT: 960 | 48–170/650 | 1.1 | 48/650-710 | 100 |
| HT: 1005 | 48–250/650 | 3.2 | 148/650-710 | 215 |

For the HT:960 microstructure the n value was 1.1 over the stress range of 48-170 MPa. The Qapp value was 100 kJ/mol for a creep stress of 48 MPa, which fits within the range expected for grain boundary diffusion of O+BCC alloys, noting that Qapp for grain boundary diffusion is roughly half that for lattice bulk diffusion (T. K. Nandy et al (1993), ibid; T. K. Nandy et al (1997), ibid; C. J. Boehlert (1999), ibid; R. W. Hertzberg (1996), ibid; R. W. Evans et al., (1985), ibid; and T. K. Nandy, R. S. Mishra, A. K. Gogia, and D. Banerjee, The effect of Aluminum on the creep behavior of titanium aluminide alloys, Scr. Metall. Mater. 32 (1995), pages 851-860)). The latter observation is based on previously determined activation energies considered to be representative of lattice bulk diffusion for O+BCC alloys (T. K. Nandy et al (1993), ibid; T. K. Nandy et al (1997), ibid; and T. K. Nandy et al (1995), ibid)). For the HT:1005, the creep stress exponent value was 3.2 over a stress range of 48-250. An activation energy of 215 kJ/mol was determined at 148 MPa which is over twice that measured for the HT:960 sample at 48 MPa.

Discussion

Microstructure

Figure 39:
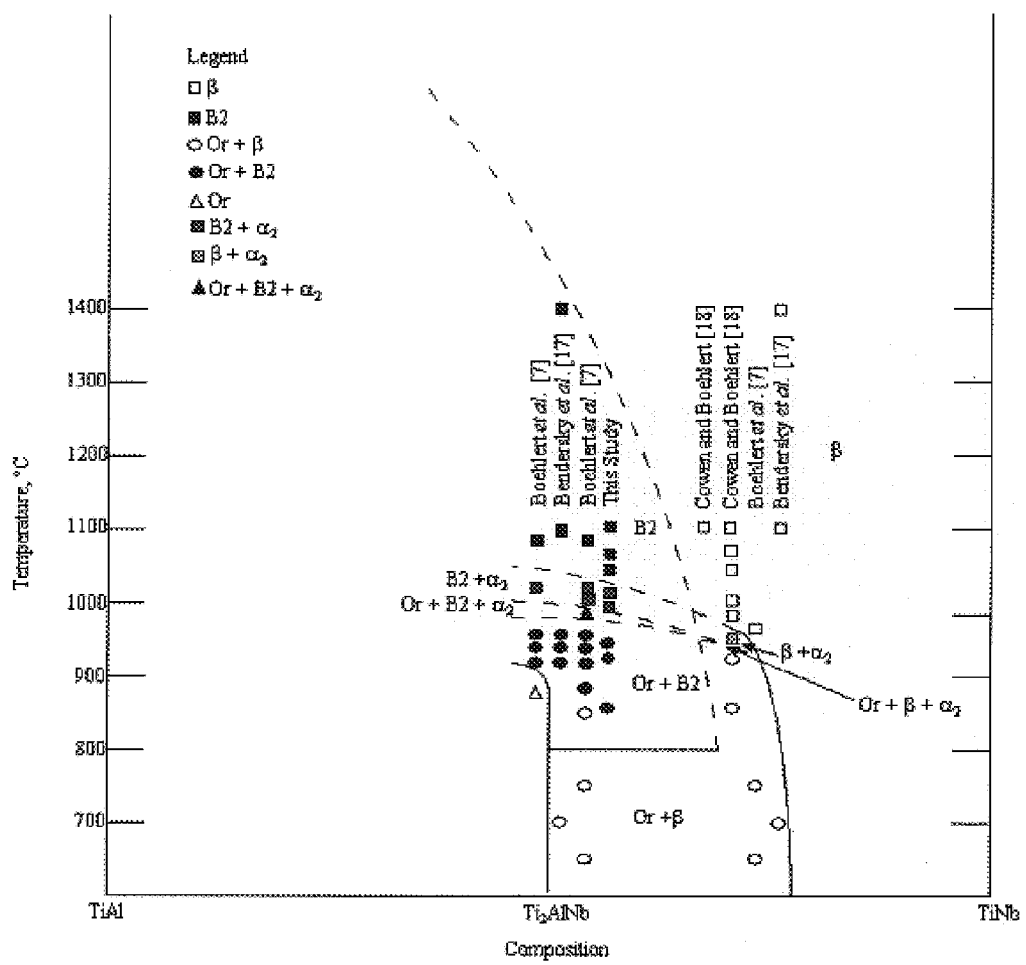
FIG. 39 is a graph showing the pseudobinary section of the Ti—Al—Nb system at 50 at. % Ti taken from Bendersky et al. with data from Ti-21Al-29Nb superimposed. Also included is data for near Ti$_2$AlNb alloys.

Above 1050° C. Ti-21Al-29Nb is fully-B2, yet at lower temperatures the B2-phase stability is reduced and the O phase precipitates. The pseudobinary diagram for the Ti—Al—Nb system with Ti=50 at. % (taken originally from Bendersky et al. (L. A. Bendersky, W. J. Boettinger, and A. Roytburd, Coherent Precipitates in the BCC/Orthorhombic Two-Phase Field of the Ti—Al—Nb System, Acta Metall. Mater. 39 (1991) and later edited by Boehlert et al. (C. J. Boehlert et al (1999), ibid) and Cowen and Boehlert (C. J. Bowen and C. J. Boehlert, Microstructure, Creep, and Tensile Behavior of a Ti-15Al-33Nb (at. %) Beta+Orthorhombic Alloy, Philosophical Magazine, in print)) is depicted in FIG. 39, and it has been revised based on the Ti-21Al-29Nb phase data. It can be seen that heat-treatment schedules, which dictate the volume fractions of the O and BCC phases, were especially important for obtaining both the O+B2 microstructures involved in the mechanical behavior studies. The temperature ranges for the $\alpha_2$+B2 and α2+B2+O phase fields narrow with increasing Nb and decreasing Al contents. It is noted that for the composition range between TiAl and Ti$_2$AlNb, equilibrium involving the face-centered tetragonal γphase and hexagonal $\alpha_2$ phase was excluded in FIG. 39, and this diagram was approximated as a pseudobinary for simplicity. Precipitation of the O-phase from the parent B2 phase formed a Widmanstätten microstructure and was the dominant transformation mode in Ti-21Al-29Nb for temperatures below 910° C., while for temperatures above 910° C., equiaxed O-phase grains may form. This result has been observed previously for near Ti$_2$AlNb alloys (C. J. Boehlert et al (1999), ibid).

Tension Behavior

The $\epsilon_f$ values were always less than 2% for the RT tensile experiments. The high volume fraction of the O phase was expected to be the probable reason for this behavior as similarly seen for other O-dominated microstructures (C. J. Boehlert (2001), ibid). Compared with the B2 structure, the O-phase suffers from a lower number of available slip systems (F. Popille and J. Douin, The dislocation microstructure in orthorhombic O Ti$_2$AlNb deformed between RT and 800° C., Philosophical. Magazine 73, (1996), pages 1401-1418). Even though the active slip systems between the O and BCC phases are compatible, the limited number of O-phase slip systems is considered to be responsible for the low f values in O-phase dominated microstructures. Strengths greater than 1250 MPa have been recorded for O+BCC microstructures containing higher O-phase volume fractions (R. G. Rowe et al (1991), ibid; C. J. Boehlert (1999); ibid and R. G. Rowe, The Mechanical Properties of Ternary and Quaternary Ti$_2$NbAl-Based Titanium Aluminide Alloys, in: F. H. Froes and I. Caplan (Eds.), Titanium '92 Science and Technology, The Minerals, Metals, and Materials Society, Warrendale, Pa. (1993), pages 343-350)). However, O-phase dominated polycrystalline microstructures have proven to be brittle (R. G. Rowe et al (1991), ibid and C. J. Boehlert (2001), ibid)). Thus, maintaining adequate volume fractions of the BCC phase is necessary for providing ductility. Combining the RT tensile data of this work with those from published works on other O+BCC alloys (see Table 16), the effects of nominal composition and heat-treatment are depicted.

TABLE 16

RT Tensile Properties for O + BCC Alloys

| Alloy Composition (reference) | Heat Treatment | 0.2% YS (MPa) | UTS (MPa) | $\epsilon_f$ (%) |
|---|---|---|---|---|
| Ti—23Al—16Nb | 1050° C./1 h/WQ + 850° C./2 h/FC | 691 | 906 | 14.0 |
| Ti—22Al—23Nb | 1050° C./2 h + 815° C./8 h/FC | 836 | 1111 | 14.8 |
| Ti—23Al—23Nb | 760° C./100 h | 472 | 638 | 4.0 |
| Ti—22Al—20Nb—5V | 815° C./24 h + 760° C./100 h | 900 | 1161 | 18.8 |
| Ti—22Al—24Nb | 815° C./4 h | 1257 | 1350 | 3.6 |
| Ti—22Al—25Nb | 1000° C./1 h/Ar + 815° C./2 h/Ar | 1245 | 1415 | 4.6 |
| Ti—22Al—25Nb | 1125° C./1 h/BC + 815° C./2 h/Ar | 1134 | 1175 | 0.9 |
| Ti—22Al—27Nb | 815° C./1 h/Ar | 1294 | 1415 | 3.6 |
| Ti—25Al—21Nb | 1050° C./1 h/Ar + 815° C./2 h/Ar | 847 | 881 | 0.4 |

WQ: water quench;
FC: furnace cool;
Ar: cooling performed in static argon gas;
BC: brick cooled (1.5° C./sec);
na: not available.

Figure 40:
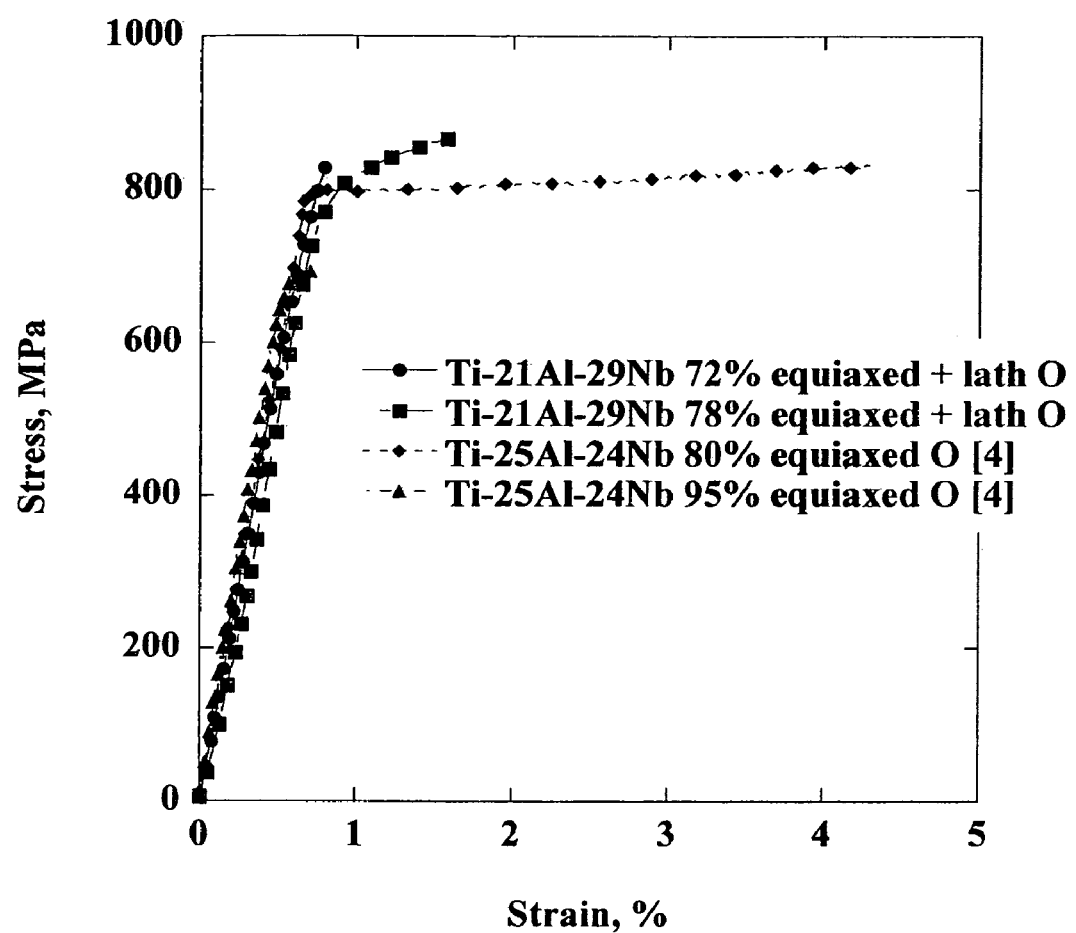
FIG. 40 is a graph showing RT stress versus strain curves for Ti-21Al-29Nb and Ti-25Al-24Nb microstructures.

In general, those alloys containing less Al and more Nb provided greater RT elongations. Nominal composition significantly influences BCC-phase volume fraction, and therefore it is also important for maintaining adequate RT ductility of aged materials. Thus, a balance between strength and ductility must be maintained through proper alloy selection and thermomechanical treatments which control microstructure. FIG. 40 compares the RT tensile stress versus strain curves for Ti-21Al-29Nb and Ti-25Al-24Nb alloy microstructures. For almost equal O-phase volume fractions, the Ti-25Al-24Nb alloy microstructure displayed higher $\epsilon_f$ values and lower strengths than the Ti-21Al-29Nb alloy microstructure. This may be attributed to a morphology difference. The O-phase occurred in an equiaxed morphology in the Ti-25Al-24Nb alloy microstructures, while it predominantly occurred in a lath-type morphology in the Ti-21Al-29Nb alloy microstructures. In the Ti-25Al-24Nb alloy microstructures, the B2 phase was more continuous than that for the Ti-21Al-29Nb alloy, where the laths confined the more ductile B2 phase.

Creep Behavior

For the HT:960 microstructure, the secondary creep behavior was characterized by a stress exponent close to 1, see FIG. 37 and Table 15. The activation energy corresponding to this regime was 100 kJ/mol. It was therefore suggested that the secondary-stage, low-stress regime corresponds to Coble creep, based on the measured creep stress exponent and apparent activation energy. For the HT:1005 microstructure, the secondary-creep behavior was characterized by a stress exponent of 3.2 and the associated Qapp in this regime was 215 kJ/mol. It was therefore suggested that dislocation climb is the dominant creep deformation mechanism for the applied stress range studied. The coarseness of the O-phase laths as well as the O-phase volume fractions were slightly different for the two (2) microstructures tested. It is felt that both the increased grain size and larger volume of O-phase laths, which resulted from the higher-temperature solution treatment, were possible reasons for the greater creep resistance of the HT:1005 sample.

Figure 41:
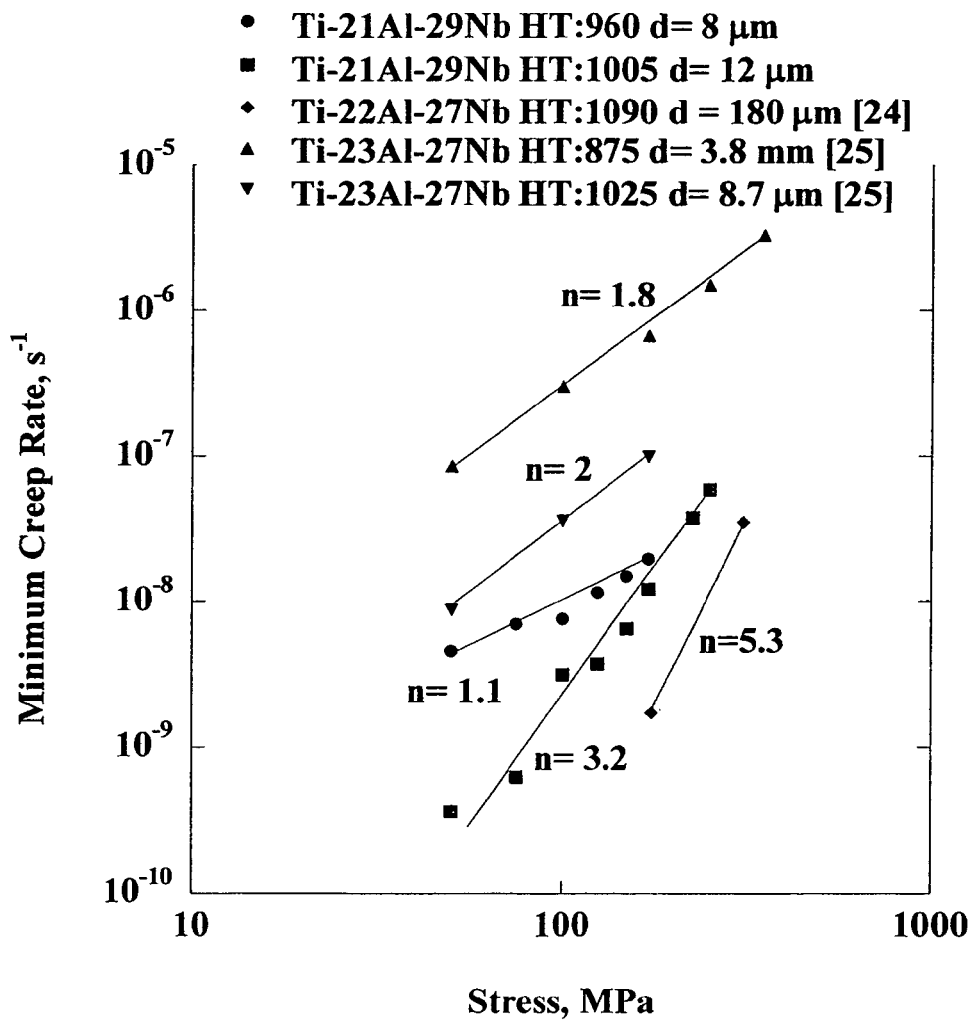
FIG. 41 is a graph showing Log $\epsilon_{min}$ vs log σ behavior of Ti-21Al-29Nb, Ti-22Al-27Nb, and Ti-23Al-27Nb.

In order to gain insight into microstructure-creep relations, the $\log \epsilon_{min}$ vs log σ behavior of the Ti-21Al-29Nb alloy was compared with that of Ti-22Al-27Nb (R. G. Rowe and M. Larsen, The Effect of Microsstructure and Composition on the Creep Behavior of O Phase Titanium Aluminide Alloys, in: P.A. Blenkinsop, W. J. Evans, and H. M. Flowers (Eds.), Titanium 1995, The University Press, Cambridge, UK, 1996, page. 364-371) and Ti-23Al-27Nb (C. J. Boehlert and D. B. Miracle, part II. The Creep Behavior of Ti—Al—Nb O+Bcc Orthorhombic Alloys, Metal. Mater. Trans. A. 30 (1999), pages 2349-2367) alloys (see FIG. 41). Finer equiaxed grain sizes appear to promote higher minimum creep rates and extend stress ranges where n~1-2. Larger grain sizes between 9-12 μm appear to promote lower minimum creep rates. Combining the creep parameter values of this work with those from published works on O, α, and $α_2$-based systems, the similarities and differences of the creep behavior of such alloys are evident. Table 17 compares the n and Qapp values for the different alloys. The data shows that the O alloys exhibit the highest activation energy. For the highest stresses, dislocation climb creep parameters were observed; and for lower stresses, O alloys exhibited creep parameters characteristic of either Coble creep or grain boundary sliding.

TABLE 17

Comparison of Creep Parameters for α, $α_2$ and O-based Ti-Alloys

| Alloy Composition [ref] | Heat Treatment | Test Conditions σ(MPa)/Temp(° C.) | n | Qapp, kJ/mol |
|---|---|---|---|---|
| Low-Stress Regime | | | | |
| Ti [26] α | Various | 1-2/550-865 | 1 | 104-121 |
| Ti—24Al—11Nb $α_2$ | Various | 50-100/575-725, air | 1 | 107-120 |
| Ti—21Al—22Nb | Na | 30-90/650-760, air | 1.4 | na |
| Ti—22Al—23Nb | Na | 69-110/650, air + vacuum | 1.3 | 187 |
| Ti—22Al—23Nb | 996° C./1 hr/AQ | 69-172/650-760, air + argon | 2.8 | 327 |
| Ti—25Al—23Nb | 815° C./1 hr | 175-310/650, argon | 2.8 | na |
| $Ti_2AlNb$ | Various | 50-352/650-760, air + vacuum | 1.8-2.3 | 265 |

TABLE 17-continued

Comparison of Creep Parameters for α, α₂ and O-based Ti-Alloys

| Alloy Composition [ref] | Heat Treatment | Test Conditions σ(MPa)/Temp(° C.) | n | Qapp, kJ/mol |
|---|---|---|---|---|
| Ti—21Al—29Nb [present study] High-Stress Regime | HT: 960 | 48-170/650-710, air | 1.1 | 100 |
| Ti α | Various | 1-2/550-865 | 4.3 | 241 |
| Ti₃Al α₂ | 1000° C./4 h/FC | 138-312/650-800 | 4.3 | 206 |
| Ti-24Al—11Nb α₂ | Various | 100-400/575-725, air | 5 | 260 |
| Ti—27Al—21Nb | 1170° C./OQ + 900° C./AQ | 240-500/650-750, air | 5-6 | 340 |
| Ti—24Al—16Nb | 1150° C./2.5° C./s + 750° C./AQ | 150-540/700-750, air | 4.2-4.3 | 371 |
| Ti—27Al—16Nb | 1170° C./2.5° C./s + 750° C./AQ | 240-660/700-750, air | 4.2-4.3 | 376 |
| Ti—22Al—27Nb | 815° C./1 hr | 310-380/650, argon | 5.3 | na |
| Ti₂AlNb | Various | 317-442/650-760, air | 3.7-5.1 | 346 |
| Ti—21Al—29Nb [present study] | HT: 1005 | 48-250, 650-710, air | 3.2 | 215 |

AQ: air quench;
OQ: oil quench;
FC: furnace cooled;
Ar: cooling performed in static argon gas;
na: not available.

Summary

The physical metallurgy of an O+B2 Ti-21Al-29Nb alloy is described. In particular, the microstructural evolution, creep, and tensile behavior were investigated. Above 1050° C., fully-B2 microstructures formed and the sizes of the B2 grains were controlled by the solutionizing temperature and hold time. No disordered β phase was present. In terms of the RT tensile behavior, the as-rolled microstructure was the strongest (1010 MPa). Aging, which resulted in O-phase volume fractions of up to 0.78, provided low elongations-to-failure.

The secondary-creep behavior was used to suggest the active creep mechanisms. Coble creep characteristics, including stress exponents close to 1 and activation energies resembling grain boundary diffusion were exhibited for the HT:960 microstructure. For the HT:1005 microstructure, a creep-stress-exponent value typical of dislocation climb was determined. Based on the calculated activation energies, the activation energy for lattice self diffusion in the Ti-21Al-29Nb alloy is estimated to be 215 kJ/mol. Overall, the Ti-21Al-29Nb alloy shows promise for structural application. Further processing by thermal hot rolling can reduce or eliminate brittleness. Its greatest downfall appears to be its low ductility due to the presence of high O-phase volume fractions.

Preferably, the alloys contain 0.001 to 5% boron by atoms (atomic percent). The boron acts as a strengthener and reduces gram size (gram refiner) by forming borides.

It is intended that the foregoing description be only illustrative of the present invention and that the present invention be limited only by the hereinafter appended claims.

I claim:

1. A method for forming a finished implant prosthesis which comprises:
   (a) providing an unforged alloy consisting essentially of Ti(x %)Al(y %)Nb wherein x is between about 45 to 54% by atoms, y is between about 15 to 25% by atoms and the balance is niobium;
   (b) forging the alloy at an elevated temperature below a melting point of the alloy in a shape which is an implant preform; and
   (c) machining the implant preform to provide a machined implant; and
   (d) finishing the exposed surfaces of the implant so as to provide the exposed surfaces with a finish which provides biocompatibility, to thereby form the implant prosthesis.

2. The method of claim 1 wherein the alloy is Ti-15Al-33Nb.

3. A method for forming a finished implant prosthesis which comprises:
   (a) providing an unforged alloy of Ti-21Al-29Nb;
   (b) forging the alloy at an elevated temperature below a melting point of the alloy in a shape which is an implant preform; and
   (c) machining the implant preform to provide a machined implant; and
   (d) finishing the exposed surfaces of the implant so as to provide the exposed surfaces with a finish which provides biocompatibility, to thereby form the implant prosthesis.

4. The method of any one of claims 1, 2 or 3 wherein the implant prosthesis is biocompatible in mouse testing of implanted micron sized particles of the alloy.

5. In a method for treating a patient by implanting an implant prosthesis with modification of a bone surface so as to accept the prosthesis, the improvement which comprises:
   (a) implanting the implant prosthesis wherein the implant prosthesis comprises a forged and machined alloy consisting essentially of Ti(x %)Al(y %)Nb, wherein x is between about 45 to 54% by atoms and wherein y is between about 15 to 25% by atoms and the balance is Nb, wherein the implant is able to withstand at least $10^5$ fatigue cycles at a stress of 400 MPa and has a surface finish which is biocompatible.

6. The method of claim 5 wherein the alloy is Ti-15Al-33Nb.

7. In a method for treating a patient by implanting an implant prosthesis with modification of a bone surface so as to accent the prosthesis, the improvement which comprises:
  (a) implanting the implant prosthesis wherein the implant prosthesis comprises a forged and machined alloy of Ti-21Al-29Nb, wherein the implant is able to withstand at least $10^5$ fatigue cycles at a stress of 400 MPa and has a surface finish which is biocompatible.

8. The method of claim 1 wherein the forging of the alloy is at a temperature greater than 899° C.

9. The method of claim 1 wherein the forged alloy exhibits a fatigue strength of at least 800 MPa.

10. The method of claim 9 wherein the forged alloy exhibits a fatigue strength of at least 800-950 MPa.

11. The method of claim 10 wherein the forged alloy exhibits a fatigue strength between 850-875 MPa.

12. A method for forming a finished implant prosthesis which comprises:
  (a) providing an unforged alloy consisting essentially of Ti(x %)Al(y %)Nb wherein x is between about 50 to 52% by atoms, y is between about 15 to 21% by atoms and the balance is niobium;
  (b) forging the alloy at an elevated temperature below a melting point of the alloy in a shape which is an implant preform; and
  (c) machining the implant preform to provide a machined implant; and
  (d) finishing the exposed surfaces of the implant so as to provide the exposed surfaces with a finish which provides biocompatibility, to thereby form the implant prosthesis.

13. The method of claim 12 wherein the forging of the alloy is at a temperature greater than 899° C.

14. The method of claim 12 wherein the forged alloy exhibits a fatigue strength of at least 800 MPa.

15. The method of claim 14 wherein the forged alloy exhibits a fatigue strength between 800-900 MPa.

16. The method of claim 15 wherein the forged alloy exhibits a fatigue strength between 850-875 Mpa.

* * * * *

UNITED STATES PATENT AND TRADEMARK OFFICE
CERTIFICATE OF CORRECTION

| | | |
|---|---|---|
| PATENT NO. | : 7,682,473 B2 | Page 1 of 1 |
| APPLICATION NO. | : 11/583666 | |
| DATED | : March 23, 2010 | |
| INVENTOR(S) | : Carl J. Boehlert | |

It is certified that error appears in the above-identified patent and that said Letters Patent is hereby corrected as shown below:

Column 14, line 37, "$\sigma<750$" should be --$\sigma\leq750$--.

Column 14, line 39, "$\sigma>820$" should be --$\sigma\geq820$--.

Column 23, line 15, "TRACP" should be --TRAcP--.

Column 32, line 27, "$\alpha2+B2+O$" should be --$\alpha_2+B2+O$--.

Column 32, line 53, "low f values" should be --low $\epsilon_f$ values--.

Column 37, line 8, Claim 7, "accent" should be --accept--.

Column 38, line 21, Claim 16, "Mpa" should be --MPa--.

Signed and Sealed this

Third Day of August, 2010

David J. Kappos
*Director of the United States Patent and Trademark Office*